(12) United States Patent
Pardoll et al.

(10) Patent No.: US 7,767,202 B2
(45) Date of Patent: Aug. 3, 2010

(54) MODULATION OF SYSTEMIC IMMUNE RESPONSES BY TRANSPLANTATION OF HEMATOPOIETIC STEM CELLS TRANSDUCED WITH GENES ENCODING ANTIGENS AND ANTIGEN PRESENTING CELL REGULATORY MOLECULES

(75) Inventors: Drew M. Pardoll, Brookeville, MD (US); Linzhao Cheng, Columbia, MD (US); Yan Cui, New Orleans, LA (US); Curt I Civin, Towson, MD (US); Katherine Whartenby, Baltimore, MD (US)

(73) Assignee: The Johns Hopkins University, Baltimore, MD (US)

( * ) Notice: Subject to any disclaimer, the term of this patent is extended or adjusted under 35 U.S.C. 154(b) by 647 days.

(21) Appl. No.: 10/471,559

(22) PCT Filed: Mar. 18, 2002

(86) PCT No.: PCT/US02/08411

§ 371 (c)(1), (2), (4) Date: Mar. 18, 2004

(87) PCT Pub. No.: WO02/074345

PCT Pub. Date: Sep. 26, 2002

(65) Prior Publication Data

US 2004/0142468 A1 Jul. 22, 2004

Related U.S. Application Data

(60) Provisional application No. 60/276,853, filed on Mar. 16, 2001.

(51) Int. Cl.
*A61K 48/00* (2006.01)
(52) U.S. Cl. ............... 424/93.21; 424/93.2; 435/375
(58) Field of Classification Search .................. None
See application file for complete search history.

(56) References Cited

U.S. PATENT DOCUMENTS

| | | | |
|---|---|---|---|
| 5,589,466 A | 12/1996 | Felgner et al. | |
| 5,738,852 A | 4/1998 | Robinson et al. | |
| 5,925,362 A | 7/1999 | Spitler et al. | |
| 6,130,052 A | 10/2000 | Van Baren et al. | |
| 6,149,906 A | 11/2000 | Mosca | |
| 6,165,785 A | 12/2000 | Ogle et al. | |
| 6,194,204 B1 | 2/2001 | Crawford et al. | |
| 6,214,804 B1 | 4/2001 | Felgner et al. | |
| 6,224,870 B1 | 5/2001 | Segal | |
| 6,245,525 B1 | 6/2001 | Martelange et al. | |
| 6,294,378 B1 | 9/2001 | Houghton et al. | |
| 6,734,014 B1 * | 5/2004 | Hwu et al. ............... | 435/325 |

FOREIGN PATENT DOCUMENTS

WO WO-98/46083 10/1998

OTHER PUBLICATIONS

Rosenzweig et al, Blood 1999;94:2271-86.*
Andrews R et al, Exp Hematol 2000;28:508-18.*
Kim et al, Blood 2000;96:1-8.*
Frey et al, J Leukoc. Biol. 2006;79:652-62.*
Bodey et al, Anticancer Res 2000;20:2665-76.*
Radoja et al, Mol Med 2000;6:465-79.*
Muthukumar et al, Transplant Proceedings 2000;32:1041-2.*
Game et al, Wien Klin Wochenschr 2001;113:832-38.*
Platt et al, Nat Biotech Mar. 2002;20231-2.*
Allen et al. Cell Immunol 1997;181:127-38.*
C. I. Civin et al., (1984) "Antigenic Analysis Of Hematopoiesis: III A Hematopoietic Progenitor Cell Surface Antigen Defined by a Monoclonal Antibody Raised against KG-1a Cells," *The Journal Of Immunology*, vol. 133, No. 1: pp. 157-165.
H. L. Davis (1999) "DNA Vaccines for Prophylactic or Therapeutic Immunization Against Hepatitis B Virus," *The Mount Sinai Journal Of Medicine*, vol. 66, No. 2: pp. 84-90.
J. J. Kim et al., (2001) "Induction of immune responses and safety profiles in rhesus macaques immunized with a DNA vaccine expressing human prostate specific," *Oncogene*, vol. 20: pp. 4497-4506.
I. A. Ramshaw et al., (1997) "DNA vaccines for the treatment of autoimmune disease," *Immunology and Cell Biology*, vol. 75: pp. 409-413.
J. Banchereau & R. N. Steinman (1998) "Denderitic cells and the control of immunity," *Nature*, vol. 392, No. 19: pp. 245-252.
J. W. Young & R. M. Steinman (1996) "The Hematopoietic Development of Dendritic Cells: A Distinct Pathway for Myeloid Differentiation," *Stem Cells*, vol. 14: pp. 376-387.
M. Cella et al., (1997) "Origin, maturation and antigen presenting function of dendritic cells," *Current Opinion in Immunology*, vol. 9: pp. 10-16.
A. Curti et al., (2001) "Dendritic cell differentiation form hematopoietic CD34+ progenitor cells," *Journal of Biological Regulators and Homeostatic Agents*, vol. 15: pp. 49-52.
D. M. Pardoll (1998) "Cancer vaccines," *Nature Medicine Vaccine Supplement*, vol. 4, No. 5: pp. 525-531.
D. Herlyn & B. Birebent (1999) "Advances in cancer vaccine development," *The Finnish Medical Society Duodecim, Ann. Med.*, vol. 31: pp. 66-78.
D. N. J. Hart (1997) "Dendritic Cells: Unique Leukocyte Populations Which Control the Primary Immune Response," *Blood*, vol. 90, No. 9: pp. 3245-3287.

(Continued)

*Primary Examiner*—Q. Janice Li
(74) *Attorney, Agent, or Firm*—Foley Hoag, LLP

(57) ABSTRACT

The invention provides methods and compositions for the modulation of systemic immune responses by transplantation of hematopoietic stem cells transduced with genes encoding antigens and antigen presenting cell regulatory molecules. The invention includes bi-cistronic lentiviral expression vectors adapted for antigen expression in antigen presenting cells for use in DNA vaccines directed against pathogens and tumor antigens as well as for the treatment of autoimmune disease and for the establishment of antigen tolerance.

18 Claims, 8 Drawing Sheets

OTHER PUBLICATIONS

L. Cheng et al., (1997) "A GFP reporter system to assess gene transfer and expression in human hematopoietic progenitor cells," *Gene Therapy*, vol. 4: pp. 1013-1022.

L. Cheng et al., (1998) "Sustained Gene Expression in Retrovirally Transduced, Engrafting Human Hematopoietic Stem Cells and Their Lympho-Myeloid Progeny," *Blood*, vol. 92, No. 1: pp. 83-92.

E. M. Novelli et al., (1999) "Ex Vivo Culture of Cord Blood CD34+ Cells Expands Progenitor Cell Numbers, Preserves Engraftment Capacity in Nonobese Diabetic/Severe Combined Immunodeficient Mice, and Enhances Retroviral Transduction Efficiency," *Human Gene Therapy* vol. 10: pp. 2927-2940.

Z. Gao et al., (2001) "High Levels of Transgen Expression Following Transdcution of Long-Term NOD/SCID-Repopulating Human Cells with a Modified Lentiviral Vector," *Stem Cells*, vol. 19: pp. 247-259.

Y. Cui et al., (2000) "Specific Transgene Expression in Antigen Presenting Cells Derived From Lentivirally Transduced Hematopoietic Stem/Progenitor Cells," *Abstracts/Experimental Hematology* 28, 62-.

Y. Cui et al., (1999) "Contributions of Viral Splice Sites and *cis*-Regulatory Elements to Lentivirus Vector Function," *Journal of Virology*, vol. 73, No. 7: pp. 6171-6176.

R. Zufferey et al., (1998) "Self-Inactivating Lentivirus Vector for Safe and Efficient In Vivo Gene Delivery," *Journal of Virology*, vol. 72, No. 12: pp. 9873-9880.

E. M. Sotomayor et al., (1999) "In vivo Blockade of CTLA-4 enhances the priming of responsive T cells but fails to prevent the induction of tumor antigen-specific tolerance." *Proc. Natl. Acad. Sci.* vol. 96: pp. 11476.

E. M. Sotomayor et al., (1999) "Conversion of tumor-specific CD4+ T-cell tolerance to T-cell priming through in vivo ligation of CD40." *Nat. Med.* vol. 5: pp. 780-787.

K. Staveley-O'Carroll et al., (1998) "Induction oaf antigen-specific T cell anergy: An early event in the course of tumor progression." *Proc. Natl. Acad. Sci.* vol. 95: pp. 1178.

B. Mach. (1999) "Regulating the Regulator." *Science* vol. 285: pp. 1367.

S. Y. Tseng et al., (2001) "B7-DC, a New Dendritic Cell Molecule with Potent Costimulatory Properties for T cells." *J. Exp. Med.* vol. 193, No. 7: pp. 839-845.

D. M. Spencer et al., (1993) "Controlling Signal Transduction with Synthetic Ligands." *Science* vol. 262: pp. 1019.

J.F. Amara et al., (1997) "A versatile synthetic dimerizer for the regulation of protein-protein interactions." *Proc. Natl. Acad. Sci USA.* vol. 94: pp. 10618.

T. Clackson et al., (1998) "Redesigning an FKBP-ligand interface to generate chemical dimerizers with novel specificity." *Proc. Natl. Acad. Sci USA.* vol. 95: pp. 10437-10442.

D. C. Thomis et al., (2001) "A Fas-based suicide switch in human T cells for the treatment of graft-versus-host disease." *Blood* vol. 97: pp. 1249-1257.

* cited by examiner

Figure 2

A. Mono-cistronic vectors

| Promoter | Gene |
|----------|------|
| EF1α | GFP |
| HLA-DRα | HA |

More DC-specific
CIITA P1
B7-DC
Minor

B. Bi-cistronic vectors

| Gene 1 | Gene 2 |
|--------|--------|
| HA | iCD40-FKBP |
|  | iFlt3-FKBP |
|  | CD40 ligand |
|  | Flt3 ligand |
|  | GM-CSF |
|  | IL-12 |

Fig 2. (A). A list of mono-cistronic lentiviral vectors we have made. The promoter from the human housekeeping gene, EF1α, is used as control. Lentiviral vectors under the control of a more DC-specific promoter (such as the CIITA promoter 1) are under construction. (B). Bi-cistronic vectors to be constructed under the control of DR or a DC-specific promoter. We will make DC activators by fusing the intracellular signaling domain of CD40 or Flt3 receptor with the FKBP domain. The engineered activator gene linked to HA gene by an IRES will be selectively expressed inside transduced DCs in a non-active form, which can be activated by a cell permeable, immunologically inert compound like FK1012. Alternatively, we will construct vectors selectively expressing CD40 ligand or Flt3 ligand in transduced DC to generate an autocrine loop. A similar autocrine or paracrine loop can be achieved for the production of GM-CSF and IL-12 by transduced DCs, if necessary.

Figure 3

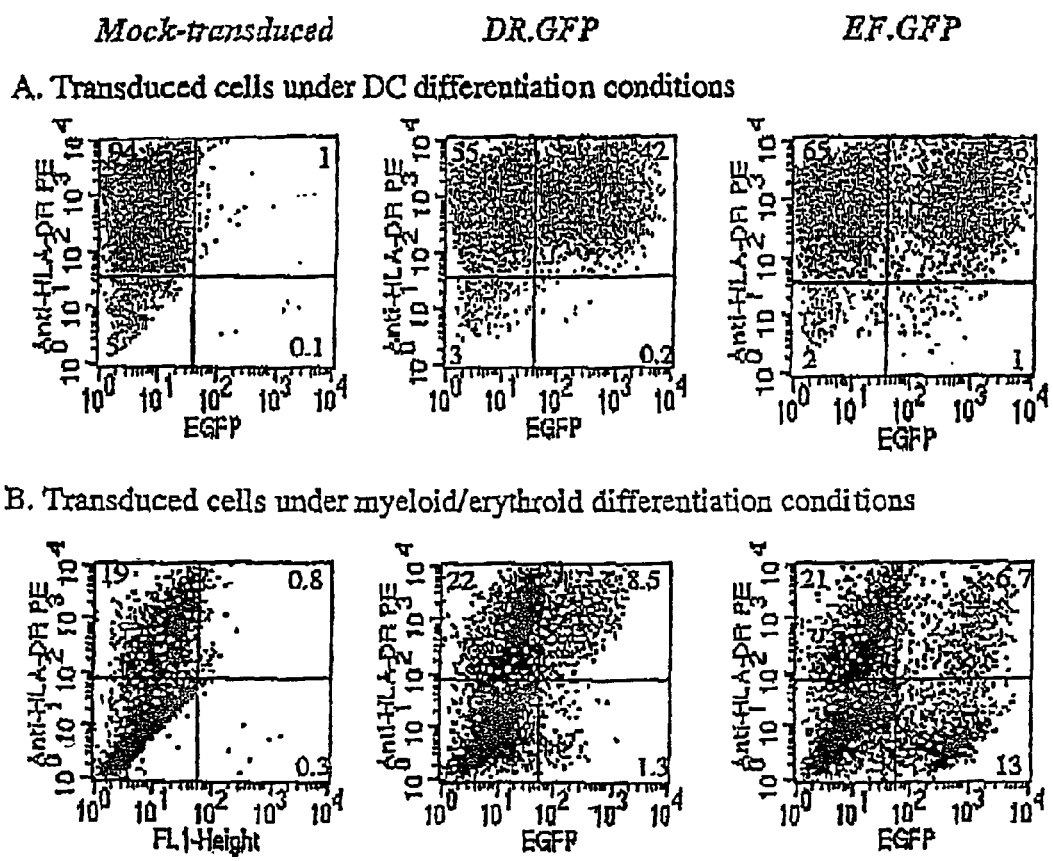

Fig 3. Human CD34+ cells from G-CSF mobilized peripheral blood were cultured overnight and transduced once (as described in 3a) with lentiviral vectors. Transgene expression is controlled by the promoter of either human DRα gene (DR.GFP vector) or a housekeeping gene EF1α promoter (EF.GFP vector). Transduced cells were cultured either in suspension with GM-CSF, IL-4 and TNFα to allow DC differentiation (A), or in methylcellulose with Epo, G-CSF, GM-CSF, SCF, IL-3 and IL-6 to allow erythroid and myeloid colony formation (B). Cells differentiated under condition A were harvested at day 7 post induction of differentiation. Cells differentiated under condition B were harvested after 14 days of CFC assays. Cells were then analyzed by FACS for GFP and cell-surface HLA-DR expression. The HLA-DR+ cells in (B) were likely to be monocytes/macrophages derived from CFU-GM. In addition, we used both lentiviral vectors to transduce non-dividing DC differentiated in vitro from human monocytes. We found that ≥20% of cells displayed DC phenotypes were readily transduced and conferred persistent GFP expression at moderate levels.

Figure 4

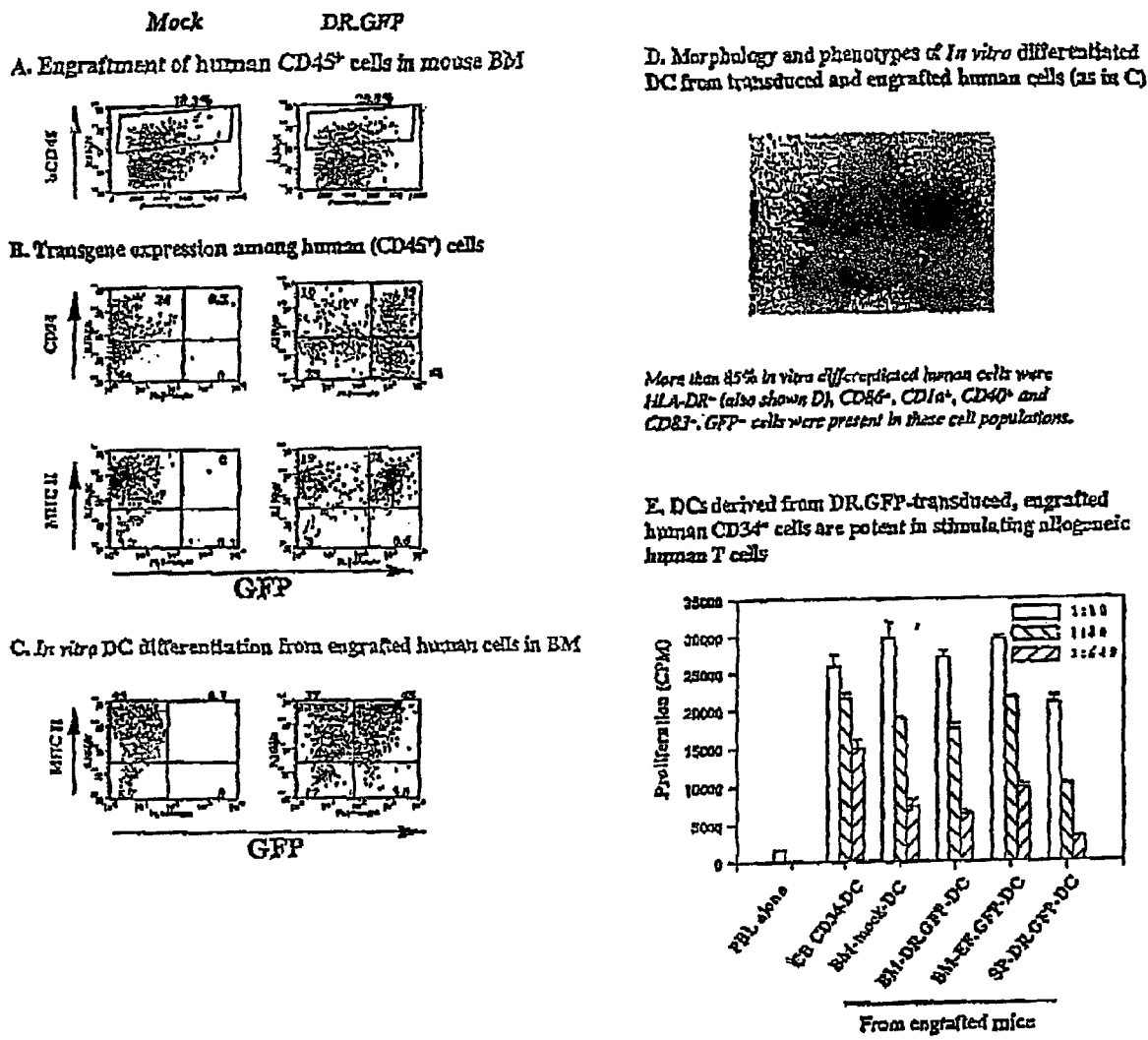

Fig 4. Human cord blood CD34+ were transduced either by DR.GFP as in Fig 3. Transduced cells were I.v. injected into conditioned NOD/SCID mice. Six to ten weeks post BMT, BM cells were harvested from engrafted and the presence of human (CD45+) donor cells (A). Human GFP+ cells that co-expressing CD34 or HLA-DR (MHC II) markers were further analyzed (B). The DRa promoter directed transgene expression exclusively in MHC II+ cells and in both CD34+ and CD34- cells. Similar results were obtained from human cells engrafted in mouse spleen, except percentages of CD45+ and CD34+ were lower (data not shown). Engrafted human cells from mouse BM were purified (by depleting mouse cells) and cultured subsequently under DC differentiation conditioned as in Fig 3A. These differentiated DCs after subsequent culture were analyzed by FACS (C and D). The DR.GFP-transduced cells showed highly selective expression in MHC II high cells after DC differentiation and maturation (C). Their morphology and phenotypes (D) and their functional activities in stimulating allogeneic human T cells (E) were also determined. The potency of these BM or splenic (SP) DCs post BMT following gene transduction (by either DR.GFP or EF.GFP LV) was high in this in vitro assay, and similar to those (CB CD34-DC) derived directly from CD34+ cells without BMT (E).

Figure 5

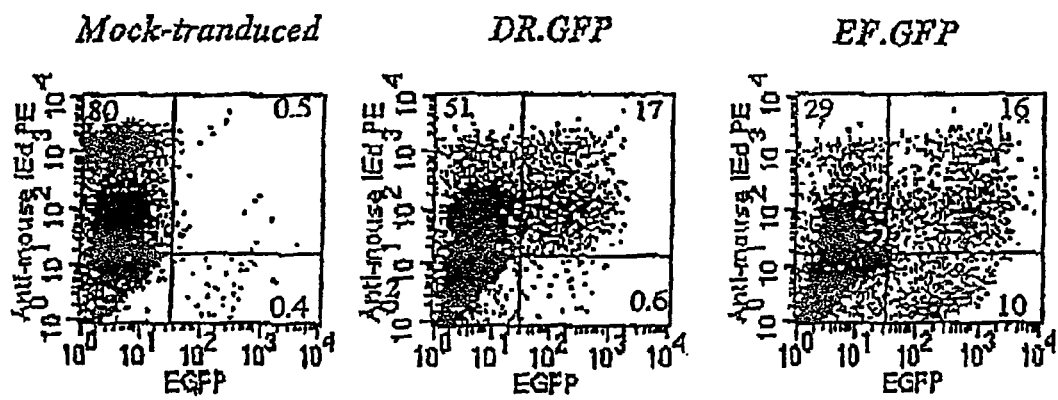

Fig 5. After one round of lentiviral transduction, mouse BM cells were cultured with GM-CSF and 10% FBS. Cells in suspension were discarded and adherent cells were fed at day 2 and 4. At day 6 adherent cells were transferred to new culture plates. Suspension cells were further selected at day 7 and harvested at day 8 post differentiation. The DC-enriched cell populations were analyzed by FACS for GFP and cell-surface I-E$^d$ (MHC II) expression. The sub-populations with the highest level of cell-surface I-E$^d$ expression were known to be DC whereas the sub-populations with medium to low levels of the cell-surface I-E$^d$ expression were immature DC and/or monocytes/macrophages. Intracellular MHC II molecules were detected in the latter population. Note that the DR.GFP vector did not express in cells lacking cell-surface I-E$^d$ (MHC II) expression.

Figure 6

A. *Phenotyping of splenic DC post BMT*

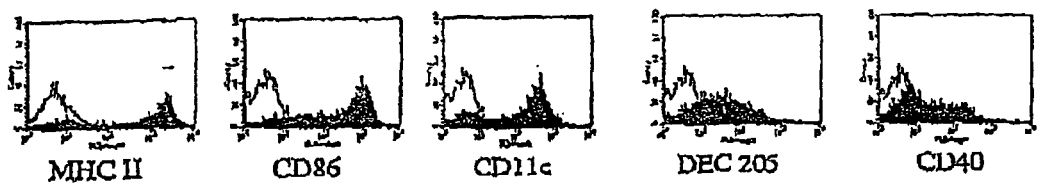

B. *Selective GFP expression in MHC II$^{high}$ splenic cells post transduction, BMT & DC activation*

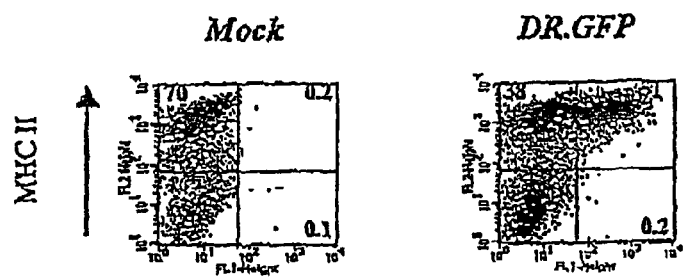

C. *Selective GFP expression in MHC II$^{high}$ BM-derived DCs post transduction and BMT*

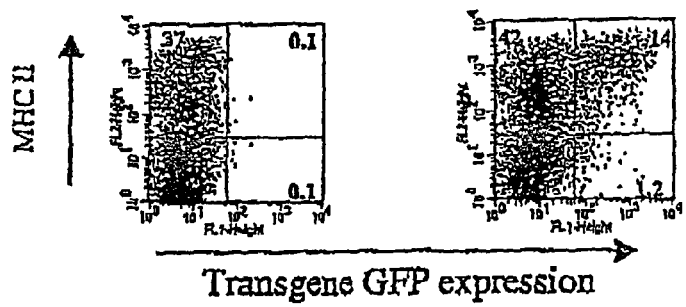

Transgene GFP expression

Fig 6. Mouse HSCs harvested from BM of BALB/c mice (without 5-FU pretreatment) were enriched by depleting mature cells expressing various hematopoietic lineage markers. After overnight culture, stimulated cells were transduced by VSV-G pseudotyped DR.GFP LV. After 1-2 rounds of transduction, cells were either injected into lethally irradiated BALB/c mice or cultured *in vitro* (with GM-CSF) for DC differentiation (as shown in Fig 5 and 7). Six to ten weeks after transplant, BM or splenic cells harvested from engrafted mice were further analyzed for their DC compartment. Splenic DCs were enriched and activated by overnight culture. The phenotypes and transgene expression are shown in (A) and (B), respectively. (C): BM cells from engrafted BALB/c mice were further differentiated into DCs as in Fig 5. Note that either donor engraftment or gene transduction rate, judged by percentages of GFP+ cells, is underestimated, since it is unlikely that we transduced all the donor cells.

Figure 8

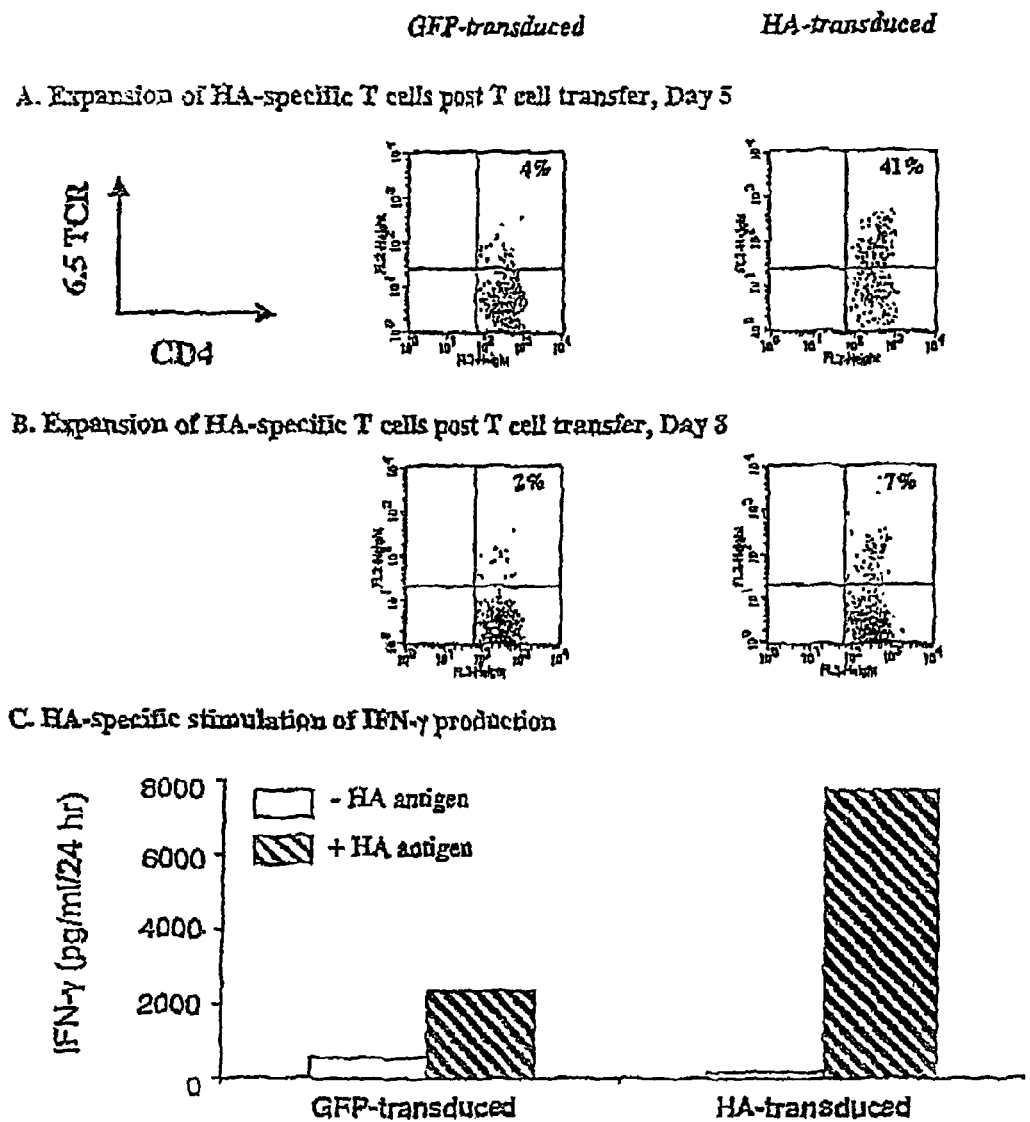

Fig 8. Ability of DR-HA-transduced HSCs post BMT to initiate HA-specific immune responses after T cell transfer from the 6.5 HA-TCR Tg mice. 3 weeks post BMT with GFP- or HA-transduced HSC, recipient mice were treated with FL daily for 10 days to expand and stimulate DC. At day 8, 6.5 T cells (2.5e⁶) were IV transferred. Frequencies of the 6.5 clonogenic CD4⁺ T cells in spleen were measured by FACS with anti-6.5 TCR and anti-CD4 antibodies at day 5 (A) or 8 (B) after T cell transfer. CD4⁺ cells are shown and percentages of 6.5 clonotypic cells among total CD4⁺ T cells are indicated (A and B). IFN-γ production of harvested T cells at day 8 were also measured (C). Harvested splenocytes from animals engrafted with GFP-transduced or HA-transduced HSC were incubated with naive BM-derived DC (as APCs) pulsed with the HA (Class II-restricted) peptide. The released IFN-γ in the first 24 hours were measured by ELISA. Averages of duplicated samples were plotted.

MODULATION OF SYSTEMIC IMMUNE RESPONSES BY TRANSPLANTATION OF HEMATOPOIETIC STEM CELLS TRANSDUCED WITH GENES ENCODING ANTIGENS AND ANTIGEN PRESENTING CELL REGULATORY MOLECULES

1. BACKGROUND OF THE INVENTION

Traditional vaccination with immunogenic proteins has eliminated or reduced the incidence of many diseases in the last century, however there are problems involved in using proteins associated with certain pathogens and disease states. Immunization by genes encoding immunogens, rather than with the immunogen itself, has opened up new possibilities for vaccine research and development and offers chances for new applications and indications for future vaccines. For example, in numerous animal models, DNA immunization has been shown to induce protective immunity against infectious diseases (viral, bacterial and protozoan). Recent examples include DNA vaccine for prophylactic or therapeutic immunization against hepatitis B virus (Davis (1999) Mt Sinai J Med. 66: 84-90). Other applications of DNA vaccine technology include the treatment of cancer as well as autoimmune disease. For example, DNA vaccines encoding prostate specific antigen (PSA) have been developed to treat prostate cancer (see e.g. Kim et al. (2001) Oncogene 20: 4497-506). Furthermore, DNA vaccine technology has applications in treating autoimmune disease, where the immune system attacks the hosts own tissues, resulting in diseases such as myasthenia gravis, diabetes or multiple sclerosis. Autoimmune disease results from a breakdown in tolerance to self antigens; however the same fundamental immunological reactions that control immune responses to foreign antigens also operate in autoimmune diseases (see e.g. Ramshaw et al. (1997) Immunol Cell Biol 75: 409-13). Accordingly, DNA vaccine technology can be used to re-establish tolerance to self antigens as well as to establish tolerance to environmental immunogens where desirable.

These DNA vaccine strategies exploit the underlying mechanisms of antigen processing, immune presentation and regulation of immune responses in order to optimize the prophylactic or therapeutic value of the vaccine, particularly for vaccines against chronic or persistent infectious diseases and tumors. DNA technology has facilitated the rapid development of plasmid-based vaccines designed to prevent viral, bacterial and parasitic infections. Current DNA vaccination strategies address: the construction of specialized vaccine plasmids; screening for protective immunogens to be encoded by these plasmids; optimization of the mode of application; analysis of vaccine pharmacokinetics; as well as analysis of vaccine safety and immunotoxicology. DNA vaccines have the potential to accelerate the research phase of new vaccines and to improve the chances of success, since finding new immunogens with the desired properties requires less effort than for conventional vaccines. However, on the way to successful DNA vaccines, several limitations must be dealt with including: the persistence and distribution of inoculated plasmid DNA in vivo; its potential to express antigens inappropriately; and the potentially deleterious ability to insert genes into the host cell's genome. Patents directed toward and describing such DNA vaccine technology include U.S. Pat. Nos. 5,589,466; 5,738,852; 5,925,362; 6,130,052; 6,149,906; 6,214,804; 6,224,870; 6,245,525; and 6,294,378, the contents of which are incorporated herein by reference.

The initiation of T cell-dependent immune responses depends on presentation of antigens by bone marrow derived antigen-presenting cells (APCs) such as dendritic cells. Tolerance induction also depends on the expression of antigens by tolerizing antigen presenting cells. Immunotherapy approaches are aimed at introducing antigen into various populations of APCs such as dendritic cells. However, the efficiency with which standard immunotherapy and vaccine approaches introduces antigens into APCs is relatively low. Standard vaccines appear to introduce antigen into relatively small numbers of APCs in the body. Ex vivo transduction or loading of dendritic cells followed by their reinfusion can increase the number of antigen-loaded APCs—however, the ex vivo manipulation and maturation of DCs appears to interfere with their ability to stimulate T cell responses subsequent to reintroduction into the body. A second problem solved relates to the importance of activating APCs with the appropriate signals. Current approaches utilize reagents provided systemically which have many side effects due to their activity on many different cell types. Accordingly, it would be desirable to have methods and compositions for the effective expression of antigens in large numbers of bone marrow derived APCs as well as to effect efficient immune responses to these APCs while avoiding undesirable side effects resulting from strategies employing systemic administration of immunostimulatory reagents.

2. SUMMARY OF THE INVENTION

The invention provides compositions, including vectors such as lentiviral expression vectors, which are used to introduce genes encoding an antigen (the antigen transgene) into hematopoietic stem cells (HSC) ex vivo. The transduced HSCs are then transplanted into a subject to be treated. In preferred embodiments, APC-stimulatory agents are also delivered to the patient to induce APC (dendritic cell) maturation, expansion and activation. These in vivo differentiated APCs express and present the antigen encoded by the transgene introduced originally into the hematopoietic stem cells ex vivo. This approach allows for the antigens into APCs systemically.

In preferred embodiments, the invention provides methods for modulating T cell-dependent immune responses to an antigen in a mammalian host. Preferably, such methods include transformation or transduction of a population of hematopoietic stem cells by first introducing a construct, e.g. a viral expression construct, that expresses two genes. In general, the first gene is a selected antigen, such as a pathogen antigen, a tumor antigen or a self-antigen. The second gene is a factor that regulates antigen presenting cell differentiation, maturation, expansion or activation. Accordingly, the transduced or transfected hematopoietic stem cells develop into antigen presenting cells that express the selected antigen either prior to or following transplantation into the host organism to be treated. This transgenic cell population thereby expresses the selected antigen and modulates responding T cell-dependent immune responses to the selected antigen in the mammalian host. The population of hematopoietic stem cells may be provided from an autologous, an allogeneic, or a xenogeneic bone marrow graft.

In preferred embodiments, the antigen is a tumor antigen such as a prostate-specific membrane antigen (PSMA), a HER2/neu gene antigen, an idiotypic immunoglobulin antigen, an idiotypic T cell receptor antigen, an SV40 antigen, and a carcinoembryonic antigen (CEA). In these embodiments, the invention is useful in treating cancers.

In other embodiment, the antigen is a pathogen antigen such as a hepatitis B antigen, a tuberculosis antigen, an HIV antigen, and a *Borrelia burgdorferi* sensu lato antigen. In these embodiments the invention is useful in treating viral and microbial infections.

In still other embodiments, the antigen is an immune tolerance-inducing antigen such as pancreatic beta-cell antigens, insulin, GAD, collagen type 11, human cartilage gp 39 (HCgp39), gp130-RAPS, myelin basic protein (MBP), proteolipid protein (PLP), myelin oligodendrocyte glycoprotein, fibrillarin, small nucleolar protein (snoRNP), thyroid stimulating factor receptor (TSH-R), histones, glycoprotein gp70, ribosomal protein, pyruvate dehydrogenase dehydrolipoamide acetyltransferase (PCD-E2), hair follicle antigens and human tropomyosin isoform 5 (hTM5). In these embodiments the invention is useful in treating autoimmune diseases and disorders such as: insulin-dependent diabetes mellitus, rheumatoid arthritis, multiple sclerosis, scleroderma, Graves' disease, systemic lupus erythematosus, primary billiary cirrhosis, alopecia areata; and ulcerative colitis.

In preferred embodiments the second gene of the transduced or transfected expression vector encodes a factor that regulates antigen presenting cell differentiation, maturation, expansion or activation such as iCD40-FKBP, iFlt3-FKBP, CD40 ligand, Flt3 ligand, GM-CSF, or IL-12.

In still other preferred embodiments, the first gene is expressed from a dendritic cell-specific promoter such as an HLA-DR promoter, a CIITA P1 promoter, a B7-DC promoter, a "minor" gene promoter, or an EF1 a promoter.

Notably, the method of the invention allows for transplantation of the transgenic cells into the mammalian host either before allowing them to develop into antigen presenting cells that express the antigen, or after. In preferred embodiments, modulation of the T cell-dependent immune response effects an immunization against a viral or microbial pathogen.

In another preferred embodiment, modulation of the T cell-dependent immune response effects an immune response against a tumor antigen. In still other preferred embodiments, modulation of the T cell-dependent immune response effects immune tolerance for an autoantigen.

In another aspect of the invention, a method for the modulation of a T cell-dependent immune response to an antigen in a mammalian host is provided. In this aspect of the invention, an expression vector encoding the first antigen gene is transduced or transfected into a population of hematopoietic stem cells and the resulting transgenic cells are contacted with a immunostimulatory factor that regulates antigen presenting cell differentiation, maturation, expansion or activation. Following this ex vivo treatment, the treated cells are further allowed to differentiate ex vivo or immediately transplanted into the mammalian host to be treated. The transgenic cells thus transplanted, develop into antigen presenting cells that express the selected antigen and thereby modulate corresponding T cell-dependent immune responses to the antigen in the mammalian host so as to, e.g., vaccinate the host against a pathogen, induce an immune response against a tumor or induce tolerance to an autoantigen.

In another preferred embodiment, the invention provides a vector expression system which includes a first gene expression cassette that expresses an antigen gene under control of an antigen presenting cell-specific promoter, and a second gene expression cassette that expresses a factor which stimulates antigen presenting cell differentiation, maturation, expansion or activation.

In preferred embodiments, the vector expression system is a lentiviral vector and the antigen presenting cell-specific promoter is an HLA-DR promoter; a CIITA P1 promoter; a B7-DC promoter; or a minor gene promoter. In other preferred embodiments, the first gene expression cassette encodes a pathogen antigen gene such as a hepatitis B antigen, a tuberculosis antigen, an HIV antigen, or a *Borrelia burgdorferi* sensu lato antigen. In other preferred embodiments, the first gene expression cassette encodes a tumor antigen such as a prostate-specific membrane antigen (PSMA), a HER2/neu gene antigen, an idiotypic immunoglobulin antigen, an idiotypic T cell receptor antigen, an SV40 antigen, or a carcinoembryonic antigen (CEA). In still other preferred embodiments, the first gene expression cassette encodes an immune tolerance-inducing antigen (e.g. an autoantigen gene) such as a pancreatic beta-cell antigen, insulin, GAD, collagen type 11, human cartilage gp 39 (HCgp39), gp130-RAPS, myelin basic protein (MBP), proteolipid protein (PLP), myelin oligodendrocyte glycoprotein, fibrillarin, small nucleolar protein (snoRNP), thyroid stimulating factor receptor (TSH-R), histones, glycoprotein gp70, ribosomal protein, pyruvate dehydrogenase dehydrolipoamide acetyltransferase (PCD-E2), hair follicle antigens, or human tropomyosin isoform 5 (hTM5). In this aspect of the invention, the factor used to that stimulate antigen presenting cell differentiation, maturation, expansion or activation may be iCD40-PKBP, iFlt3-FKBP, CD40 ligand, Flt3 ligand, GM-CSF, or IL-12.

3. BRIEF DESCRIPTION OF THE FIGURES

FIG. 2 is a schematic illustration of a number of lentiviral vectors expressing the selected antigen and the APC-stimulatory gene.

FIG. 3 includes scatter plot results of FACS studies showing that a GFP transgene driven by the DRα promoter is selectively expressed in human HLA-DR+ cells differentiated from CD34+ cells transduced by the DR.GFPSIN lentiviral vector.

FIG. 4 includes scatter plots of FACS results, a photomicrograph, and a bar graph showing that transduced human CD34+ cells engraft in vivo and generate multiple lineages of GFP+ hematopoietic cells including DCs that can stimulate allogeneic human T cell proliferation.

FIG. 5 includes scatter plots showing that a GFP transgene driven by the DRα promoter is selectively expressed in mouse MHC II+ cells differentiated from bone marrow cells transduced by the DR.GFP SIN lentiviral vector.

FIG. 6 includes histograms and scatter plots showing selective transgene expression mediated by the DRα promoter in mouse donor-derived DCs post transduction and BMT.

Figure 7:
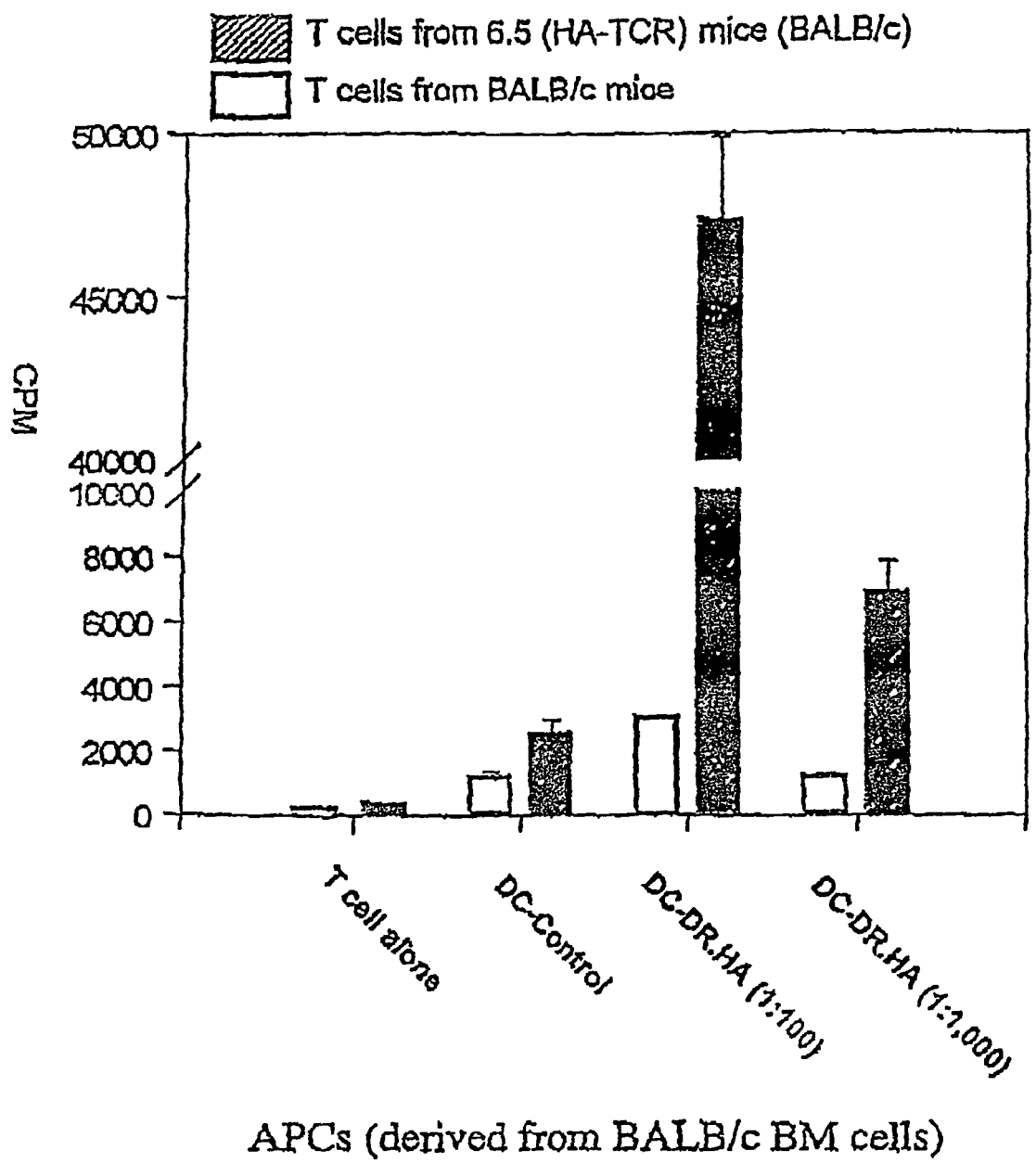

FIG. 7 is a bar graph showing mouse DCs differentiated from transduced BM cells by the DR.HA lentiviral vector can specifically and potently stimulate the proliferation of HA-specific T cells (from the 6.5 HA-TCR Tg mice).

FIG. 8 HA includes scatter plots and bar graphs showing that transduced HSCs post BMT greatly stimulate the proliferation of HA-specific CD4+ T cells and IFN-y production following adoptive T cell transfer.

4. DETAILED DESCRIPTION OF THE INVENTION

4.1. General

In general, the invention provides strategies to achieve the expression of antigens in large numbers of bone marrow derived APCs. This strategy involves the introduction of genes encoding antigen into hematopoietic stem cells ex vivo followed by transplantation of these transduced hematopoietic stem cells in vivo. This approach also allows for the introduction of genes encoding the signaling portions of molecules that regulate APC differentiation and activation. Furthermore, the invention provides approaches for selectively expressing genes encoding antigen and signaling molecules in particular APC subtypes through the use of vectors that express the transgenes under control of internal promoters that are specifically expressed in particular APC types.

In certain preferred embodiments, the invention provides methods and compositions for the efficient introduction of antigens into APCs. The invention provides methods and compositions for the ex vivo transduction or loading of dendritic cells followed by their reinfusion, while increasing the APCs ability to stimulate T cell responses subsequent to reintroduction into the host's body.

In certain other preferred embodiments, the invention provides methods and compositions to activate APCs using appropriate signals. While certain approaches to, for example, DNA vaccination utilize reagents provided systemically which have many side effects due to their activity on many different cell types, the current invention introduces signaling portions of these molecules into the vector that incorporates the antigen under control of promoters specific to particular APC types. Accordingly, in certain embodiments the invention allows for the enhancement of the specificity of the differentiation and activation functions of APCs necessary for appropriate T cell stimulation.

4.2. Definitions

For convenience, the meaning of certain terms and phrases employed in the specification, examples, and appended claims are provided below.

The term "aberrant activity", as applied to an activity of a polypeptide refers to an activity which differs from the activity of the wild-type or native polypeptide or which differs from the activity of the polypeptide in a healthy subject. An activity of a polypeptide can be aberrant because it is stronger than the activity of its native counterpart. Alternatively, an activity can be aberrant because it is weaker or absent relative to the activity of its native counterpart. An aberrant activity can also be a change in an activity. For example, an aberrant polypeptide can interact with a different target peptide. A cell can have an aberrant polypeptide activity due to overexpression or underexpression of the gene encoding the polypeptide.

The term "agonist", as used herein, is meant to refer to an agent that mimics or upregulates (e.g. potentiates or supplements) a bioactivity. A polypeptide agonist can be a wild-type protein or derivative thereof having at least one bioactivity of the wild-type polypeptide. A polypeptide therapeutic can also be a compound that upregulates expression of a polypeptide-encoding gene or which increases at least one bioactivity of a polypeptide. An agonist can also be a compound which increases the interaction of a polypeptide with another molecule.

The term "allele", which is used interchangeably herein with "allelic variant" refers to alternative forms of a gene or portions thereof. Alleles occupy the same locus or position on homologous chromosomes. When a subject has two identical alleles of a gene, the subject is said to be homozygous for the gene or allele. When a subject has two different alleles of a gene, the subject is said to be heterozygous for the gene. Alleles of a specific gene can differ from each other in a single nucleotide, or several nucleotides, and can include substitutions, deletions, and insertions of nucleotides. Frequently occurring sequence variations include transition mutations (i.e. purine to purine substitutions and pyrimidine to pyrimidine substitutions, e.g. A to G or C to T), transversion mutations (i.e. purine to pyrimidine and pyrimidine to purine substitutions, e.g. A to T or C to G), and alteration in repetitive DNA sequences (e.g. expansions and contractions of trinucleotide repeat and other tandem repeat sequences). An allele of a gene can also be a form of a gene containing a mutation.

"Antagonist" as used herein is meant to refer to an agent that downregulates (e.g. suppresses or inhibits) at least one bioactivity. An antagonist can be a compound which inhibits or decreases the interaction between a protein and another molecule, e.g., a FasL ligand and a FasL receptor. An antagonist can also be a compound that down-regulates expression of a gene or which reduces the amount of gene product protein present. The antagonist can be a dominant negative form of a polypeptide, e.g., a form of a FasL polypeptide which is capable of interacting with a target peptide. An antagonist can also be a compound that interferes with a protein-dependent signal transduction pathway. The antagonist can also be a nucleic acid encoding a dominant negative form of a polypeptide, an antisense nucleic acid, or a ribozyme capable of interacting specifically with a RNA. Yet other antagonists are molecules which bind to a polypeptide and inhibit its action. Such molecules include peptides which do not have biological activity, and which inhibit binding to target molecules, such as receptors.

The term "antibody" as used herein is intended to include whole antibodies, e.g., of any isotype (IgG, IgA, IgM, IgE, etc), and includes fragments thereof which are also specifically reactive with a vertebrate, e.g., mammalian, protein. Antibodies can be fragmented using conventional techniques and the fragments screened for utility in the same manner as described above for whole antibodies. Thus, the term includes segments of proteolytically-cleaved or recombinantly-prepared portions of an antibody molecule that are capable of selectively reacting with a certain protein. Nonlimiting examples of such proteolytic and/or recombinant fragments include Fab, F(ab')2, Fab', Fv, and single chain antibodies (scFv) containing a V[L] and/or V[H] domain joined by a peptide linker. The scFv's may be covalently or non-covalently linked to form antibodies having two or more binding sites. The subject invention includes polyclonal, monoclonal, or other purified preparations of antibodies and recombinant antibodies.

A disease, disorder, or condition "associated with" or "characterized by" an aberrant expression of a nucleic acid refers to a disease, disorder, or condition in a subject which is caused by, contributed to by, or causative of an aberrant level of expression of a nucleic acid.

"Biological activity" or "bioactivity" or "activity" or "biological function", which are used interchangeably, for the purposes herein means an effector or antigenic function that is directly or indirectly performed by a polypeptide (whether in its native or denatured conformation), or by any subsequence thereof. Biological activities include binding to a target peptide. A target polypeptide bioactivity can be modulated by directly affecting the target polypeptide. Alternatively, a target polypeptide bioactivity can be modulated by modulating the level of the target polypeptide, such as by modulating expression of the target polypeptide-encoding gene.

The term "biomarker" refers a biological molecule, e.g., a nucleic acid, peptide, hormone, etc., whose presence or concentration can be detected and correlated with a known condition, such as a disease state.

"Cells", "host cells" or "recombinant host cells" are terms used interchangeably herein. It is understood that such terms refer not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein.

A "chimeric polypeptide" or "fusion polypeptide" is a fusion of a first amino acid sequence encoding one of the subject polypeptides with a second amino acid sequence defining a domain (e.g. polypeptide portion) foreign to and not substantially homologous with any domain of the polypeptide. A chimeric polypeptide may present a foreign domain which is found (albeit in a different polypeptide) in an organism which also expresses the first polypeptide, or it may be an "interspecies", "intergenic", etc. fusion of polypeptide structures expressed by different kinds of organisms. In general, a fusion polypeptide can be represented by the general formula X-polypeptide-Y, wherein "polypeptide" represents a portion or all of a protein of interest and X and Y are independently absent or represent amino acid sequences which are not related to the protein sequence in an organism, including naturally occurring mutants.

A "delivery complex" shall mean a targeting means (e.g. a molecule that results in higher affinity binding of a gene, protein, polypeptide or peptide to a target cell surface and/or increased cellular or nuclear uptake by a target cell). Examples of targeting means include: sterols (e.g. cholesterol), lipids (e.g. a cationic lipid, virosome or liposome), viruses (e.g. adenovirus, adeno-associated virus, and retrovirus) or target cell specific binding agents (e.g. ligands recognized by target cell specific receptors). Preferred complexes are sufficiently stable in vivo to prevent significant uncoupling prior to internalization by the target cell. However, the complex is cleavable under appropriate conditions within the cell so that the gene, protein, polypeptide or peptide is released in a functional form.

The term "dendritic cell" refers to any of various accessory cells that serve as antigen-presenting cells (APCs) in the induction of an immune response. As used herein, the term "dendritic cell" includes both interdigitating dendritic cells which are present in the interstitium of most organs and are abundant in T cell-rich areas of the lymph nodes and spleen, as well as throughout the epidermis of the skin, where they are also referred to as Langerhans cells. The interdigitating dendritic cells arise from marrow precursor cells and are related in lineage to mononuclear phagocytes.

As is well known, genes may exist in single or multiple copies within the genome of an individual. Such duplicate genes may be identical or may have certain modifications, including nucleotide substitutions, additions or deletions, which all still code for polypeptides having substantially the same activity. For example, the term "DNA sequence encoding an antigen polypeptide" may thus refer to one or more antigen genes within a particular individual. Moreover, certain differences in nucleotide sequences may exist between individual organisms, which are called alleles. Such allelic differences may or may not result in differences in amino acid sequence of the encoded polypeptide yet still encode a polypeptide with the same biological activity.

The term "equivalent" is understood to include nucleotide sequences encoding functionally equivalent polypeptides. Equivalent nucleotide sequences will include sequences that differ by one or more nucleotide substitutions, additions or deletions, such as allelic variants; and will, therefore, include sequences that differ from the nucleotide sequence of the nucleic acids of the invention due to the degeneracy of the genetic code.

"Homology" or "identity" or "similarity" refers to sequence similarity between two peptides or between two nucleic acid molecules. Homology can be determined by comparing a position in each sequence which may be aligned for purposes of comparison. When a position in the compared sequence is occupied by the same base or amino acid, then the molecules are identical at that position. A degree of homology or similarity or identity between nucleic acid sequences is a function of the number of identical or matching nucleotides at positions shared by the nucleic acid sequences. A degree of identity of amino acid sequences is a function of the number of identical amino acids at positions shared by the amino acid sequences. A degree of homology or similarity of amino acid sequences is a function of the number of amino acids, i.e. structurally related, at positions shared by the amino acid sequences. An "unrelated" or "non-homologous" sequence shares less than 40% identity, though preferably less than 25% identity, with one of the sequences of the present invention.

The term "polypeptide binding partner" or "polypeptide BP" refers to various cell proteins which bind to a specified polypeptide of the invention.

The term "interact" as used herein is meant to include detectable relationships or association (e.g. biochemical interactions) between molecules, such as interaction between protein-protein, protein-nucleic acid, nucleic acid-nucleic acid, and protein-small molecule or nucleic acid-small molecule in nature.

The term "isolated" as used herein with respect to nucleic acids, such as DNA or RNA, refers to molecules separated from other DNAs, or RNAs, respectively, that are present in the natural source of the macromolecule. For example, an isolated nucleic acid encoding one of the subject polypeptides preferably includes no more than 10 kilobases (kb) of nucleic acid sequence which naturally immediately flanks the subject gene in genomic DNA, more preferably no more than 5 kb of such naturally occurring flanking sequences, and most preferably less than 1.5 kb of such naturally occurring flanking sequence. The term isolated as used herein also refers to a nucleic acid or peptide that is substantially free of cellular material, viral material, or culture medium when produced by recombinant DNA techniques, or chemical precursors or other chemicals when chemically synthesized. Moreover, an "isolated nucleic acid" is meant to include nucleic acid fragments which are not naturally occurring as fragments and would not be found in the natural state. The term "isolated" is also used herein to refer to polypeptides which are isolated from other cellular proteins and is meant to encompass both purified and recombinant polypeptides.

A "knock-in" transgenic animal refers to an animal that has had a modified gene introduced into its genome and the modified gene can be of exogenous or endogenous origin.

A "knock-out" transgenic animal refers to an animal in which there is partial or complete suppression of the expression of an endogenous gene (e.g, based on deletion of at least a portion of the gene, replacement of at least a portion of the gene with a second sequence, introduction of stop codons, the mutation of bases encoding critical amino acids, or the removal of an intron junction, etc.). In preferred embodiments, the "knock-out" gene locus corresponding to the modified endogenous gene no longer encodes a functional polypeptide activity and is said to be a "null" allele. Accordingly, knock-out transgenic animals of the present invention include those carrying one null gene mutation, as well as those carrying two null gene mutations.

A "knock-out construct" refers to a nucleic acid sequence that can be used to decrease or suppress expression of a protein encoded by endogenous DNA sequences in a cell. In a simple example, the knock-out construct is comprised of a gene with a deletion in a critical portion of the gene so that active protein cannot be expressed therefrom. Alternatively, a number of termination codons can be added to the native gene to cause early termination of the protein or an intron junction can be inactivated. In a typical knock-out construct, some portion of the gene is replaced with a selectable marker (such as the neo gene) so that the gene can be represented as follows: gene 5'/neo/gene 3', where gene 5' and gene 3', refer to genomic or cDNA sequences which are, respectively, upstream and downstream relative to a portion of the gene and where neo refers to a neomycin resistance gene. In another knock-out construct, a second selectable marker is added in a flanking position so that the gene can be represented as: gene/neo/gene/TK, where TK is a thymidine kinase gene which can be added to either the gene 5' or the gene 3' sequence of the preceding construct and which further can be selected against (i.e. is a negative selectable marker) in appropriate media. This two-marker construct allows the selection of homologous recombination events, which removes the flanking TK marker, from non-homologous recombination events which typically retain the TK sequences. The gene deletion and/or replacement can be from the exons, introns, especially intron junctions, and/or the regulatory regions such as promoters.

The term "modulation" as used herein refers to both upregulation (i.e., activation or stimulation (e.g., by agonizing or potentiating)) and downregulation (i.e. inhibition or suppression (e.g., by antagonizing, decreasing or inhibiting)).

The term "mutated gene" refers to an allelic form of a gene, which is capable of altering the phenotype of a subject having the mutated gene relative to a subject which does not have the mutated gene. If a subject must be homozygous for this mutation to have an altered phenotype, the mutation is said to be recessive. If one copy of the mutated gene is sufficient to alter the genotype of the subject, the mutation is said to be dominant. If a subject has one copy of the mutated gene and has a phenotype that is intermediate between that of a homozygous and that of a heterozygous subject (for that gene), the mutation is said to be co-dominant.

The "non-human animals" of the invention include mammalians such as rodents, non-human primates, sheep, dog, cow, chickens, amphibians, reptiles, etc. Preferred non-human animals are selected from the rodent family including rat and mouse, most preferably mouse, though transgenic amphibians, such as members of the *Xenopus* genus, and transgenic chickens can also provide important tools for understanding and identifying agents which can affect, for example, embryogenesis and tissue formation. The term "chimeric animal" is used herein to refer to animals in which the recombinant gene is found, or in which the recombinant gene is expressed in some but not all cells of the animal. The term "tissue-specific chimeric animal" indicates that one of the recombinant genes of the invention is present and/or expressed or disrupted in some tissues but not others.

As used herein, the term "nucleic acid" refers to polynucleotides or oligonucleotides such as deoxyribonucleic acid (DNA), and, where appropriate, ribonucleic acid (RNA). The term should also be understood to include, as equivalents, analogs of either RNA or DNA made from nucleotide analogs and as applicable to the embodiment being described, single (sense or antisense) and double-stranded polynucleotides.

The term "nucleotide sequence complementary to the nucleotide sequence set forth in SEQ ID No. x" refers to the nucleotide sequence of the complementary strand of a nucleic acid strand having SEQ ID No. x. The term "complementary strand" is used herein interchangeably with the term "complement". The complement of a nucleic acid strand can be the complement of a coding strand or the complement of a non-coding strand. When referring to double stranded nucleic acids, the complement of a nucleic acid having SEQ ID No. x refers to the complementary strand of the strand having SEQ ID No. x or to any nucleic acid having the nucleotide sequence of the complementary strand of SEQ ID No. x. When referring to a single stranded nucleic acid having the nucleotide sequence SEQ ID No. x, the complement of this nucleic acid is a nucleic acid having a nucleotide sequence which is complementary to that of SEQ ID No. x. The nucleotide sequences and complementary sequences thereof are always given in the 5' to 3' direction.

The term "percent identical" refers to sequence identity between two amino acid sequences or between two nucleotide sequences. Identity can each be determined by comparing a position in each sequence which may be aligned for purposes of comparison. When an equivalent position in the compared sequences is occupied by the same base or amino acid, then the molecules are identical at that position; when the equivalent site occupied by the same or a similar amino acid residue (e.g., similar in steric and/or electronic nature), then the molecules can be referred to as homologous (similar) at that position. Expression as a percentage of homology, similarity, or identity refers to a function of the number of identical or similar amino acids at positions shared by the compared sequences. Expression as a percentage of homology, similarity, or identity refers to a function of the number of identical or similar amino acids at positions shared by the compared sequences. Various alignment algorithms and/or programs may be used, including FASTA, BLAST, or ENTREZ. FASTA and BLAST are available as a part of the GCG sequence analysis package (University of Wisconsin, Madison, Wis.), and can be used with, e.g., default settings. ENTREZ is available through the National Center for Biotechnology Information, National Library of Medicine, National Institutes of Health, Bethesda, Md. In one embodiment, the percent identity of two sequences can be determined by the GCG program with a gap weight of 1, e.g., each amino acid gap is weighted as if it were a single amino acid or nucleotide mismatch between the two sequences.

Other techniques for alignment are described in *Methods in Enzymology*, vol. 266: Computer Methods for Macromolecular Sequence Analysis (1996), ed. Doolittle, Academic Press, Inc., a division of Harcourt Brace & Co., San Diego, Calif., USA. Preferably, an alignment program that permits gaps in the sequence is utilized to align the sequences. The Smith-Waterman is one type of algorithm that permits gaps in sequence alignments. See *Meth. Mol. Biol.* 70: 173-187 (1997). Also, the GAP program using the Needleman and Wunsch alignment method can be utilized to align sequences. An alternative search strategy uses MPSRCH software, which runs on a MASPAR computer. MPSRCH uses a Smith-Waterman algorithm to score sequences on a massively parallel computer. This approach improves ability to pick up distantly related matches, and is especially tolerant of small gaps and nucleotide sequence errors. Nucleic acid-encoded amino acid sequences can be used to search both protein and DNA databases.

Databases with individual sequences are described in *Methods in Enzymology*, ed. Doolittle, supra. Databases include Genbank, EMBL, and DNA Database of Japan (DDBJ).

Preferred nucleic acids have a sequence at least 70%, and more preferably 80% identical and more preferably 90% and even more preferably at least 95% identical to an nucleic acid sequence of a sequence shown in one of SEQ ID Nos. of the invention. Nucleic acids at least 90%, more preferably 95%, and most preferably at least about 98-99% identical with a nucleic acid sequence represented in one of the SEQ ID Nos. of the invention are of course also within the scope of the invention. In preferred embodiments, the nucleic acid is mammalian. In comparing a new nucleic acid with known sequences, several alignment tools are available. Examples include PileUp, which creates a multiple sequence alignment, and is described in Feng et al., J. Mol. Evol. (1987) 25:351-360. Another method, GAP, uses the alignment method of Needleman et al., J. Mol. Biol. (1970) 48:443-453. GAP is best suited for global alignment of sequences. A third method, BestFit, functions by inserting gaps to maximize the number of matches using the local homology algorithm of Smith and Waterman, Adv. Appl. Math. (1981) 2:482-489.

The term "polymorphism" refers to the coexistence of more than one form of a gene or portion (e.g., allelic variant) thereof. A portion of a gene of which there are at least two different forms, i.e., two different nucleotide sequences, is referred to as a "polymorphic region of a gene". A polymorphic region can be a single nucleotide, the identity of which differs in different alleles. A polymorphic region can also be several nucleotides long.

A "polymorphic gene" refers to a gene having at least one polymorphic region.

As used herein, the term "promoter" means a DNA sequence that regulates expression of a selected DNA sequence operably linked to the promoter, and which effects expression of the selected DNA sequence in cells. The term encompasses "tissue specific" promoters, i.e. promoters, which effect expression of the selected DNA sequence only in specific cells (e.g. cells of a specific tissue). The term also covers so-called "leaky" promoters, which regulate expression of a selected DNA primarily in one tissue, but cause expression in other tissues as well. The term also encompasses non-tissue specific promoters and promoters that constitutively express or that are inducible (i.e. expression levels can be controlled).

The terms "protein", "polypeptide" and "peptide" are used interchangeably herein when referring to a gene product.

The term "recombinant protein" refers to a polypeptide of the present invention which is produced by recombinant DNA techniques, wherein generally, DNA encoding a particular polypeptide is inserted into a suitable expression vector which is in turn used to transform a host cell to produce the heterologous protein. Moreover, the phrase "derived from", with respect to a particular recombinant gene, is meant to include within the meaning of "recombinant protein" those proteins having an amino acid sequence of a particular native polypeptide, or an amino acid sequence similar thereto which is generated by mutations including substitutions and deletions (including truncation) of a naturally occurring form of the polypeptide.

"Small molecule" as used herein, is meant to refer to a composition, which has a molecular weight of less than about 5 kD and most preferably less than about 4 kD. Small molecules can be nucleic acids, peptides, polypeptides, peptidomimetics, carbohydrates, lipids or other organic (carbon containing) or inorganic molecules. Many pharmaceutical companies have extensive libraries of chemical and/or biological mixtures, often fungal, bacterial, or algal extracts, which can be screened with any of the assays of the invention to identify compounds that modulate a bioactivity.

The term "stem cell" or "hematopoietic stem cell" means a pluripotent cell of the hematopoietic system capable of differentiating into cells of the lymphoid and myeloid lineages.

As used herein, the term "specifically hybridizes" or "specifically detects" refers to the ability of a nucleic acid molecule of the invention to hybridize to at least approximately 6, 12, 20, 30, 50, 100, 150, 200, 300, 350, 400 or 425 consecutive nucleotides of a vertebrate gene, preferably a mammalian FasL gene.

The term "transfected stem cell" means a stem cell into which exogenous DNA or an exogenous DNA gene has been introduced by retroviral infection or other means well known to those of ordinary skill in the art.

The term "ex vivo gene therapy" means the in vitro transfection or retroviral infection of stem cells to form transfected stem cells prior to introducing the transfected stem cells into a mammal.

The term "quiescent stem cell" means a stem cell in the $G_1$ or $G_0$ phase of the cell cycle. A population of cells is considered herein to be a population of quiescent cells when at least 50%, preferably at least 70%, more preferably at least 80% of the cells are in the $G_1$ or $G_0$ phase of the cell cycle. Quiescent cells exhibit a single DNA peak by flow-cytometry analysis, a standard technique well known to those of ordinary skill in the arts of immunology and cell biology. Another technique useful for determining whether a population of cells is quiescent is the addition of a chemical agent to the cell culture medium that is toxic only to actively cycling cells, i.e., DNA synthesizing cells, and does not kill quiescent cells. Non-exclusive examples of such chemical agents include hydroxyurea and high specific activity tritiated thymidine ($^3$HtdR). A population of cells is evaluated as to the percent in an actively cycling state by the percent of the cell population killed by the chemical agent. A cell population in which in vitro tritiated thymidine killing is less than approximately 30%, preferably less than approximately 10%, more preferably less than approximately 5%, is considered to be quiescent.

The term "early repopulating stem cells" means stem cells which are capable of engrafting into the bone marrow of a host mammal within approximately 6 weeks post-transplantation.

The term "late repopulating stem cells," also termed "long-term repopulating cells" means myelolymphoid stem cells which are capable of engrafting into the bone marrow of a host mammal after approximately 6 weeks post-transplantation.

By the term "engrafting" or engraftment" is meant the persistence of proliferating stem cells in a particular location over time. Thus, early repopulating stem cells do not persist for more than about 6 weeks, whereas late repopulating stem cells persist for longer, and preferably much longer, than about 6 weeks.

Cycling stem cells can be treated to become quiescent by serum or isoleucine starvation. Quiescence can also be induced by reduction of nutrients in the culture medium such that the cycling stem cells enter and remain in the $G_1$ or $G_0$ phase of the cell cycle while the nutrient level is reduced. These methods can be used alone or in combination.

By the term "expanded population" is meant a population of cells, wherein at least 50% of the cells have divided at least once. In certain embodiments of the invention, the cells may be induced to divide by the administration of cell cycling agents such as 5-FU and/or cytokines such as IL-3, IL-6, IL-11, and other growth stimulating factors well known to those of ordinary skill in the art of immunology.

By the term "non-myeloablated host mammal" is meant a mammal which has not undergone irradiation, or other treatment (such as chemical treatment) well known to those of ordinary skill in the art, to cause the death of the bone marrow cells of the mammal.

By the term "myeloablated host mammal" is meant a mammal which has undergone irradiation, or other treatment, such as chemical treatment, well known to those of ordinary skill in the art, to cause the death of at least 50% of the bone marrow cells of the mammal.

"Transcriptional regulatory sequence" is a generic term used throughout the specification to refer to DNA sequences, such as initiation signals, enhancers, and promoters, which induce or control transcription of protein coding sequences with which they are operably linked. In preferred embodiments, transcription of a genes is under the control of a promoter sequence (or other transcriptional regulatory sequence) which controls the expression of the recombinant gene in a cell-type in which expression is intended. It will also be understood that the recombinant gene can be under the control of transcriptional regulatory sequences which are the same or which are different from those sequences which control transcription of the naturally-occurring forms of the polypeptide.

As used herein, the term "transfection" means the introduction of a nucleic acid, e.g., via an expression vector, into a recipient cell by nucleic acid-mediated gene transfer. "Transformation", as used herein, refers to a process in which a cell's genotype is changed as a result of the cellular uptake of exogenous DNA or RNA, and, for example, the transformed cell expresses a recombinant form of a polypeptide of the invention (e.g. a gene encoding an antigen or an APC immunostimulatory activity) or, in the case of antisense expression from the transferred gene, the expression of a naturally-occurring form of the particular target polypeptide is disrupted.

As used herein, the term "transgene" means a nucleic acid sequence (encoding, e.g., one of the antigen or APC immunostimulatory polypeptides, or an antisense transcript thereto) which has been introduced into a cell. A transgene could be partly or entirely heterologous, i.e., foreign, to the transgenic animal or cell into which it is introduced, or, is homologous to an endogenous gene of the transgenic animal or cell into which it is introduced, but which is designed to be inserted, or is inserted, into the animal's genome in such a way as to alter the genome of the cell into which it is inserted (e.g., it is inserted at a location which differs from that of the natural gene or its insertion results in a knockout). A transgene can also be present in a cell in the form of an episome. A transgene can include one or more transcriptional regulatory sequences and any other nucleic acid, such as introns, that may be necessary for optimal expression of a selected nucleic acid.

A "transgenic animal" refers to any animal, preferably a non-human mammal, bird or an amphibian, in which one or more of the cells of the animal contain heterologous nucleic acid introduced by way of human intervention, such as by transgenic techniques well known in the art. The nucleic acid is introduced into the cell, directly or indirectly by introduction into a precursor of the cell, by way of deliberate genetic manipulation, such as by microinjection or by infection with a recombinant virus. The term genetic manipulation does not include classical cross-breeding, or in vitro fertilization, but rather is directed to the introduction of a recombinant DNA molecule. This molecule may be integrated within a chromosome, or it may be extrachromosomally replicating DNA. In the typical transgenic animals described herein, the transgene causes cells to express a recombinant form of a polypeptide for use in the invention, e.g. either agonistic or antagonistic forms. However, transgenic animals in which a recombinant target gene is silent are also contemplated, as for example, the FLP or CRE recombinase dependent constructs described below. Moreover, "transgenic animal" also includes those recombinant animals in which gene disruption of one or more target genes is caused by human intervention, including both recombination and antisense techniques.

The term "treating" as used herein is intended to encompass curing as well as ameliorating at least one symptom of the condition or disease.

The term "vector" refers to a nucleic acid molecule capable of transporting another nucleic acid to which it has been linked. One type of preferred vector is an episome, i.e., a nucleic acid capable of extra-chromosomal replication. Preferred vectors are those capable of autonomous replication and/or expression of nucleic acids to which they are linked. Vectors capable of directing the expression of genes to which they are operatively linked are referred to herein as "expression vectors". In general, expression vectors of utility in recombinant DNA techniques are often in the form of "plasmids" which refer generally to circular double stranded DNA loops which, in their vector form are not bound to the chromosome. In the present specification, "plasmid" and "vector" are used interchangeably as the plasmid is the most commonly used form of vector. However, the invention is intended to include such other forms of expression vectors which serve equivalent functions and which become known in the art subsequently hereto.

The term "wild-type allele" refers to an allele of a gene which, when present in two copies in a subject results in a wild-type phenotype. There can be several different wild-type alleles of a specific gene, since certain nucleotide changes in a gene may not affect the phenotype of a subject having two copies of the gene with the nucleotide changes.

4.3. Nucleic Acids of the Present Invention

The invention provides antigen-encoding and APC-stimulatory factor-encoding and other nucleic acids, homologs thereof, and portions thereof. Preferred nucleic acids have a sequence at least about 60%, 61%, 62%, 63%, 64%, 65%, 66%, 67%, 68%, 69%, 70%, 71%, 72%, 73%, 74%, 75%, 76%, 77%, 78%, 79%, 80%, and more preferably 85% homologous and more preferably 90% and more preferably 95% and even more preferably at least 99% homologous with a nucleotide sequence of a subject gene, e.g., an antigen-encoding gene Nucleic acids at least 90%, more preferably 95%, and most preferably at least about 98-99% identical with a nucleic sequence represented in one of the subject nucleic acids of the invention or complement thereof are of course also within the scope of the invention. In preferred embodiments, the nucleic acid is mammalian and in particularly preferred embodiments, includes all or a portion of the nucleotide sequence corresponding to the coding region which correspond to the coding sequences of the subject antigen-encoding DNAs.

The invention also pertains to isolated nucleic acids comprising a nucleotide sequence encoding antigen polypeptides, variants and/or equivalents of such nucleic acids. The term equivalent is understood to include nucleotide sequences encoding functionally equivalent antigen polypeptides or functionally equivalent peptides having an activity of an antigen protein such as described herein. Equivalent nucleotide sequences will include sequences that differ by one or more nucleotide substitution, addition or deletion, such as allelic variants; and will, therefore, include sequences that differ from the nucleotide sequences of e.g. the corresponding antigen gene GenBank entries due to the degeneracy of the genetic code.

Preferred nucleic acids are vertebrate antigen nucleic acids. Particularly preferred vertebrate antigen nucleic acids are mammalian. Regardless of species, particularly preferred antigen nucleic acids encode polypeptides that are at least 60%, 65%, 70%, 72%, 74%, 76%, 78%, 80%, 90%, or 95% similar or identical to an amino acid sequence of a vertebrate antigenprotein. In one embodiment, the nucleic acid is a cDNA encoding a polypeptide having at least one bio-activity of the subject antigen polypeptides or APC-stimulatory factors. Preferably, the nucleic acid includes all or a portion of the nucleotide sequence corresponding to the nucleic acids available through GenBank.

Still other preferred nucleic acids of the present invention encode an antigen-encoding polypeptide which is comprised of at least 2, 5, 10, 25, 50, 100, 150 or 200 amino acid residues. For example, such nucleic acids can comprise about 50, 60, 70, 80, 90, or 100 base pairs. Also within the scope of the invention are nucleic acid molecules for use as probes/primer or antisense molecules (i.e. noncoding nucleic acid molecules), which can comprise at least about 6, 12, 20, 30, 50, 60, 70, 80, 90 or 100 base pairs in length.

Another aspect of the invention provides a nucleic acid which hybridizes under stringent conditions to a nucleic acid represented by any of the subject nucleic acids of the invention. Appropriate stringency conditions which promote DNA hybridization, for example, 6.0×sodium chloride/sodium citrate (SSC) at about 45° C., followed by a wash of 2.0×SSC at 50° C., are known to those skilled in the art or can be found in Current Protocols in Molecular Biology, John Wiley & Sons, N.Y. (1989), 6.3.1-6.3.6 or in Molecular Cloning: A Laboratory Manual, Cold Spring Harbor Press (1989). For example, the salt concentration in the wash step can be selected from a low stringency of about 2.0×SSC at 50° C. to a high stringency of about 0.2×SSC at 50° C. In addition, the temperature in the wash step can be increased from low stringency conditions at room temperature, about 22° C., to high stringency conditions at about 65° C. Both temperature and salt may be varied, or temperature and salt concentration may be held constant while the other variable is changed. In a preferred embodiment, an antigen nucleic acid of the present invention will bind to one of the subject SEQ ID Nos. or complement thereof under moderately stringent conditions, for example at about 2.0×SSC and about 40° C. In a particularly preferred embodiment, an antigen-encoding nucleic acid sequence of the present invention will bind to one of the nucleic acids of the invention which correspond to an antigen-encoding ORF nucleic acid sequences, under high stringency conditions.

Nucleic acids having a sequence that differs from the nucleotide sequences shown in one of the nucleic acids of the invention or complement thereof due to degeneracy in the genetic code are also within the scope of the invention. Such nucleic acids encode functionally equivalent peptides (i.e., peptides having a biological activity of an antigen-encoding polypeptide) but differ in sequence from the sequence shown in the sequence listing due to degeneracy in the genetic code. For example, a number of amino acids are designated by more than one triplet. Codons that specify the same amino acid, or synonyms (for example, CAU and CAC each encode histidine) may result in "silent" mutations which do not affect the amino acid sequence of an antigen polypeptide. However, it is expected that DNA sequence polymorphisms that do lead to changes in the amino acid sequences of the subject antigen polypeptides will exist among mammals. One skilled in the art will appreciate that these variations in one or more nucleotides (e.g., up to about 3-5% of the nucleotides) of the nucleic acids encoding polypeptides having an activity of an antigen-encoding polypeptide may exist among individuals of a given species due to natural allelic variation.

4.3.1 Probes and Primers

The nucleotide sequences determined from the cloning of antigen genes from mammalian organisms will further allow for the generation of probes and primers designed for use in identifying and/or cloning other antigen homologs in other cell types, e.g., from other tissues, as well as antigen homologs from other mammalian organisms. For instance, the present invention also provides a probe/primer comprising a substantially purified oligonucleotide, which oligonucleotide comprises a region of nucleotide sequence that hybridizes under stringent conditions to at least approximately 12, preferably 25, more preferably 40, 50 or 75 consecutive nucleotides of sense or anti-sense sequence selected from one of the nucleic acids (e.g. an antigen-encoding nucleic acid) of the invention.

In preferred embodiments, the antigen primers are designed so as to optimize specificity and avoid secondary structures which affect the efficiency of priming. Optimized PCR primers of the present invention are designed so that "upstream" and "downstream" primers have approximately equal melting temperatures such as can be estimated using the formulae: $T_m=81.5°$ C. $-16.6$ $(\log_{10}[Na^+])+41(\%G+C)-0.63$ (%formamide)$-(600/$length); or $T_m(°$ C.$)=2(A/T)+4(G/C)$.

Likewise, probes based on the subject antigen sequences can be used to detect transcripts or genomic sequences encoding the same or homologous proteins, for use, e.g, in prognostic or diagnostic assays (further described below). The invention provides probes which are common to alternatively spliced variants of the antigen transcript, such as those corresponding to at least 12 consecutive nucleotides complementary to a sequence found in any of the gene sequences of the invention. In addition, the invention provides probes which hybridize specifically to alternatively spliced forms of the antigen transcript. Probes and primers can be prepared and modified, e.g., as previously described herein for other types of nucleic acids.

4.3.3. Antigens

The invention provides for antigens and antigen-expressing genes for use in the invention as described below.

4.3.3.1 Pathogen Antigens for Immunization Against Infectious Disease

Where the antigen encoded by the transduced expression vector is a pathogen antigen, such as a bacterial or viral antigen, the invention allows for the treatment and protection against infectious disease—i.e. in traditional DNA vaccine applications. Numerous pathogen antigens for use in this aspect of the invention are known in the art and may be obtained using e.g. standard cloning techniques and/or the nucleic acid and polypeptide sequence information provided in GenBank and other sources (see e.g. www.ncbi.nlm.nih.gov/entrez).

Exemplary pathogen antigens for use in the invention include: hepatitis B antigen (e.g. HBcAg or the secreted form HBeAg of the core protein of hepatitis B virus (HBV), see e.g. Kuhrober (1997) Int Immunol 9: 1203-12) for use in treating and preventing hepatitis B infection; tuberculosis antigen for use in treating and preventing tuberculosis (see e.g. Montgomery (2000) Brief Bioinform 1: 289-96); HIV antigen (e.g. gp160) for use in treating and preventing HIV infections (see e.g. Schultz et al. (2000) Intervirology 43: 197-217); and *Borrelia burgdorferi* sensu lato antigens (e.g. outer surface lipoprotein A (OspA)) for treating and preventing Lyme disease (see e.g. Simon et al. (1999) Zentralbl Bakteriol 289:

690-5). Moreover, the sequencing of bacterial genomes and subsequent identification of surface-exposed microbial structures and their conservation in natural populations of pathogenic species allows for the rapid identification of prime candidates for many additional pathogen antigens for use in the invention (see e.g. Saunder and Moxon (1998) Curr Opin Biotechnol 9: 618-23).

4.3.3.2 Tumor Antigens for Treatment of Cancers

Where the antigen encoded by the transduced expression vector is a tumor antigen, the invention allows for the treatment and protection against cancers. Numerous tumor antigens for use in this aspect of the invention are known in the art and may be obtained using e.g. standard cloning techniques and/or the nucleic acid and polypeptide sequence information provided in GenBank and other sources (see e.g. www.ncbi.nlm.nih.gov/entrez).

Exemplary tumor antigens for use in the invention include: the prostate-specific membrane antigen (PSMA) to treat prostate cancer (see e.g. Mincheff et al. (2000) Eur Urol 38: 208-17); the HER2/neu gene antigen to treat breast cancer (see e.g. Lachman et al. (2001) Cancer Gene Ther 8: 259-68); idiotypic immunoglobulin sequences to treat B-cell malignancies (see e.g. Stevenson et al. (2001) Ann Hematol 80 suppl 3: B132-4); idiotypic T cell receptor antigens to treat T cell malignancies (see e.g. Reddy et al. (2001) Ann NY Acad Scie 941: 97-105); an SV40 tumor antigen to treat SV40-expressing tumors (see e.g. Watts et al. (2000) Dev Biol (Basel) 104: 143-7); and carcinoembryonic antigen (CEA) and CD40 ligand antigen to treat carcinomas (see e.g. Xiang et al. (2001) J Immunol 167: 4560-5).

Also included are fusions of such tumor antigens to antigenic polypeptides (e.g. tetanus toxin polypeptides see e.g. Stevenson et al. (2001) Ann Hematol 80 suppl 3: B132-4) to increase the immune response to the tumor antigen.

4.3.3.3 Auto-antigens for Treatment of Autoimmune Disease

Where the antigen encoded by the transduced expression vector is an autoantigen, the invention allows for the induction of tolerance to the autoantigen for the treatment of autoimmune disease. For example, autoantibodies directed against the acetylcholine receptor (AChR) are observed in patients with Myasthenia gravis, and, accordingly, AchR-antigen expressing vectors may be used in the invention to treat and prevent Myasthenia gravis.

Notably, even in diseases where the pathogenic autoantigen is unknown, bystander suppression may be induced using antigens present in the anatomical vicinity. For example, autoantibodies to collagen are observed in rheumatoid arthritis and, accordingly, a collagen-encoding gene may be utilized as the antigen-expressing gene module in order to treat rheumatoid arthritis (see e.g. Choy (2000) Curr Opin Investig Drugs 1: 58-62). Furthermore, tolerance to beta cell autoantigens may be utilized to prevent development of type 1 diabetes (see e.g. Bach and Chatenoud (2001) Ann Rev Immunol 19: 131-161).

As another example, auto-antibodies directed against myelin oligodendrocyte glycoprotein (MOG) is observed in autoimmune encephalomyelitis and in many other CNS diseases as well as multiple sclerosis (see e.g. Iglesias et al. (2001) Glia 36: 22-34). Accordingly, use of MOG antigen expressing constructs in the invention allows for treatment of multiple sclerosis as well as related autoimmune disorders of the central nervous system.

Still other examples of candidate autoantigens for use in treating autoimmune disease include: pancreatic beta-cell antigens, insulin and GAD to treat insulin-dependent diabetes mellitus; collagen type 11, human cartilage gp 39 (HCgp39) and gp130-RAPS for use in treating rheumatoid arthritis; myelin basic protein (MBP), proteolipid protein (PLP) and myelin oligodendrocyte glycoprotein (MOG, see above) to treat multiple sclerosis; fibrillarin, and small nucleolar protein (snoRNP) to treat scleroderma; thyroid stimulating factor receptor (TSH-R) for use in treating Graves' disease; nuclear antigens, histones, glycoprotein gp70 and ribosomal proteins for use in treating systemic lupus erythematosus; pyruvate dehydrogenase dehydrolipoamide acetyltransferase (PCD-E2) for use in treating primary billiary cirrhosis; hair follicle antigens for use in treating alopecia areata; and human tropomyosin isoform 5 (hTM5) for use in treating ulcerative colitis.

4.4. APC-Stimulatory Factors

Various cytokines and other molecules can stimulate the growth, differentiation, migration, and activation of dendritic cells or other antigen presenting cells and can also boost the ability of dendritic cells to trigger and enhance T cell responses to antigen presentation. See, e.g., Banchereau J et al., "Dendritic cells and the control of immunity." Nature (1998) 392: 245-52; Young J W et al., "The hematopoietic development of dendritic cells: a distinct pathway for myeloid differentiation." Stem Cells, (1996) 14:376-387; Cella M et al., "Origin, maturation and antigen presenting function of dendritic cells." Curr Opin Immunol. (1997) 9:10-16; Curti A et al., "Dendritic cell differentiation from hematopoietic $CD34^+$ progenitor cells. J. Biol. Regul. Homeost. Agents (2001) 15:49-52.

Examples of molecules that can modulate differentiation, maturation, expansion or activation of dendritic cells or other antigen presenting cells include ligands such as CD40 ligand, granulocyte-macrophage colony stimulating factor (GM-CSF), FMS-like receptor tyrosine kinase 3 ligand (Flt3 ligand, FL), interleukin (IL) I-alpha, IL 1-beta, IL-3, IL-4, IL-6, IL-12, IL-13, IL-15, tumor necrosis factor alpha (TNF-α), granulocyte colony stimulating factor (G-CSF), stem cell factor (SCF, also known as kit ligand, KL, Steel Factor, SF, SLF, and Mast cell growth factor, MGF), tumor necrosis factor (TNF)-related activation-induced cytokine (TRANCE), and tumor necrosis factor-related apoptosis-inducing ligand (TRAIL), and transforming growth factor β1. Fusion proteins having one or more activities ascribed to any of the above molecules may also modulate differentiation, maturation, expansion, or activation of dendritic cells or other antigen presenting cells. Any of these ligands, fusion proteins, or other molecules could be encoded as a second gene expression cassette in a vector expression system.

CD40 ligand has been reported to promote induction of dendritic cells and facilitate development of immunogenic responses. See, e.g., Borges L et al., "Synergistic action of fms-like tyrosine kinase 3 ligand and CD40 ligand in the induction of dendritic cells and generation of antitumor immunity in vivo." J Immunol. (1999) 163:1289-1297; Grewal I, Flavell R. "The CD40 ligand. At the center of the immune universe?" Immunol Res. (1997)16:59-70. Exemplary nucleic acids that encode CD40 ligand and equivalents are described (see, e.g. Genbank accession nos. X65453 and L07414), as are preparations, compositions, and methods of use (U.S. Pat. No. 6,290,972 to Armitage et al.)

GM-CSF (for exemplary nucleic acids encoding GM-CSF and equivalents, see, e.g., Genbank accession nos. X03020, X03019, X03221, E02975, E02287, E01817, E00951, E00950, A20083, A11763, and X03021) has been reported modulate mobilization, differentiation, expansion, and activation of dendritic cells and other antigen presenting cells. See, e.g., Arpinati M et al., "Granulocyte-colony stimulating factor mobilizes T helper 2-inducing dendritic cells." *Blood.* (2000) 95(8):2484-2490; Pulendran B et al., "Flt3-ligand and granulocyte colony-stimulating factor mobilize distinct human dendritic cell subsets in vivo." *J Immunol.* (2000) 165(1):566-572; Sallusto F, Lanzavecchia A, "Efficient presentation of soluble antigen by cultured human dendritic cells is maintained by granulocyte/macrophage colony-stimulating factor plus interleukin 4 and down-regulated by tumor necrosis factor α." *J Exp Med* (1994) 182: 389-400; Szabolcs P et al., "Expansion of immunostimulatory dendritic cells among the myeloid progeny of human CD34+ bone marrow precursors cultured with c-kit ligand, granulocyte-macrophage colony-stimulating factor, and TNF-α." *J Immunol* (1995) 154: 5851-61; Caux C et al., "Tumor necrosis factor α strongly potentiates interleukin-3 and granulocyte-macrophage colony-stimulating factor-induced proliferation of human CD34+ hematopoietic progenitor cells." *Blood* (1990) 75: 2292-8. Compositions, preparations, methods of manufacture and use, analogs, fusions, and equivalents of GM-CSF-encoding exemplary nucleic acid are described, e.g., in U.S. Pat. Nos. 5,641,663, 5,908,763, 5,891,429, 5,393,870, 5,073,627, 5,359,035, and in foreign patent documents JP 1991155798, JP 1990076596, JP 1989020097, GB 2212160, EP 0352707, EP 0228018, and WO8504188).

Flt3 ligand has been described to modulate mobilization, induction, and proliferation of dendritic and other antigen presenting cells. See, e.g., Pulendran B et al., "Flt3-ligand and granulocyte colony-stimulating factor mobilize distinct human dendritic cell subsets in vivo." *J Immunol.* (2000) 165(1):566-572; Borges L et al., "Synergistic action of fms-like tyrosine kinase 3 ligand and CD40 ligand in the induction of dendritic cells and generation of antitumor immunity in vivo." *J Immunol.* (1999) 163:1289-1297; Lebsack M et al., "Safety of FLT3 ligand in healthy volunteers." *Blood* (1997) 90(Suppl. 1, Abstract 751): 170 a; Lyman S D. Biologic effects and potential clinical applications of Flt3 ligand. *Curr Opin Hematol.* (1998) 5(3): 192-196; Maraskovsky E et al., "Dramatic increase in the numbers of functionally mature dendritic cells in FLT3-ligand-treated mice: multiple dendritic cell subpopulations identified." *J Exp Med* (1996) 184: 1953-62; Strobl H, et al., "Flt3-ligand in cooperation with transforming growth factor-β1 potentiates in vitro development of Langherans-type dendritic cells and allows single-cell dendritic cell cluster formation under serum-free conditions." *Blood* (1997) 90: 1425-34. Exemplary nucleic acids encoding Flt3 ligand and equivalents are disclosed, e.g., in Genbank accession nos. NM_013520, L23636, U04807, U44024, U29875, U03858, U29874, and U04806). Preparations, compositions, and methods of use are described, e.g., in U.S. Pat. Nos. 6,291,661, 5,843,423, and 5,554,512.

Exemplary nucleic acids encoding IL-12 and equivalents are described, e.g., in Genbank accession nos. AF401989, AF411293, AF180563, AF180562, AF101062, AY008847, XM_084136, M65271, AF050083, XM_004011, M86672, NM_008351, M86671, and NM_008352 and in U.S. Pat. No. 5,723,127 to Scott et al.

TNF-α has been found to affect multiple aspects of dendritic cell proliferation and development. See, e.g., Szabolcs P et al., "Expansion of immunostimulatory dendritic cells among the myeloid progeny of human CD34+ bone marrow precursors cultured with c-kit ligand, granulocyte-macrophage colony-stimulating factor, and TNF-α." *J Immunol* (1995) 154: 5851-61; Caux C et al., "Tumor necrosis factor α strongly potentiates interleukin-3 and granulocyte-macrophage colony-stimulating factor-induced proliferation of human CD34+ hematopoietic progenitor cells." *Blood* (1990) 75: 2292-8; Chen B et al., "The role of tumor necrosis factor (in modulating the quantity of peripheral blood-derived, cytokine-driven human dendritic cells and its role in enhancing the quality of dendritic cell function in presenting soluble antigens to CD4+ T cells in vitro." *Blood.* (1998) 91(12): 4652-4661. Exemplary nucleic acids encoding TNF-α and equivalents are disclosed, e.g., in Genbank accession nos. X01394, A21522, NM_013693, M20155, M38296, and M11731, and in U.S. Pat. Nos. 4,677,063, 4,677,064, 4,677, 197, and 5,298,407.

TRANCE has been reported to increase survival and immunostimulatory properties of dendritic cells. See, e.g., Josien F et al., "TRANCE, a tumor necrosis factor family member enhances the longevity and adjuvant properties of DCs in vivo." *J Exp Med.* 2000; 191(3):495-502. Exemplary nucleic acids encoding TRANCE and equivalents are disclosed, e.g., in Genbank accession nos. NM_011613, AF013170, NM_033012, NM_003701, AF053712, AF013171, and AB037599, and in U.S. Pat. No. 6,242,586.

TRAIL has been shown to promote the ability of dendritic cells to cause apoptosis-of tumor cells targets. See, e.g., Fanger N A, Maliszewski C R, Schooley K, Griffith T S. Human dendritic cells mediate cellular apoptosis via tumor necrosis factor-related apoptosis-inducing ligand (TRAIL). J Exp Med. 1999;190(8):1155-1164. Exemplary nucleic acids encoding TRAIL and equivalents are disclosed, e.g., in Genbank accession nos. U37518, NM_003810 XM_045049, U37522, NM_009425, and AB052771, and in U.S. Pat. No. 5,763,223.

Exemplary nucleic acids encoding G-CSF and equivalents are disclosed, e.g., in Genbank accession nos. M17706, X03655, X03438, X03656, M13926, NM_009971, and X05402, and in U.S. Pat. No. 4,810,643, and in foreign patent documents WO-A8702060, WO-A-8604605, and WO-A-8604506.

Exemplary nucleic acids encoding IL-4 and equivalents are disclosed, e.g., in Genbank accession nos. NM_000589, M13982, X81851, AF395008, M23442, NM_021283, M25892, X05064, X05253, and X05252, and in U.S. Pat. No. 5,017,691. See also Tarte K, Klein B. Dendritic cell-based vaccine: a promising approach for cancer immunotherapy. *Leukemia.* 1999; 13:653-663.

c-Kit ligand has been shown to support proliferation and long-term maintenance of dendritic cells, especially in synergy with other factors. See, e.g., Szabolcs P et al., "Expansion of immunostimulatory dendritic cells among the myeloid progeny of human CD34+ bone marrow precursors cultured with c-kit ligand, granulocyte-macrophage colony-stimulating factor, and TNF-α." *J Immunol* (1995)154: 5851-61. Exemplary nucleic acids encoding kit ligand and equivalents are disclosed, e.g., in Genbank accession nos. AF400437, AF400436, M59964, M59964, NM_000899, NM_003994, and U44725, and in U.S. Pat. Nos. 6,001,803 and 5,525,708.

Exemplary nucleic acids encoding IL-13 and equivalents are disclosed, e.g., in Genbank accession nos. NM_002188, X69079, L06801, U10307, AF377331, NM_008355, L13028, and M23504, and in U.S. Pat. Nos. 5,652,123 and 5,696,234.

Exemplary nucleic acids encoding IL-1a and equivalents are disclosed, e.g., in Genbank accession nos. NM_000575, M28983, X02531, M15329, AF010237, NM_013598, M57647, and X68989, and in U.S. Pat. Nos. 5,371,204, 5,008,374, 5,017,692, and 5,756,675.

Exemplary nucleic acids encoding IL-1β and equivalents are disclosed, e.g., in Genbank accession nos. X02532, M15330, and M15840, and in U.S. Pat. Nos. 5,286,847 and 5,047,505.

Exemplary nucleic acids encoding IL-6 and equivalents are disclosed, e.g., in Genbank accession nos. Y00081, X04602, M54894, M38669, and M14584, and in U.S. Pat. No. 5,338,834.

Exemplary nucleic acids encoding IL-15 and equivalents are disclosed, e.g., in Genbank accession nos. U14407, NM_000585, X91233, Z38000, X94222, Y09908, U14332, NM_008357, and AF038164, and in U.S. Pat. No. 5,747,024.

Exemplary nucleic acids encoding TGF-β1 and equivalents are disclosed, e.g., in Genbank accession nos. M38449, M55656, X05839, Y00112, X02812, J05114, AJ009862, M13177, and BC013738. See also, e.g., Strobl H et al., "Flt3-ligand in cooperation with transforming growth factor-β1 potentiates in vitro development of Langherans-type dendritic cells and allows single-cell dendritic cell cluster formation under serum-free conditions." *Blood* (1997) 90: 1425-34; Borkowsky T A et al., "A role for endogenous transforming growth factor-β1 in Langherans cell biology: the skin of transforming growth factor-β1 null mice is devoid of epidermal Langherans cells." *J. Exp. Med.* (1996) 184:4520-30.

Nucleic acids that encode molecules that block inhibitory signals are also contemplated for inclusion as Gene 2 in an expression vector. An example of an inhibitory receptor which may be blocked by an antagonist encoded as gene 2 in an exemplary expression vector is vascular endothelial growth factor receptor. See, e.g., Gabrilovich D et al., "Vascular endothelial growth factor inhibits the development of dendritic cell and dramatically affects the differentiation of multiple hematopoietic lineages in vivo." Blood 1998; 92: 4150-66.

Many of the above-mentioned ligands are known to act synergistically with one another, as described in the references cited above. Therefore, the present subject matter also contemplates expression vector embodiments comprising a tricistronic construct having a first gene expression cassette comprising an antigen gene under control of an antigen presenting cell-specific promoter, a second gene expression cassette comprising a factor gene that stimulates antigen presenting cell differentiation, maturation, expansion or activation, and a third gene expression cassette comprising a factor gene that stimulates antigen presenting cell differentiation, maturation, expansion or activation, wherein the second and third gene expression cassettes are any combination of exemplary nucleic acids or their equivalents encoding any of the exemplary molecules or their equivalents that can modulate differentiation, maturation, expansion or activation of dendritic cells or other antigen presenting cells.

4.4.1. FKBP-Fusion Proteins

In certain embodiments, the APC-stimulatory factor is a recombinant fusion protein (e.g. an iCD40-FKBP fusion protein or an iFlt3-FKBP fusion protein) comprising an FKBP protein moiety for controlled dimerization. FKBP fusion protein technology for use in the invention is provided in several U.S. patents.

4.5. Vectors

The invention further provides plasmids and vectors encoding an Antigen protein, which can be used to express an Antigen protein in a host cell. The host cell may be any prokaryotic or eukaryotic cell. Thus, a nucleotide sequence derived from the cloning of mammalian Antigen proteins, encoding all or a selected portion of the full-length protein, can be used to produce a recombinant form of an Antigen polypeptide via microbial or eukaryotic cellular processes. Ligating the polynucleotide sequence into a gene construct, such as an expression vector, and transforming or transfecting into hosts, either eukaryotic (yeast, avian, insect or mammalian) or prokaryotic (bacterial) cells, are standard procedures well known in the art.

Typically, expression vectors used for expressing, in vivo or in vitro an antigen protein contain a nucleic acid encoding an antigen polypeptide, operably linked to at least one transcriptional regulatory sequence. Regulatory sequences are art-recognized and are selected to direct expression of the subject proteins in the desired fashion (time and place). Transcriptional regulatory sequences are described in Goeddel; Gene Expression Technology: Methods in Enzymology 185, Academic Press, San Diego, Calif. (1990).

Suitable vectors for the expression of an antigen polypeptide include plasmids of the types: pBR322-derived plasmids, pEMBL-derived plasmids, pEX-derived plasmids, pBTac-derived plasmids and pUC-derived plasmids for expression in prokaryotic cells, such as *E. coli*.

The preferred mammalian expression vectors contain both prokaryotic sequences, to facilitate the propagation of the vector in bacteria, and one or more eukaryotic transcription units that are expressed in eukaryotic cells. The pcDNAI/amp, pcDNAI/neo, pRc/CMV, pSV2gpt, pSV2neo, pSV2-dhfr, pTk2, pRSVneo, pMSG, pSVT7, pko-neo and pHyg derived vectors are examples of mammalian expression vectors suitable for transfection of eukaryotic cells. Some of these vectors are modified with sequences from bacterial plasmids, such as pBR322, to facilitate replication and drug resistance selection in both prokaryotic and eukaryotic cells. Alternatively, derivatives of viruses such as the bovine papillomavirus (BPV-1), or Epstein-Barr virus (pHEBo, pREP-derived and p205) can be used for transient expression of proteins in eukaryotic cells. The various methods employed in the preparation of the plasmids and transformation of host organisms are well known in the art. For other suitable expression systems for both prokaryotic and eukaryotic cells, as well as general recombinant procedures, see Molecular Cloning A Laboratory Manual, $2^{nd}$ Ed., ed. by Sambrook, Fritsch and Maniatis (Cold Spring Harbor Laboratory Press: 1989) Chapters 16 and 17.

In a preferred embodiment, the promoter is a constitutive promoter, e.g., a strong viral promoter, e.g., CMV promoter. The promoter can also be cell- or tissue-specific, that permits substantial transcription of the DNA only in predetermined cells, e.g., in professional antigen presenting cells, such as a promoter specific for fibroblasts, or smooth muscle cells, retinal cells or RPE cells. A smooth muscle specific promoter is. e.g. the promoter of the smooth muscle cell marker SM22alpha (Akyura et al., (2000) *Mol Med* 6:983. Retinal pigment epithelial cell specific promoter is, e.g., the promoter of the Rpe65 gene (Boulanger et al. (2000) *J Biol Chem* 275:31274). The promoter can also be an inducible promoter, e.g., a metallothionein promoter. Other inducible promoters include those that are controlled by the inducible binding, or activation, of a transcription factor, e.g., as described in U.S. Pat. Nos. 5,869,337 and 5,830,462 by Crabtree et al., describing small molecule inducible gene expression (a genetic switch); International patent applications PCT/US94/01617, PCT/US95/10591, PCT/US96/09948 and the like, as well as in other heterologous transcription systems such as those involving tetracyclin-based regulation reported by Bujard et al., generally referred to as an allosteric "off-switch" described by Gossen and Bujard (Proc. Natl. Acad. Sci. U.S.A. (1992) 89:5547) and in U.S. Pat. Nos. 5,464,758; 5,650,298; and 5,589,362 by Bujard et al. Other inducible transcription systems involve steroid or other hormone-based regulation.

The polynucleotide of the invention together with all necessary transcriptional and translational control sequences is referred to herein as "construct of the invention" or "transgene of the invention."

The polynucleotide of the invention may also be introduced into the cell in which it is to be expressed together with another DNA sequence (which may be on the same or a different DNA molecule as the polynucleotide of the invention) coding for another agent. Exemplary agents are further described below. In one embodiment, the DNA encodes a polymerase for transcribing the DNA, and may comprise recognition sites for the polymerase and the injectable preparation may include an initial quantity of the polymerase.

In certain instances, it may be preferred that the polynucleotide is translated for a limited period of time so that the polypeptide delivery is transitory. This can be achieved, e.g., by the use of an inducible promoter.

The polynucleotides used in the present invention may also be produced in part or in total by chemical synthesis, e.g., by the phosphoramidite method described by Beaucage and Carruthers, Tetra. Letts., 22:1859-1862 (1981) or the triester method according to the method described by Matteucci et al., J. Am. Chem. Soc., 103:3185 (1981), and may be performed on commercial automated oligonucleotide synthesizers. A double-stranded fragment may be obtained from the single stranded product of chemical synthesis either by synthesizing the complementary strand and annealing the strand together under appropriate conditions or by adding the complementary strand using DNA polymerase with an appropriate primer sequence.

The polynucleotide of the invention operably linked to all necessary transcriptional and translational regulation elements can be injected as naked DNA into a subject. In a preferred embodiment, the polynucleotide of the invention and necessary regulatory elements are present in a plasmid or vector. Thus, the polynucleotide of the invention may be DNA, which is itself non-replicating, but is inserted into a plasmid, which may further comprise a replicator. The DNA may be a sequence engineered so as not to integrate into the host cell genome.

Preferred vectors for use according to the invention are expression vectors, i.e., vectors that allow expression of a nucleic acid in a cell. Preferred expression vectors are those which contain both prokaryotic sequences, to facilitate the propagation of the vector in bacteria, and one or more eukaryotic transcription units that are expressed in eukaryotic cells. The pcDNAI/amp, pcDNAI/neo, pRc/CMV, pSV2gpt, pSV2neo, pSV2-dhfr, pTk2, pRSVneo, pMSG, pSVT7, pko-neo and pHyg derived vectors are examples of mammalian expression vectors suitable for transfection of eukaryotic cells. Some of these vectors are modified with sequences from bacterial plasmids, such as pBR322, to facilitate replication and drug resistance selection in both prokaryotic and eukaryotic cells. Alternatively, derivatives of viruses such as the bovine papillomavirus (BPV-1), or Epstein-Barr virus (pHEBo, pREP-derived and p205) can be used for transient expression of proteins in eukaryotic cells. The various methods employed in the preparation of the plasmids and transformation of host organisms are well known in the art. For other suitable expression systems for both prokaryotic and eukaryotic cells, as well as general recombinant procedures, see Molecular Cloning A Laboratory Manual, 2$^{nd}$ Ed., ed. by Sambrook, Fritsch and Maniatis (Cold Spring Harbor Laboratory Press: 1989) Chapters 16 and 17.

Any means for the introduction of polynucleotides into mammals, human or non-human, may be adapted to the practice of this invention for the delivery of the various constructs of the invention into the intended recipient. In one embodiment of the invention, the DNA constructs are delivered to cells by transfection, i.e., by delivery of "naked" DNA or in a complex with a colloidal dispersion system. A colloidal system includes macromolecule complexes, nanocapsules, microspheres, beads, and lipid-based systems including oil-in-water emulsions, micelles, mixed micelles, and liposomes. The preferred colloidal system of this invention is a lipid-complexed or liposome-formulated DNA. In the former approach, prior to formulation of DNA, e.g., with lipid, a plasmid containing a transgene bearing the desired DNA constructs may first be experimentally optimized for expression (e.g., inclusion of an intron in the 5' untranslated region and elimination of unnecessary sequences (Felgner, et al., Ann NY Acad Sci 126-139, 1995). Formulation of DNA, e.g. with various lipid or liposome materials, may then be effected using known methods and materials and delivered to the recipient mammal. See, e.g., Canonico et al, Am J Respir Cell Mol Biol 10:24-29, 1994; Tsan et al, Am J Physiol 268; Alton et al., Nat Genet. 5:135-142, 1993 and U.S. Pat. No. 5,679,647 by Carson et al. Colloidal dispersion systems.

The targeting of liposomes can be classified based on anatomical and mechanistic factors. Anatomical classification is based on the level of selectivity, for example, organ-specific, cell-specific, and organelle-specific. Mechanistic targeting can be distinguished based upon whether it is passive or active. Passive targeting utilizes the natural tendency of liposomes to distribute to cells of the reticulo-endothelial system (RES) in organs, which contain sinusoidal capillaries. Active targeting, on the other hand, involves alteration of the liposome by coupling the liposome to a specific ligand such as a monoclonal antibody, sugar, glycolipid, or protein, or by changing the composition or size of the liposome in order to achieve targeting to organs and cell types other than the naturally occurring sites of localization.

The surface of the targeted delivery system may be modified in a variety of ways. In the case of a liposomal targeted delivery system, lipid groups can be incorporated into the lipid bilayer of the liposome in order to maintain the targeting ligand in stable association with the liposomal bilayer. Various linking groups can be used for joining the lipid chains to the targeting ligand. Naked DNA or DNA associated with a delivery vehicle, e.g., liposomes, can be administered to several sites in a subject (see below). For example, smooth muscle cells can be targeted with an antibody binding specifically to SM22α, a smooth muscle cell marker. Retinal cells and RPE cells can similarly be targeted.

In a preferred method of the invention, the DNA constructs are delivered using viral vectors. The transgene may be incorporated into any of a variety of viral vectors useful in gene therapy, such as recombinant retroviruses, adenovirus, adeno-associated virus (AAV), and herpes simplex virus-1, or recombinant bacterial or eukaryotic plasmids. While various viral vectors may be used in the practice of this invention, AAV- and adenovirus-based approaches are of particular interest. Such vectors are generally understood to be the recombinant gene delivery system of choice for the transfer of exogenous genes in vivo, particularly into humans. The following additional guidance on the choice and use of viral vectors may be helpful to the practitioner. As described in greater detail below, such embodiments of the subject expression constructs are specifically contemplated for use in various in vivo and ex vivo gene therapy protocols.

A. Adenoviral Vectors

A viral gene delivery system useful in the present invention utilizes adenovirus-derived vectors. Knowledge of the genetic organization of adenovirus, a 36 kB, linear and double-stranded DNA virus, allows substitution of a large piece of adenoviral DNA with foreign sequences up to 8 kB. In contrast to retrovirus, the infection of adenoviral DNA into host cells does not result in chromosomal integration because adenoviral DNA can replicate in an episomal manner without potential genotoxicity. Also, adenoviruses are structurally stable, and no genome rearrangement has been detected after extensive amplification. Adenovirus can infect virtually all epithelial cells regardless of their cell cycle stage. So far, adenoviral infection appears to be linked only to mild disease such as acute respiratory disease in the human.

Adenoviruses have been shown in particular to be efficient in gene delivery to the RPE cells. For example, Baffi et al. describe the delivery of an adenovirus encoding vascular endothelial growth factor to the subretinal space in the rat, resulting in the expression of VEGF in the RPE cells of the rat (Baffi et al. (2000) *Invest Ophthalmol Vis Sci* 41:3582). Another reference describes that laser photocoagulation further increases the susceptibility of proliferating RPE cells to adenovirus-mediated gene delivery (Lai et al. (1999) *Curr Eye Res* 19:411). Sakamoto et al. describe that a vitrectomy also improves adenovirus-mediated gene delivery to the retina (Sakamoto et al. (1998) Gene Ther. 5: 1088). Ali et al. report that co-injection of adenovirus expressing CTLA4-Ig prolongs adenovirally mediated gene expression in the mouse retina, by blocking T cell activation (Ali et al. (1998) Gene Ther. 5:1561). Other references decribing expression of a transgene in retinal cells and RPE cells, upon injection of an adenoviral vector comprising the transgene in the vitreous cavity of eyes of non-human animals include Lai et al. (2000): *Invest Ophthalmol Vis Sci* 41:580; Yu et al. (2000) *Growth Factors* 17:301; and Rackoczy et al. (1998) *Aust N Z J Ophthalmol* 26 Suppl 1:S56.

Adenovirus is particularly suitable for use as a gene transfer vector because of its mid-sized genome, ease of manipulation, high titer, wide target-cell range, and high infectivity. Both ends of the viral genome contain 100-200 base pair (bp) inverted terminal repeats (ITR), which are cis elements necessary for viral DNA replication and packaging. The early (E) and late (L) regions of the genome contain different transcription units that are divided by the onset of viral DNA replication. The E1 region (E1A and E1B) encodes proteins responsible for the regulation of transcription of the viral genome and a few cellular genes. The expression of the E2 region (E2A and E2B) results in the synthesis of the proteins for viral DNA replication. These proteins are involved in DNA replication, late gene expression, and host cell shut off (Renan (1990) Radiotherap. Oncol. 19:197). The products of the late genes, including the majority of the viral capsid proteins, are expressed only after significant processing of a single primary transcript issued by the major late promoter (MLP). The MLP (located at 16.8 m.u.) is particularly efficient during the late phase of infection, and all the mRNAs issued from this promoter possess a 5' tripartite leader (TL) sequence which makes them preferred mRNAs for translation.

The genome of an adenovirus can be manipulated such that it encodes a gene product of interest, but is inactivated in terms of its ability to replicate in a normal lytic viral life cycle (see, for example, Berkner et al., (1988) BioTechniques 6:616; Rosenfeld et al., (1991) Science 252:431-434; and Rosenfeld et al., (1992) Cell 68:143-155). Suitable adenoviral vectors derived from the adenovirus strain Ad type 5 dl324 or other strains of adenovirus (e.g., Ad2, Ad3, Ad7 etc.) are well known to those skilled in the art. Recombinant adenoviruses can be advantageous in certain circumstances in that they are not capable of infecting nondividing cells and can be used to infect a wide variety of cell types, including airway epithelium (Rosenfeld et al., (1992) cited supra), endothelial cells (Lemarchand et al., (1992) PNAS USA 89:6482-6486), hepatocytes (Herz and Gerard, (1993) PNAS USA 90:2812-2816) and muscle cells (Quantin et al., (1992) PNAS USA 89:2581-2584).

Adenovirus vectors have also been used in vaccine development (Grunhaus and Horwitz (1992) Siminar in Virology 3:237; Graham and Prevec (1992) Biotechnology 20:363). Experiments in administering recombinant adenovirus to different tissues include trachea instillation (Rosenfeld et al. (1991); Rosenfeld et al. (1992) Cell 68:143), muscle injection (Ragot et al. (993) Nature 361:647), peripheral intravenous injection (Herz and Gerard (1993) Proc. Natl. Acad. Sci. U.S.A. 90:2812), and stereotactic inoculation into the brain (Le Gal La Salle et al. (1993) Science 254:988).

Furthermore, the virus particle is relatively stable and amenable to purification and concentration, and as above, can be modified so as to affect the spectrum of infectivity. Additionally, adenovirus is easy to grow and manipulate and exhibits broad host range in vitro and in vivo. This group of viruses can be obtained in high titers, e.g., $10^9$-$10^{11}$ plaque-forming unit (PFU)/ml, and they are highly infective. The life cycle of adenovirus does not require integration into the host cell genome. The foreign genes delivered by adenovirus vectors are episomal, and therefore, have low genotoxicity to host cells. No side effects have been reported in studies of vaccination with wild-type adenovirus (Couch et al., 1963; Top et al., 1971), demonstrating their safety and therapeutic potential as in vivo gene transfer vectors. Moreover, the carrying capacity of the adenoviral genome for foreign DNA is large (up to 8 kilobases) relative to other gene delivery vectors (Berkner et al., supra; Haj-Ahmand and Graham (1986) J. Virol. 57:267). Most replication-defective adenoviral vectors currently in use and therefore favored by the present invention are deleted for all or parts of the viral E1 and E3 genes but retain as much as 80% of the adenoviral genetic material (see, e.g., Jones et al., (1979) Cell 16:683; Berkner et al., supra; and Graham et al., in Methods in Molecular Biology, E. J. Murray, Ed. (Humana, Clifton, N.J., 1991) vol. 7. pp. 109-127). Expression of the inserted polynucleotide of the invention can be under control of, for example, the E1A promoter, the major late promoter (MLP) and associated leader sequences, the viral E3 promoter, or exogenously added promoter sequences.

Other than the requirement that the adenovirus vector be replication defective, or at least conditionally defective, the nature of the adenovirus vector is not believed to be crucial to the successful practice of the invention. The adenovirus may be of any of the 42 different known serotypes or subgroups A-F. Adenovirus type 5 of subgroup C is the preferred starting material in order to obtain the conditional replication-defective adenovirus vector for use in the method of the present invention. This is because Adenovirus type 5 is a human adenovirus about which a great deal of biochemical and genetic information is known, and it has historically been used for most constructions employing adenovirus as a vector. As stated above, the typical vector according to the present invention is replication defective and will not have an adenovirus E1 region. Thus, it will be most convenient to introduce the nucleic acid of interest at the position from which the E1 coding sequences have been removed. However, the position of insertion of the polynucleotide or construct on the invention (also referred to as "nucleic acid of interest") in a region within the adenovirus sequences is not critical to the present invention. For example, it may also be inserted in lieu of the deleted E3 region in E3 replacement vectors as described previously by Karlsson et. al. (1986) or in the E4 region where a helper cell line or helper virus complements the E4 defect.

A preferred helper cell line is 293 (ATCC Accession No. CRL1573). This helper cell line, also termed a "packaging cell line" was developed by Frank Graham (Graham et al. (1987) J. Gen. Virol. 36:59-72 and Graham (1977) J. General Virology 68:937-940) and provides E1A and E1B in trans. However, helper cell lines may also be derived from human cells such as human embryonic kidney cells, muscle cells, hematopoietic cells or other human embryonic mesenchymal or epithelial cells. Alternatively, the helper cells may be derived from the cells of other mammalian species that are permissive for human adenovirus. Such cells include, e.g., Vero cells or other monkey embryonic mesenchymal or epithelial cells.

Adenoviruses can also be cell type specific, i.e., infect only restricted types of cells and/or express a transgene only in restricted types of cells. For example, the viruses comprise a gene under the transcriptional control of a transcription initiation region specifically regulated by target host cells, as described e.g., in U.S. Pat. No. 5,698,443, by Henderson and Schuur, issued Dec. 16, 1997. Thus, replication competent adenoviruses can be restricted to certain cells by, e.g., inserting a cell specific response element to regulate a synthesis of a protein necessary for replication, e.g., E1A or E1B.

DNA sequences of a number of adenovirus types are available from Genbank. For example, human adenovirus type 5 has GenBank Accession No.M73260. The adenovirus DNA sequences may be obtained from any of the 42 human adenovirus types currently identified. Various adenovirus strains are available from the American Type Culture Collection, Rockville, Md., or by request from a number of commercial and academic sources. A transgene as described herein may be incorporated into any adenoviral vector and delivery protocol, by restriction digest, linker ligation or filling in of ends, and ligation.

Adenovirus producer cell lines can include one or more of the adenoviral genes E1, E2a, and E4 DNA sequence, for packaging adenovirus vectors in which one or more of these genes have been mutated or deleted are described, e.g., in PCT/US95/15947 (WO 96/18418) by Kadan et al.; PCT/US95/07341 (WO 95/346671) by Kovesdi et al.; PCT/FR94/00624 (WO94/28152) by Imler et al.;PCT/FR94/00851 (WO 95/02697) by Perrocaudet et al., PCT/US95/14793 (WO96/14061) by Wang et al.

B. AAV Vectors

Yet another viral vector system useful for delivery of the subject polynucleotides is the adeno-associated virus (AAV). Adeno-associated virus is a naturally occurring defective virus that requires another virus, such as an adenovirus or a herpes virus, as a helper virus for efficient replication and a productive life cycle. (For a review, see Muzyczka et al., Curr. Topics in Micro. and Immunol. (1992) 158:97-129).

AAV has not been associated with the cause of any disease. AAV is not a transforming or oncogenic virus. AAV integration into chromosomes of human cell lines does not cause any significant alteration in the growth properties or morphological characteristics of the cells. These properties of AAV also recommend it as a potentially useful human gene therapy vector.

AAV is also one of the few viruses that may integrate its DNA into non-dividing cells, e.g., pulmonary epithelial cells, and exhibits a high frequency of stable integration (see for example Flotte et al., (1992) Am. J. Respir. Cell. Mol. Biol. 7:349-356; Samulski et al., (1989) J. Virol. 63:3822-3828; and McLaughlin et al., (1989) J. Virol. 62:1963-1973). Vectors containing as little as 300 base pairs of AAV can be packaged and can integrate. Space for exogenous DNA is limited to about 4.5 kb. An AAV vector such as that described in Tratschin et al., (1985) Mol. Cell. Biol. 5:3251-3260 can be used to introduce DNA into cells. A variety of nucleic acids have been introduced into different cell types using AAV vectors (see for example Hermonat et al., (1984) PNAS USA 81:6466-6470; Tratschin et al., (1985) Mol. Cell. Biol. 4:2072-2081; Wondisford et al., (1988) Mol. Endocrinol. 2:32-39; Tratschin et al., (1984) J. Virol. 51:611-619; and Flotte et al., (1993) J. Biol. Chem. 268:3781-3790).

AAV has been used successfully to introduce gene constructs into retinal cells in animals, including non-human primates. For example, an AAV virus containing a gene encoding FGF-2 was administered by subretinal injection into a transgenic rat model for retinitis pigmentosa, which resulted in reduction of the rate of photoreceptor degeneration (Lau et al. (2000) Invest. Ophthalmol. Vis. Csci. 41:3622). AAV has been used for gene transduction in photoreceptor cells in non-human animals (see, e.g., Flannery et al. (1997) PNAS 94:6916; Bennett et al. (2000) PNAS 96:9920). RPE cells have also been transduced efficiently by subretinal injection of an AAV (Bennett et al. (1997) Invest. Ophthalmol. Visual Sci. 38:2857). Grant et al. also describe that a recombinant AAV injected into the vitreous body or the subretinal space of mouse eyes results in the transduction of cells of the retinal pigment epithelium (RPE), ganglion cells and photoreceptor cells for up to three months, i.e., for as long as the experiment was conducted (Grant et al. (1997) Curr. Eye Res. 16, 949). Efficient transduction of RPE cells in non-human animals is also described in Rollins et al. (2000) *Clin Experiment Ophthalmol* 28:382-6; Ali et al. (1998) *Hum Gene Ther* 9:81; and Ali et al. (1996) Hum Mol Genet. 5:591.

The AAV-based expression vector to be used typically includes the 145 nucleotide AAV inverted terminal repeats (ITRs) flanking a restriction site that can be used for subcloning of the transgene, either directly using the restriction site available, or by excision of the transgene with restriction enzymes followed by blunting of the ends, ligation of appropriate DNA linkers, restriction digestion, and ligation into the site between the ITRs. The capacity of AAV vectors is about 4.4 kb. The following proteins have been expressed using various AAV-based vectors, and a variety of promoter/enhancers: neomycin phosphotransferase, chloramphenicol acetyl transferase, Fanconi's anemia gene, cystic fibrosis transmembrane conductance regulator, and granulocyte macrophage colony-stimulating factor (Kotin, R. M., Human Gene Therapy 5:793-801, 1994, Table I). A transgene incorporating the various DNA constructs of this invention can similarly be included in an AAV-based vector. As an alternative to inclusion of a constitutive promoter such as CMV to drive expression of the polynucleotide of interest, an AAV promoter can be used (ITR itself or AAV p5 (Flotte, et al. J. Biol. Chem. 268:3781-3790, 1993)).

Such a vector can be packaged into AAV virions by reported methods. For example, a human cell line such as 293 can be co-transfected with the AAV-based expression vector and another plasmid containing open reading frames encoding AAV rep and cap (which are obligatory for replication and packaging of the recombinant viral construct) under the control of endogenous AAV promoters or a heterologous promoter. In the absence of helper virus, the rep proteins Rep68 and Rep78 prevent accumulation of the replicative form, but upon superinfection with adenovirus or herpes virus, these proteins permit replication from the ITRs (present only in the construct containing the transgene) and expression of the viral capsid proteins. This system results in packaging of the transgene DNA into AAV virions (Carter, B. J., Current Opinion in Biotechnology 3:533-539, 1992; Kotin, R. M, Human Gene Therapy 5:793-801, 1994)). Typically, three days after transfection, recombinant AAV is harvested from the cells along with adenovirus and the contaminating adenovirus is then inactivated by heat treatment.

Methods to improve the titer of AAV can also be used to express the polynucleotide of the invention in an AAV virion. Such strategies include, but are not limited to: stable expression of the ITR-flanked transgene in a cell line followed by transfection with a second plasmid to direct viral packaging; use of a cell line that expresses AAV proteins inducibly, such as temperature-sensitive inducible expression or pharmacologically inducible expression. Alternatively, a cell can be transformed with a first AAV vector including a 5' ITR, a 3' ITR flanking a heterologous gene, and a second AAV vector which includes an inducible origin of replication, e.g., SV40 origin of replication, which is capable of being induced by an agent, such as the SV40 T antigen and which includes DNA sequences encoding the AAV rep and cap proteins. Upon induction by an agent, the second AAV vector may replicate to a high copy number, and thereby increased numbers of infectious AAV particles may be generated (see, e.g, U.S. Pat. No. 5,693,531 by Chiorini et al., issued Dec. 2, 1997. In yet another method for producing large amounts of recombinant AAV, a chimeric plasmid is used which incorporate the Epstein Barr Nuclear Antigen (EBNA) gene, the latent origin of replication of Epstein Barr virus (oriP) and an AAV genome. These plasmids are maintained as a multicopy extrachromosomal elements in cells, such as in 293 cells. Upon addition of wild-type helper functions, these cells will produce high amounts of recombinant AAV (U.S. Pat. No. 5,691, 176 by Lebkowski et al., issued Nov. 25, 1997). In another system, an AAV packaging plasmid is provided that allows expression of the rep gene, wherein the p5 promoter, which normally controls rep expression, is replaced with a heterologous promoter (U.S. Pat. No. 5,658,776, by Flotte et al., issued Aug. 19, 1997). Additionally, one may increase the efficiency of AAV transduction by treating the cells with an agent that facilitates the conversion of the single stranded form to the double stranded form, as described in Wilson et al., WO96/39530.

AAV stocks can be produced as described in Hermonat and Muzyczka (1984) PNAS 81:6466, modified by using the pAAV/Ad described by Samulski et al. (1989) J. Virol. 63:3822. Concentration and purification of the virus can be achieved by reported methods such as banding in cesium chloride gradients, as was used for the initial report of AAV vector expression in vivo (Flotte, et al. J. Biol. Chem. 268: 3781-3790, 1993) or chromatographic purification, as described in O'Riordan et al., WO97/08298.

Methods for in vitro packaging AAV vectors are also available and have the advantage that there is no size limitation of the DNA packaged into the particles (see, U.S. Pat. No. 5,688, 676, by Zhou et al., issued Nov. 18, 1997). This procedure involves the preparation of cell free packaging extracts.

For additional detailed guidance on AAV technology which may be useful in the practice of the subject invention, including methods and materials for the incorporation of a transgene, the propagation and purification of the recombinant AAV vector containing the transgene, and its use in transfecting cells and mammals, see e.g. Carter et al, U.S. Pat. No. 4,797,368 (10 Jan. 1989); Muzyczka et al, U.S. Pat. No. 5,139,941 (18 Aug. 1992); Lebkowski et al, U.S. Pat. No. 5,173,414 (22 Dec. 1992); Srivastava, U.S. Pat. No. 5,252, 479 (12 Oct. 1993); Lebkowski et al, U.S. Pat. No. 5,354,678 (11 Oct. 1994); Shenk et al, U.S. Pat. No. 5,436,146(25 Jul. 1995); Chatterjee et al, U.S. Pat. No. 5,454,935 (12 Dec. 1995), Carter et al WO 93/24641 (published 9 Dec. 1993), and Natsoulis, U.S. Pat. No. 5,622,856 (Apr. 22, 1997). Further information regarding AAVs and the adenovirus or herpes helper functions required can be found in the following articles: Berns and Bohensky (1987), "Adeno-Associated Viruses: An Update", Advanced in Virus Research, Academic Press, 33:243-306. The genome of AAV is described in Laughlin et al. (1983) "Cloning of infectious adeno-associated virus genomes in bacterial plasmids", Gene, 23: 65-73. Expression of AAV is described in Beaton et al. (1989) "Expression from the Adeno-associated virus p5 and p19 promoters is negatively regulated in trans by the rep protein", J. Virol., 63:4450-4454. Construction of rAAV is described in a number of publications: Tratschin et al. (1984) "Adeno-associated virus vector for high frequency integration, expression and rescue of genes in mammalian cells", Mol. Cell. Biol., 4:2072-2081; Hermonat and Muzyczka (1984) "Use of adeno-associated virus as a mammalian DNA cloning vector: Transduction of neomycin resistance into mammalian tissue culture cells", Proc. Natl. Acad. Sci. USA, 81:6466-6470; McLaughlin et al. (1988) "Adeno-associated virus general transduction vectors: Analysis of Proviral Structures", J. Virol., 62:1963-1973; and Samulski et al. (1989) "Helper-free stocks of recombinant adeno-associated viruses: normal integration does not require viral gene expression", J. Virol., 63:3822-3828. Cell lines that can be transformed by rAAV are those described in Lebkowski et al. (1988) "Adeno-associated virus: a vector system for efficient introduction and integration of DNA into a variety of mammalian cell types", Mol. Cell. Biol., 8:3988-3996. "Producer" or "packaging" cell lines used in manufacturing recombinant retroviruses are described in Dougherty et al. (1989) J. Virol., 63:3209-3212; and Markowitz et al. (1988) J. Virol., 62:1120-1124.

C. Hybrid Adenovirus-AAV Vectors

Hybrid Adenovirus-AAV vectors represented by an adenovirus capsid containing a nucleic acid comprising a portion of an adenovirus, and 5' and 3' ITR sequences from an AAV which flank a selected transgene under the control of a promoter. See e.g. Wilson et al, International Patent Application Publication No. WO 96/13598. This hybrid vector is characterized by high titer transgene delivery to a host cell and the ability to stably integrate the transgene into the host cell chromosome in the presence of the rep gene. This virus is capable of infecting virtually all cell types (conferred by its adenovirus sequences) and stable long term transgene integration into the host cell genome (conferred by its AAV sequences).

The adenovirus nucleic acid sequences employed in this vector can range from a minimum sequence amount, which requires the use of a helper virus to produce the hybrid virus particle, to only selected deletions of adenovirus genes, which deleted gene products can be supplied in the hybrid viral process by a packaging cell. For example, a hybrid virus can comprise the 5' and 3' inverted terminal repeat (ITR) sequences of an adenovirus (which function as origins of replication). The left terminal sequence (5') sequence of the Ad5 genome that can be used spans bp 1 to about 360 of the conventional adenovirus genome (also referred to as map units 0-1) and includes the 5' ITR and the packaging/enhancer domain. The 3' adenovirus sequences of the hybrid virus include the right terminal 3' ITR sequence which is about 580 nucleotides (about bp 35,353- end of the adenovirus, referred to as about map units 98.4-100).

The AAV sequences useful in the hybrid vector are viral sequences from which the rep and cap polypeptide encoding sequences are deleted and are usually the cis acting 5' and 3' ITR sequences. Thus, the AAV ITR sequences are flanked by the selected adenovirus sequences and the AAV ITR sequences themselves flank a selected transgene. The preparation of the hybrid vector is further described in detail in published PCT application entitled "Hybrid Adenovirus-AAV Virus and Method of Use Thereof", WO 96/13598 by Wilson et al.

For additional detailed guidance on adenovirus and hybrid adenovirus-AAV technology which may be useful in the practice of the subject invention, including methods and materials for the incorporation of a transgene, the propagation and purification of recombinant virus containing the transgene, and its use in transfecting cells and mammals, see also Wilson et al, WO 94/28938, WO 96/13597 and WO 96/26285, and references cited therein.

D. Retroviruses

The retroviruses are a group of single-stranded RNA viruses characterized by an ability to convert their RNA to double-stranded DNA in infected cells by a process of reverse-transcription (Coffin (1990) Retroviridae and their Replication" In Fields, Knipe ed. Virology. New York: Raven Press). The resulting DNA then stably integrates into cellular chromosomes as a provirus and directs synthesis of viral proteins. The integration results in the retention of the viral gene sequences in the recipient cell and its descendants. The retroviral genome contains three genes, gag, pol, and env that code for capsid proteins, polymerase enzyme, and envelope components, respectively. A sequence found upstream from the gag gene, termed psi, functions as a signal for packaging of the genome into virions. Two long terminal repeat (LTR) sequences are present at the 5' and 3' ends of the viral genome. These contain strong promoter and enhancer sequences and are also required for integration in the host cell genome (Coffin (1990), supra).

In order to construct a retroviral vector, a nucleic acid of interest is inserted into the viral genome in the place of certain viral sequences to produce a virus that is replication-defective. In order to produce virions, a packaging cell line containing the gag, pol, and env genes but without the LTR and psi components is constructed (Mann et al. (1983) Cell 33:153). When a recombinant plasmid containing a human cDNA, together with the retroviral LTR and psi sequences is introduced into this cell line (by calcium phosphate precipitation for example), the psi sequence allows the RNA transcript of the recombinant plasmid to be packaged into viral particles, which are then secreted into the culture media (Nicolas and Rubenstein (1988) "Retroviral Vectors", In: Rodriguez and Denhardt ed. Vectors: A Survey of Molecular Cloning Vectors and their Uses. Stoneham:Butterworth; Temin, (1986) "Retrovirus Vectors for Gene Transfer: Efficient Integration into and Expression of Exogenous DNA in Vertebrate Cell Genome", In: Kucherlapati ed. Gene Transfer. New York: Plenum Press; Mann et al., 1983, supra). The media containing the recombinant retroviruses is then collected, optionally concentrated, and used for gene transfer. Retroviral vectors are able to infect a broad variety of cell types. Integration and stable expression require the division of host cells (Paskind et al. (1975) Virology 67:242).

A major prerequisite for the use of retroviruses is to ensure the safety of their use, particularly with regard to the possibility of the spread of wild-type virus in the cell population. The development of specialized cell lines (termed "packaging cells") which produce only replication-defective retroviruses has increased the utility of retroviruses for gene therapy, and defective retroviruses are well characterized for use in gene transfer for gene therapy purposes (for a review see Miller, A. D. (1990) Blood 76:271). Thus, recombinant retrovirus can be constructed in which part of the retroviral coding sequence (gag, pol, env) has been replaced by nucleic acid encoding a protein of the present invention, e.g., a transcriptional activator, rendering the retrovirus replication defective. The replication defective retrovirus is then packaged into virions which can be used to infect a target cell through the use of a helper virus by standard techniques. Protocols for producing recombinant retroviruses and for infecting cells in vitro or in vivo with such viruses can be found in Current Protocols in Molecular Biology, Ausubel, F. M. et al., (eds.) Greene Publishing Associates, (1989), Sections 9.10-9.14 and other standard laboratory manuals. Examples of suitable retroviruses include pLJ, pZIP, pWE and pEM which are well known to those skilled in the art. A preferred retroviral vector is a pSR MSVtkNeo (Muller et al. (1991) Mol. Cell Biol. 11:1785 and pSR MSV(XbaI) (Sawyers et al. (1995) J. Exp. Med. 181: 307) and derivatives thereof. For example, the unique BamHI sites in both of these vectors can be removed by digesting the vectors with BamHI, filling in with Klenow and religating to produce pSMTN2 and pSMTX2, respectively, as described in PCT/US96/09948 by Clackson et al. Examples of suitable packaging virus lines for preparing both ecotropic and amphotropic retroviral systems include Crip, Cre, 2 and Am.

Retroviruses, including lentiviruses, have been used to introduce a variety of genes into many different cell types, including neural cells, epithelial cells, retinal cells, endothelial cells, lymphocytes, myoblasts, hepatocytes, bone marrow cells, in vitro and/or in vivo (see for example, review by Federico (1999) Curr. Opin. Biotechnol. 10:448; Eglitis et al., (1985) Science 230:1395-1398; Danos and Mulligan, (1988) PNAS USA 85:6460-6464; Wilson et al., (1988) PNAS USA 85:3014-3018; Armentano et al., (1990) PNAS USA 87:6141-6145; Huber et al., (1991) PNAS USA 88:8039-8043; Ferry et al., (1991) PNAS USA 88:8377-8381; Chowdhury et al., (1991) Science 254:1802-1805; van Beusechem et al., (1992) PNAS USA 89:7640-7644; Kay et al., (1992) Human Gene Therapy 3:641-647; Dai et al., (1992) PNAS USA 89:10892-10895; Hwu et al., (1993) J. Immunol. 150:4104-4115; U.S. Pat. No. 4,868,116; U.S. Pat. No. 4,980,286; PCT Application WO 89/07136; PCT Application WO 89/02468; PCT Application WO 89/05345; and PCT Application WO 92/07573).

Furthermore, it has been shown that it is possible to limit the infection spectrum of retroviruses and consequently of retroviral-based vectors, by modifying the viral packaging proteins on the surface of the viral particle (see, for example PCT publications WO93/25234, WO94/06920, and WO94/11524). For instance, strategies for the modification of the infection spectrum of retroviral vectors include: coupling antibodies specific for cell surface antigens to the viral env protein (Roux et al., (1989) PNAS USA 86:9079-9083; Julan et al., (1992) J. Gen Virol 73:3251-3255; and Goud et al., (1983) Virology 163:251-254); or coupling cell surface ligands to the viral env proteins (Neda et al., (1991) J. Biol. Chem. 266:14143-14146). Coupling can be in the form of the chemical cross-linking with a protein or other variety (e.g. lactose to convert the env protein to an asialoglycoprotein), as well as by generating fusion proteins (e.g. single-chain antibody/env fusion proteins). This technique, while useful to limit or otherwise direct the infection to certain tissue types, and can also be used to convert an ecotropic vector in to an amphotropic vector.

E. Other Viral Systems

Other viral vector systems that can be used to deliver a polynucleotide of the invention have been derived from herpes virus, e.g., Herpes Simplex Virus (U.S. Pat. No. 5,631,236 by Woo et al., issued May 20, 1997 and WO 00/08191 by Neurovex), vaccinia virus (Ridgeway (1988) Ridgeway, "Mammalian expression vectors," In: Rodriguez R L, Denhardt D T, ed. Vectors: A survey of molecular cloning vectors and their uses. Stoneham: Butterworth,; Baichwal and Sugden (1986) "Vectors for gene transfer derived from animal DNA viruses: Transient and stable expression of transferred genes," In: Kucherlapati R, ed. Gene transfer. New York: Plenum Press; Coupar et al. (1988) Gene, 68:1-10), and several RNA viruses. Preferred viruses include an alphavirus, a poxivirus, an arena virus, a vaccinia virus, a polio virus, and the like. They offer several attractive features for various mammalian cells (Friedmann (1989) Science, 244:1275-1281; Ridgeway, 1988, supra; Baichwal and Sugden, 1986, supra; Coupar et al., 1988; Horwich et al.(1990) J. Virol., 64:642-650).

With the recent recognition of defective hepatitis B viruses, new insight was gained into the structure-function relationship of different viral sequences. In vitro studies showed that the virus could retain the ability for helper-dependent packaging and reverse transcription despite the deletion of up to 80% of its genome (Horwich et al., 1990, supra). This suggested that large portions of the genome could be replaced with foreign genetic material. The hepatotropism and persistence (integration) were particularly attractive properties for liver-directed gene transfer. Chang et al. recently introduced the chloramphenicol acetyltransferase (CAT) gene into duck hepatitis B virus genome in the place of the polymerase, surface, and pre-surface coding sequences. It was co-transfected with wild-type virus into an avian hepatoma cell line. Culture media containing high titers of the recombinant virus were used to infect primary duckling hepatocytes. Stable CAT gene expression was detected for at least 24 days after transfection (Chang et al. (1991) Hepatology, 14:124A).

Since in certain embodiments, the compositions of the invention will be administered via a specific device, e.g., by injection using a syringe, the invention also provides devices, e.g., syringes, comprising a composition of the invention.

Figure 1:
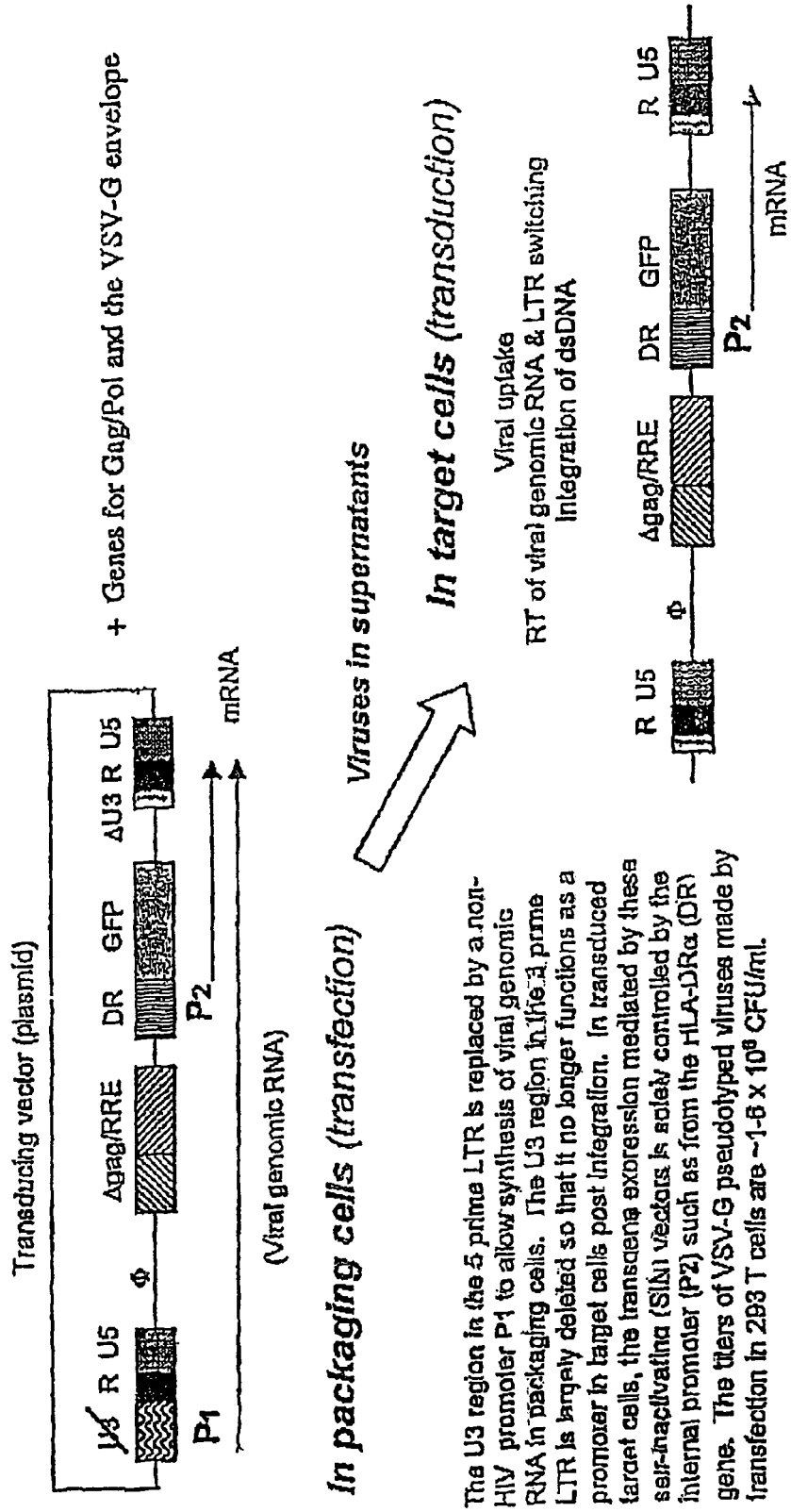
FIG. 1 is a schematic illustration of lentiviral SIN vectors which allow high levels of stable gene transfer and regulated transgene expression from a selective promoter in transduced cells.

The preferred mammalian expression vectors include retrovirus and lentivirus-based expression vectors, such as those depicted in FIG. 1 and 2. Preferred mammalian vectors typically contain both prokaryotic sequences, to facilitate the propagation of the vector in bacteria, and one or more eukaryotic transcription units that are expressed in eukaryotic cells. The pcDNAI/amp, pcDNAI/neo, pRc/CMV, pSV2gpt, pSV2neo, pSV2-dhfr, pTk2, pRSVneo, pMSG, pSVT7, pko-neo and pHyg derived vectors are examples of mammalian expression vectors suitable for transfection of eukaryotic cells. Some of these vectors are modified with sequences from bacterial plasmids, such as pBR322, to facilitate replication and drug resistance selection in both prokaryotic and eukaryotic cells. Alternatively, derivatives of viruses such as the bovine papillomavirus (BPV-1), or Epstein-Barr virus (pHEBo, pREP-derived and p205) can be used for transient expression of proteins in eukaryotic cells. The various methods employed in the preparation of the plasmids and transformation of host organisms are well known in the art. For other suitable expression systems for both prokaryotic and eukaryotic cells, as well as general recombinant procedures, see Molecular Cloning A Laboratory Manual, $2^{nd}$ Ed., ed. by Sambrook, Fritsch and Maniatis (Cold Spring Harbor Laboratory Press: 1989) Chapters 16 and 17.

In some instances, it may be desirable to express the recombinant antigen polypeptide by the use of a baculovirus expression system. Examples of such baculovirus expression systems include pVL-derived vectors (such as pVL1392, pVL1393 and pVL941), pAcUW-derived vectors (such as pAcUW1), and pBlueBac-derived vectors (such as the β-gal containing pBlueBac III)

When it is desirable to express only a portion of an Antigen protein, such as a form lacking a portion of the N-terminus, i.e. a truncation mutant which lacks the signal peptide, it may be necessary to add a start codon (ATG) to the oligonucleotide fragment containing the desired sequence to be expressed. It is well known in the art that a methionine at the N-terminal position can be enzymatically cleaved by the use of the enzyme methionine aminopeptidase (MAP). MAP has been cloned from E. coli (Ben-Bassat et al. (1987) J. Bacteriol. 169:751-757) and Salmonella typhimurium and its in vitro activity has been demonstrated on recombinant proteins (Miller et al. (1987) PNAS 84:2718-1722). Therefore, removal of an N-terminal methionine, if desired, can be achieved either in vivo by expressing Antigen derived polypeptides in a host which produces MAP (e.g., E. coli or CM89 or S. cerevisiae), or in vitro by use of purified MAP (e.g., procedure of Miller et al., supra).

Moreover, the gene constructs of the present invention can also be used as part of a gene therapy protocol to deliver nucleic acids encoding either an agonistic or antagonistic form of one of the subject Antigen proteins. Thus, another aspect of the invention features expression vectors for in vivo or in vitro transfection and expression of an Antigen polypeptide in particular cell types so as to reconstitute the function of, or alternatively, abrogate the function of Antigen in a tissue. This could be desirable, for example, when the naturally-occurring form of the protein is misexpressed or the natural protein is mutated and less active.

In addition to viral transfer methods, non-viral methods can also be employed to cause expression of a subject Antigen polypeptide in the tissue of an animal. Most non-viral methods of gene transfer rely on normal mechanisms used by mammalian cells for the uptake and intracellular transport of macromolecules. In preferred embodiments, non-viral targeting means of the present invention rely on endocytic pathways for the uptake of the subject Antigen polypeptide gene by the targeted cell. Exemplary targeting means of this type include liposomal derived systems, poly-lysine conjugates, and artificial viral envelopes.

In other embodiments transgenic animals, described in more detail below could be used to produce recombinant proteins.

4.4. Polypeptides of the Present Invention

The present invention makes available isolated Antigen polypeptides which are isolated from, or otherwise substantially free of other cellular proteins. The term "substantially free of other cellular proteins" (also referred to herein as "contaminating proteins") or "substantially pure or purified preparations" are defined as encompassing preparations of Antigen polypeptides having less than about 20% (by dry weight) contaminating protein, and preferably having less than about 5% contaminating protein. Functional forms of the subject polypeptides can be prepared, for the first time, as purified preparations by using a cloned gene as described herein.

Preferred Antigen proteins of the invention have an amino acid sequence which is at least about 60%, 65%, 66%, 67%, 68%, 69%, 70%, 71%, 72%, 73%, 74%, 75%, 76%, 77%, 78%, 79%, 80%, 85%, 90%, or 95% identical or homologous to an amino acid sequence of a SEQ ID No. of the invention, such as a sequence shown in FIG. 8B (SEQ ID No. 2) or 9B (SEQ ID No. 4). Even more preferred Antigen proteins comprise an amino acid sequence of at least 10, 20, 30, or 50 residues which is at least about 70, 80, 90, 95, 97, 98, or 99% homologous or identical to an amino acid sequence of a SEQ ID No. of the invention. Such proteins can be recombinant proteins, and can be, e.g., produced in vitro from nucleic acids comprising a nucleotide sequence of the invention or homologs thereof. For example, recombinant polypeptides preferred by the present invention can be encoded by a nucleic acid, which is at least 85% homologous and more preferably 90% homologous and most preferably 95% homologous with a nucleotide sequence set forth in a SEQ ID Nos. of the invention. Polypeptides which are encoded by a nucleic acid that is at least about 98-99% homologous with the sequence of a SEQ ID No. of the invention are also within the scope of the invention.

In a preferred embodiment, an Antigen protein of the present invention is a mammalian Antigen protein. In a particularly preferred embodiment an Antigen protein is set forth as a SEQ ID No. of the invention. In particularly preferred embodiments, an Antigen protein has an Antigen bioactivity. It will be understood that certain post-translational modifications, e.g., phosphorylation and the like, can increase the apparent molecular weight of the Antigen protein relative to the unmodified polypeptide chain.

The invention also features protein isoforms encoded by splice variants of the present invention. Such isoforms may have biological activities identical to or different from those possessed by the Antigen proteins specified by a SEQ ID No. of the invention. Such isoforms may arise, for example, by alternative splicing of one or more Antigen gene transcripts.

Antigen polypeptides preferably are capable of functioning as either an agonist or antagonist of at least one biological activity of a wild-type ("authentic") Antigen protein of the appended sequence listing. The term "evolutionarily related to", with respect to amino acid sequences of Antigen proteins, refers to both polypeptides having amino acid sequences which have arisen naturally, and also to mutational variants of human Antigen polypeptides which are derived, for example, by combinatorial mutagenesis.

Full length proteins or fragments corresponding to one or more particular motifs and/or domains or to arbitrary sizes, for example, at least 5, 10, 20, 25, 50, 75 and 100, amino acids in length are within the scope of the present invention.

Isolated peptidyl portions of Antigen proteins can be obtained by screening peptides recombinantly produced from the corresponding fragment of the nucleic acid encoding such peptides. In addition, fragments can be chemically synthesized using techniques known in the art such as conventional Merrifield solid phase f-Moc or t-Boc chemistry. For example, an Antigen polypeptide of the present invention may be arbitrarily divided into fragments of desired length with no overlap of the fragments, or preferably divided into overlapping fragments of a desired length. The fragments can be produced (recombinantly or by chemical synthesis) and tested to identify those peptidyl fragments which can function as either agonists or antagonists of a wild-type (e.g., "authentic") Antigen protein.

An Antigen polypeptide can be a membrane bound form or a soluble form. A preferred soluble Antigen polypeptide is a polypeptide which does not contain a hydrophobic signal sequence domain. Such proteins can be created by genetic engineering by methods known in the art. The solubility of a recombinant polypeptide may be increased by deletion of hydrophobic domains, such as predicted transmembrane domains, of the wild type protein.

In general, polypeptides referred to herein as having an activity (e.g., are "bioactive") of an antigen protein are defined as polypeptides which include an amino acid sequence encoded by all or a portion of the nucleic acid sequences shown in one of the subject SEQ ID Nos. and which mimic or antagonize all or a portion of the biological/biochemical activities of a naturally occurring Antigen protein. Examples of such biological activity include a region of conserved structure.

Other biological activities of the subject Antigen proteins will be reasonably apparent to those skilled in the art. According to the present invention, a polypeptide has biological activity if it is a specific agonist or antagonist of a naturally-occurring form of an Antigen protein.

Assays for determining whether a compound, e.g., a protein, such as an Antigen protein or variant thereof, has one or more of the above biological activities include those assays, well known in the art, which are used for assessing Antigen agonist and Antigen antagonist activities.

Other preferred proteins of the invention are those encoded by the nucleic acids set forth in the section pertaining to nucleic acids of the invention. In particular, the invention provides fusion proteins, e.g., Antigen-immunoglobulin fusion proteins. Such fusion proteins can provide, e.g., enhanced stability and solubility of Antigen proteins and may thus be useful in therapy. Fusion proteins can also be used to produce an immunogenic fragment of an Antigen protein. For example, the VP6 capsid protein of rotavirus can be used as an immunologic carrier protein for portions of the Antigen polypeptide, either in the monomeric form or in the form of a viral particle. The nucleic acid sequences corresponding to the portion of a subject Antigen protein to which antibodies are to be raised can be incorporated into a fusion gene construct which includes coding sequences for a late vaccinia virus structural protein to produce a set of recombinant viruses expressing fusion proteins comprising Antigen epitopes as part of the virion. It has been demonstrated with the use of immunogenic fusion proteins utilizing the Hepatitis B surface antigen fusion proteins that recombinant Hepatitis B virions can be utilized in this role as well. Similarly, chimeric constructs coding for fusion proteins containing a portion of an Antigen protein and the poliovirus capsid protein can be created to enhance immunogenicity of the set of polypeptide antigens (see, for example, EP Publication No: 0259149; and Evans et al. (1989) Nature 339:385; Huang et al. (1988) J. Virol. 62:3855; and Schlienger et al. (1992) J. Virol. 66:2).

The Multiple antigen peptide system for peptide-based immunization can also be utilized to generate an immunogen, wherein a desired portion of an Antigen polypeptide is obtained directly from organo-chemical synthesis of the peptide onto an oligomeric branching lysine core (see, for example, Posnett et al. (1988) JBC 263:1719 and Nardelli et al. (1992) J. Immunol. 148:914). Antigenic determinants of Antigen proteins can also be expressed and presented by bacterial cells.

In addition to utilizing fusion proteins to enhance immunogenicity, it is widely appreciated that fusion proteins can also facilitate the expression of proteins, and accordingly, can be used in the expression of the Antigen polypeptides of the present invention. For example, Antigen polypeptides can be generated as glutathione-S-transferase (GST-fusion) proteins. Such GST-fusion proteins can enable easy purification of the Antigen polypeptide, as for example by the use of glutathione-derivatized matrices (see, for example, Current Protocols in Molecular Biology, eds. Ausubel et al. (N.Y.: John Wiley & Sons, 1991)). Additionally, fusion of Antigen polypeptides to small epitope tags, such as the FLAG or hemagluttinin tag sequences, can be used to simplify immunological purification of the resulting recombinant polypeptide or to facilitate immunological detection in a cell or tissue sample. Fusion to the green fluorescent protein, and recombinant versions thereof which are known in the art and available commercially, may further be used to localize Antigen polypeptides within living cells and tissue.

The present invention further pertains to methods of producing the subject Antigen polypeptides. For example, a host cell transfected with a nucleic acid vector directing expression of a nucleotide sequence encoding the subject polypeptides can be cultured under appropriate conditions to allow expression of the peptide to occur. Suitable media for cell culture are well known in the art. The recombinant Antigen polypeptide can be isolated from cell culture medium, host cells, or both using techniques known in the art for purifying proteins including ion-exchange chromatography, gel filtration chromatography, ultrafiltration, electrophoresis, and immunoaffinity purification with antibodies specific for such peptide. In a preferred embodiment, the recombinant Antigen polypeptide is a fusion protein containing a domain which facilitates its purification, such as GST fusion protein.

Moreover, it will be generally appreciated that, under certain circumstances, it may be advantageous to provide homologs of one of the subject Antigen polypeptides which function in a limited capacity as one of either an Antigen agonist (mimetic) or an Antigen antagonist, in order to promote or inhibit only a subset of the biological activities of the naturally-occurring form of the protein. Thus, specific biological effects can be elicited by treatment with a homolog of limited function, and with fewer side effects relative to treatment with agonists or antagonists which are directed to all of the biological activities of naturally occurring forms of Antigen proteins.

Homologs of each of the subject Antigen proteins can be generated by mutagenesis, such as by discrete point mutation(s), or by truncation. For instance, mutation can give rise to homologs which retain substantially the same, or merely a subset, of the biological activity of the Antigen polypeptide from which it was derived. Alternatively, antagonistic forms of the protein can be generated which are able to inhibit the function of the naturally occurring form of the protein, such as by competitively binding to an Antigen receptor.

The recombinant Antigen polypeptides of the present invention also include homologs of the wildtype Antigen proteins, such as versions of those protein which are resistant to proteolytic cleavage, as for example, due to mutations which alter ubiquitination or other enzymatic targeting associated with the protein.

Antigen polypeptides may also be chemically modified to create Antigen derivatives by forming covalent or aggregate conjugates with other chemical moieties, such as glycosyl groups, lipids, phosphate, acetyl groups and the like. Covalent derivatives of Antigen proteins can be prepared by linking the chemical moieties to functional groups on amino acid sidechains of the protein or at the N-terminus or at the C-terminus of the polypeptide.

Modification of the structure of the subject Antigen polypeptides can be for such purposes as enhancing therapeutic or prophylactic efficacy, stability (e.g., ex vivo shelf life and resistance to proteolytic degradation), or post-translational modifications (e.g., to alter phosphorylation pattern of protein). Such modified peptides, when designed to retain at least one activity of the naturally-occurring form of the protein, or to produce specific antagonists thereof, are considered functional equivalents of the Antigen polypeptides described in more detail herein. Such modified peptides can be produced, for instance, by amino acid substitution, deletion, or addition. The substitutional variant may be a substituted conserved amino acid or a substituted non-conserved amino acid.

For example, it is reasonable to expect that an isolated replacement of a leucine with an isoleucine or valine, an aspartate with a glutamate, a threonine with a serine, or a similar replacement of an amino acid with a structurally related amino acid (i.e. isosteric and/or isoelectric mutations) will not have a major effect on the biological activity of the resulting molecule. Conservative replacements are those that take place within a family of amino acids that are related in their side chains. Genetically encoded amino acids can be divided into four families: (1) acidic=aspartate, glutamate; (2) basic=lysine, arginine, histidine; (3) nonpolar=alanine, valine, leucine, isoleucine, proline, phenylalanine, methionine, tryptophan; and (4) uncharged polar=glycine, asparagine, glutamine, cysteine, serine, threonine, tyrosine. In similar fashion, the amino acid repertoire can be grouped as (1) acidic=aspartate, glutamate; (2) basic=lysine, arginine histidine, (3) aliphatic=glycine, alanine, valine, leucine, isoleucine, serine, threonine, with serine and threonine optionally be grouped separately as aliphatic-hydroxyl; (4) aromatic=phenylalanine, tyrosine, tryptophan; (5) amide=asparagine, glutamine; and (6) sulfur-containing=cysteine and methionine. (see, for example, Biochemistry, $2^{nd}$ ed., Ed. by L. Stryer, W H Freeman and Co.: 1981). Whether a change in the amino acid sequence of a peptide results in a functional Antigen homolog (e.g., functional in the sense that the resulting polypeptide mimics or antagonizes the wild-type form) can be readily determined by assessing the ability of the variant peptide to produce a response in cells in a fashion similar to the wild-type protein, or competitively inhibit such a response. Polypeptides in which more than one replacement has taken place can readily be tested in the same manner.

This invention further contemplates a method for generating sets of combinatorial mutants of the subject Antigen proteins as well as truncation mutants, and is especially useful for identifying potential variant sequences (e.g., homologs). The purpose of screening such combinatorial libraries is to generate, for example, novel Antigen homologs which can act as either agonists or antagonist, or alternatively, possess novel activities all together. Thus, combinatorially-derived homologs can be generated to have an increased potency relative to a naturally occurring form of the protein.

In one embodiment, the variegated Antigen library of Antigen variants is generated by combinatorial mutagenesis at the nucleic acid level, and is encoded by a variegated gene Antigen library. For instance, a mixture of synthetic oligonucleotides can be enzymatically ligated into gene sequences such that the degenerate set of potential Antigen sequences are expressible as individual polypeptides, or alternatively, as a set of larger fusion proteins (e.g., for phage display) containing the set of Antigen sequences therein.

There are many ways by which such libraries of potential Antigen homologs can be generated from a degenerate oligonucleotide sequence. Chemical synthesis of a degenerate gene sequence can be carried out in an automatic DNA synthesizer, and the synthetic genes then ligated into an appropriate expression vector. The purpose of a degenerate set of genes is to provide, in one mixture, all of the sequences encoding the desired set of potential Antigen sequences. The synthesis of degenerate oligonucleotides is well known in the art (see for example, Narang, S A (1983) Tetrahedron 39:3; Itakura et al. (1981) Recombinant DNA, Proc $3^{rd}$ Cleveland Sympos. Macromolecules, ed. AG Walton, Amsterdam: Elsevier pp 273-289; Itakura et al. (1984) Annu. Rev. Biochem. 53:323; Itakura et al. (1984) Science 198:1056; Ike et al. (1983) Nucleic Acid Res. 11:477. Such techniques have been employed in the directed evolution of other proteins (see, for example, Scott et al. (1990) Science 249:386-390; Roberts et al. (1992) PNAS 89:2429-2433; Devlin et al. (1990) Science 249: 404-406; Cwirla et al. (1990) PNAS 87: 6378-6382; as well as U.S. Pat. Nos. 5,223,409, 5,198,346, and 5,096,815).

Likewise, a library of coding sequence fragments can be provided for an Antigen clone in order to generate a variegated population of Antigen fragments for screening and subsequent selection of bioactive fragments. A variety of techniques are known in the art for generating such, including chemical synthesis. In one embodiment, a library of coding sequence fragments can be generated by (i) treating a double stranded PCR fragment of an Antigen coding sequence with a nuclease under conditions wherein nicking occurs only about once per molecule; (ii) denaturing the double stranded DNA; (iii) renaturing the DNA to form double stranded DNA which can include sense/antisense pairs from different nicked products; (iv) removing single stranded portions from reformed duplexes by treatment with S1 nuclease; and (v) ligating the resulting fragment library into an expression vector. By this exemplary method, an expression library can be derived which codes for N-terminal, C-terminal and internal fragments of various sizes.

A wide range of techniques are known in the art for screening gene products of combinatorial libraries made by point mutations or truncation, and for screening cDNA libraries for gene products having a certain property. Such techniques will be generally adaptable for rapid screening of the gene libraries generated by the combinatorial mutagenesis of Antigen homologs. The most widely used techniques for screening large gene libraries typically comprises cloning the gene library into replicable expression vectors, transforming appropriate cells with the resulting libraries of vectors, and expressing the combinatorial genes under conditions in which detection of a desired activity facilitates relatively easy isolation of the vector encoding the gene whose product was detected. Each of the illustrative assays described below are amenable to high through-put analysis as necessary to screen large numbers of degenerate Antigen sequences created by combinatorial mutagenesis techniques. Combinatorial mutagenesis has a potential to generate very large libraries of mutant proteins, e.g., in the order of 1026 molecules. Combinatorial libraries of this size may be technically challenging to screen even with high throughput screening assays. To overcome this problem, a new technique has been developed recently, recrusive ensemble mutagenesis (REM), which allows one to avoid the very high proportion of non-functional proteins in a random library and simply enhances the frequency of functional proteins, thus decreasing the complexity required to achieve a useful sampling of sequence space. REM is an algorithm which enhances the frequency of functional mutants in a library when an appropriate selection or screening method is employed (Arkin and Yourvan, 1992, PNAS USA 89:7811-7815; Yourvan et al., 1992, Parallel Problem Solving from Nature, 2., In Maenner and Manderick, eds., Elsevir Publishing Co., Amsterdam, pp. 401-410; Delgrave et al., 1993, Protein Engineering 6(3):327-331).

The invention also provides for reduction of the Antigen proteins to generate mimetics, e.g., peptide or non-peptide agents, such as small molecules, which are able to disrupt binding of an Antigen polypeptide of the present invention with a molecule, e.g. target peptide. Thus, such mutagenic techniques as described above are also useful to map the determinants of the Antigen proteins which participate in protein-protein interactions involved in, for example, binding of the subject Antigen polypeptide to a target peptide. To illustrate, the critical residues of a subject Antigen polypeptide which are involved in molecular recognition of its receptor can be determined and used to generate Antigen derived peptidomimetics or small molecules which competitively inhibit binding of the authentic Antigen protein with that moiety. By employing, for example, scanning mutagenesis to map the amino acid residues of the subject Antigen proteins which are involved in binding other proteins, peptidomimetic compounds can be generated which mimic those residues of the Antigen protein which facilitate the interaction. Such mimetics may then be used to interfere with the normal function of an Antigen protein. For instance, non-hydrolyzable peptide analogs of such residues can be generated using benzodiazepine (e.g., see Freidinger et al. in Peptides: Chemistry and Biology, G. R. Marshall ed., ESCOM Publisher: Leiden, Netherlands, 1988), azepine (e.g., see Huffman et al. in Peptides: Chemistry and Biology, G. R. Marshall ed., ESCOM Publisher: Leiden, Netherlands, 1988), substituted gamma lactam rings (Garvey et al. in Peptides: Chemistry and Biology, G. R. Marshall ed., ESCOM Publisher: Leiden, Netherlands, 1988), keto-methylene pseudopeptides (Ewenson et al. (1986) J Med Chem 29:295; and Ewenson et al. in Peptides: Structure and Function (Proceedings of the 9th American Peptide Symposium) Pierce Chemical Co. Rockland, Ill., 1985), b-turn dipeptide cores (Nagai et al. (1985) Tetrahedron Lett 26:647; and Sato et al. (1986) J Chem Soc Perkin Trans 1:1231), and b-aminoalcohols (Gordon et al. (1985) Biochem Biophys Res Commun126:419; and Dann et al. (1986) Biochem Biophys Res Commun 134:71).

"Encoded by" refers to a nucleic acid sequence which codes for a polypeptide sequence, wherein the polypeptide sequence contains an amino acid sequence of at least 3 to 5 amino acids, more preferably at least 8 to 10 amino acids, and even more preferably at least 15 to 20 amino acids, a polypeptide encoded by the nucleic acid sequences. Also encompassed are polypeptide sequences which are immunologically identifiable with a polypeptide encoded by the sequence. Thus, an antigen "polypeptide," "protein," or "amino acid" sequence may have at least 60% similarity, preferably at least about 75% similarity, more preferably about 85% similarity, and most preferably about 95% similarity, to a polypeptide or amino acid sequence of an antigen.

A "recombinant polypeptide" or "recombinant protein" or "polypeptide produced by recombinant techniques," which are used interchangeably herein, describes a polypeptide which by virtue of its origin or manipulation is not associated with all or a portion of the polypeptide with which it is associated in nature and/or is linked to a polypeptide other than that to which it is linked in nature. A recombinant or encoded polypeptide or protein is not necessarily translated from a designated nucleic acid sequence. It also may be generated in any manner, including chemical synthesis or expression of a recombinant expression system.

The term "synthetic peptide" as used herein means a polymeric form of amino acids of any length, which may be chemically synthesized by methods well-known to the routineer. These synthetic peptides are useful in various applications.

The term "polynucleotide" as used herein means a polymeric form of nucleotides of any length, either ribonucleotides or deoxyribonucleotides. This term refers only to the primary structure of the molecule. Thus, the term includes double- and single-stranded DNA, as well as, double- and single-stranded RNA. It also includes modifications, such as methylation or capping, and unmodified forms of the polynucleotide. The terms "polynucleotide," "oligomer," "oligonucleotide," and "oligo" are used interchangeably herein.

"A sequence corresponding to a cDNA" means that the sequence contains a polynucleotide sequence that is identical to or complementary to a sequence in the designated DNA. The degree (or "percent") of identity or complementarity to the cDNA will be approximately 50% or greater, will preferably be at least about 70% or greater, and more preferably will be at least about 90%. The sequence that corresponds to the identified cDNA will be at least about 50 nucleotides in length, will preferably be about 60 nucleotides in length, and more preferably, will be at least about 70 nucleotides in length. The correspondence between the gene or gene fragment of interest and the cDNA can be determined by methods known in the art, and include, for example, a direct comparison of the sequenced material with the cDNAs described, or hybridization and digestion with single strand nucleases, followed by size determination of the digested fragments.

"Purified polynucleotide" refers to a polynucleotide of interest or fragment thereof which is essentially free, i.e., contains less than about 50%, preferably less than about 70%, and more preferably, less than about 90% of the protein with which the polynucleotide is naturally associated. Techniques for purifying polynucleotides of interest are well-known in the art and include, for example, disruption of the cell containing the polynucleotide with a chaotropic agent and separation of the polynucleotide(s) and proteins by ion-exchange chromatography, affinity chromatography and sedimentation according to density.

"Purified polypeptide" means a polypeptide of interest or fragment thereof which is essentially free, that is, contains less than about 50%, preferably less than about 70%, and more preferably, less than about 90% of cellular components with which the polypeptide of interest is naturally associated. Methods for purifying are known in the art.

The term "isolated" means that the material is removed from its original environment (e.g., the natural environment if it is naturally occurring). For example, a naturally-occurring polynucleotide or polypeptide present in a living animal is not isolated, but the same polynucleotide or DNA or polypeptide, which is separated from some or all of the coexisting materials in the natural system, is isolated. Such polynucleotide could be part of a vector and/or such polynucleotide or polypeptide could be part of a composition, and still be isolated in that the vector or composition is not part of its natural environment.

"Polypeptide" and "protein" are used interchangeably herein and indicates a molecular chain of amino acids linked through covalent and/or noncovalent bonds. The terms do not refer to a specific length of the product. Thus, peptides, oligopeptides and proteins are included within the definition of polypeptide. The terms include post-expression modifications of the polypeptide, for example, glycosylations, acetylations, phosphorylations and the like. In addition, protein fragments, analogs, mutated or variant proteins, fusion proteins and the like are included within the meaning of polypeptide.

A "fragment" of a specified polypeptide refers to an amino acid sequence which comprises at least about 3-5 amino acids, more preferably at least about 8-10 amino acids, and even more preferably at least about 15-20 amino acids, derived from the specified polypeptide.

"Recombinant host cells," "host cells," "cells," "cell lines," "cell cultures," and other such terms denoting microorganisms or higher eukaryotic cell lines cultured as unicellular entities refer to cells which can be, or have been, used as recipients for recombinant vector or other transferred DNA, and include the original progeny of the original cell which has been transfected.

As used herein "replicon" means any genetic element, such as a plasmid, a chromosome or a virus, that behaves as an autonomous unit of polynucleotide replication within a cell.

A "vector" is a replicon in which another polynucleotide segment is attached, such as to bring about the replication and/or expression of the attached segment.

The term "control sequence" refers to polynucleotide sequences which are necessary to effect the expression of coding sequences to which they are ligated. The nature of such control sequences differs depending upon the host organism. In prokaryotes, such control sequences generally include promoter, ribosomal binding site and terminators; in eukaryotes, such control sequences generally include promoters, terminators and, in some instances, enhancers. The term "control sequence" thus is intended to include at a minimum all components whose presence is necessary for expression, and also may include additional components whose presence is advantageous, for example, leader sequences.

"Operably linked" refers to a situation wherein the components described are in a relationship permitting them to function in their intended manner. Thus, for example, a control sequence "operably linked" to a coding sequence is ligated in such a manner that expression of the coding sequence is achieved under conditions compatible with the control sequences.

The term "open reading frame" or "ORF" refers to a region of a polynucleotide sequence which encodes a polypeptide; this region may represent a portion of a coding sequence or a total coding sequence.

A "coding sequence" is a polynucleotide sequence which is transcribed into mRNA and translated into a polypeptide when placed under the control of appropriate regulatory sequences. The boundaries of the coding sequence are determined by a translation start codon at the 5'-terminus and a translation stop codon at the 3'-terminus. A coding sequence can include, but is not limited to, mRNA, cDNA, and recombinant polynucleotide sequences.

The term "immunologically identifiable with/as" refers to the presence of epitope(s) and polypeptide(s) which also are present in and are unique to the designated polypeptide(s). Immunological identity may be determined by antibody binding and/or competition in binding. These techniques are known to the routineer and also are described herein. The uniqueness of an epitope also can be determined by computer searches of known data banks, such as GenBank, for the polynucleotide sequences which encode the epitope, and by amino acid sequence comparisons with other known proteins.

As used herein, "epitope" means an antigenic determinant of a polypeptide. Conceivably, an epitope can comprise three amino acids in a spatial conformation which is unique to the epitope. Generally, an epitope consists of at least five such amino acids, and more usually, it consists of at least eight to ten amino acids. Methods of examining spatial conformation are known in the art and include, for example, x-ray crystallography and two-dimensional nuclear magnetic resonance.

A "conformational epitope" is an epitope that is comprised of specific juxtaposition of amino acids in an immunologically recognizable structure, such amino acids being present on the same polypeptide in a contiguous or non-contiguous order or present on different polypeptides.

A polypeptide is "immunologically reactive" with an antibody when it binds to an antibody due to antibody recognition of a specific epitope contained within the polypeptide. Immunological reactivity may be determined by antibody binding, more particularly by the kinetics of antibody binding, and/or by competition in binding using as competitor(s) a known polypeptide(s) containing an epitope against which the antibody is directed. The methods for determining whether a polypeptide is immunologically reactive with an antibody are known in the art.

As used herein, the term "immunogenic polypeptide containing an epitope of interest" means naturally occurring polypeptides of interest or fragments thereof, as well as polypeptides prepared by other means, for example, by chemical synthesis or the expression of the polypeptide in a recombinant organism.

The term "transformation" refers to the insertion of an exogenous polynucleotide into a host cell, irrespective of the method used for the insertion. For example, direct uptake, transduction or f-mating are included. The exogenous polynucleotide may be maintained as a non-integrated vector, for example, a plasmid, or alternatively, may be integrated into the host genome.

"Treatment" refers to prophylaxis and/or therapy.

The term "individual" as used herein refers to vertebrates, particularly members of the mammalian species and includes but is not limited to domestic animals, sports animals, primates and humans; more particularly the term refers to humans.

The term "sense strand" or "plus strand" (or "+") as used herein denotes a nucleic acid that contains the sequence that encodes the polypeptide. The term "antisense strand" or "minus strand" (or "−") denotes a nucleic acid that contains a sequence that is complementary to that of the "plus" strand.

The term "test sample" refers to a component of an individual's body which is the source of the analyte (such as, antibodies of interest or antigens of interest). These components are well known in the art. These test samples include biological samples which can be tested by the methods of the present invention described herein and include human and animal body fluids such as whole blood, serum, plasma, cerebrospinal fluid, urine, lymph fluids, and various external secretions of the respiratory, intestinal and genitourinary tracts, tears, saliva, milk, white blood cells, myelomas and the like; biological fluids such as cell culture supernatants; fixed tissue specimens; and fixed cell specimens.

"Purified product" refers to a preparation of the product which has been isolated from the cellular constituents with which the product is normally associated, and from other types of cells which may be present in the sample of interest.

"PNA" denotes a "peptide nucleic acid analog" which may be utilized in a procedure such as an assay described herein to determine the presence of a target. "MA" denotes a "morpholino analog" which may be utilized in a procedure such as an assay described herein to determine the presence of a target. See, for example, U.S. Pat. No. 5,378,841, which is incorporated herein by reference. PNAs are neutrally charged moieties which can be directed against RNA targets or DNA. PNA probes used in assays in place of, for example, the DNA probes of the present invention, offer advantages not achievable when DNA probes are used. These advantages include manufacturability, large scale labeling, reproducibility, stability, insensitivity to changes in ionic strength and resistance to enzymatic degradation which is present in methods utilizing DNA or RNA. These PNAs can be labeled with such signal generating compounds as fluorescein, radionucleotides, chemiluminescent compounds, and the like. PNAs or other nucleic acid analogs such as MAs thus can be used in assay methods in place of DNA or RNA. Although assays are described herein utilizing DNA probes, it is within the scope of the routineer that PNAs or MAs can be substituted for RNA or DNA with appropriate changes if and as needed in assay reagents.

"Analyte," as used herein, is the substance to be detected which may be present in the test sample. The analyte can be any substance for which there exists a naturally occurring specific binding member (such as, an antibody), or for which a specific binding member can be prepared. Thus, an analyte is a substance that can bind to one or more specific binding members in an assay. "Analyte" also includes any antigenic substances, haptens, antibodies, and combinations thereof. As a member of a specific binding pair, the analyte can be detected by means of naturally occurring specific binding partners (pairs) such as the use of intrinsic factor protein as a member of a specific binding pair for the determination of Vitamin B12, the use of folate-binding protein to determine folic acid, or the use of a lectin as a member of a specific binding pair for the determination of a carbohydrate. The analyte can include a protein, a peptide, an amino acid, a nucleotide target, and the like.

"Inflammation" or "inflammatory disease," as used herein, refer to infiltration of activated lymphocytes such as neutrophils, eosinophils, macrophages, T cells and B-cells, into a host tissue that results in damage to the host organism. Examples of inflammatory disease include but are not limited to conditions such as inflammatory bowel disease, sepsis, and rheumatoid arthritis.

An "Expressed Sequence Tag" or "EST" refers to the partial sequence of a cDNA insert which has been made by reverse transcription of mRNA extracted from a tissue, followed by insertion into a vector.

A "transcript image" refers to a table or list giving the quantitative distribution of ESTs in a library and represents the genes active in the tissue from which the library was made.

The present invention provides assays which utilize specific binding members. A "specific binding member," as used herein, is a member of a specific binding pair. That is, two different molecules where one of the molecules through chemical or physical means specifically binds to the second molecule. Therefore, in addition to antigen and antibody specific binding pairs of common immunoassays, other specific binding pairs can include biotin and avidin, carbohydrates and lectins, complementary nucleotide sequences, effector and receptor molecules, cofactors and enzymes, enzyme inhibitors and enzymes, and the like. Furthermore, specific binding pairs can include members that are analogs of the original specific binding members, for example, an analyte-analog. Immunoreactive specific binding members include antigens, antigen fragments, antibodies and antibody fragments, both monoclonal and polyclonal, and complexes thereof, including those formed by recombinant DNA molecules.

The term "hapten," as used herein, refers to a partial antigen or non-protein binding member which is capable of binding to an antibody, but which is not capable of eliciting antibody formation unless coupled to a carrier protein.

A "capture reagent," as used herein, refers to an unlabeled specific binding member which is specific either for the analyte as in a sandwich assay, for the indicator reagent or analyte as in a competitive assay, or for an ancillary specific binding member, which itself is specific for the analyte, as in an indirect assay. The capture reagent can be directly or indirectly bound to a solid phase material before the performance of the assay or during the performance of the assay, thereby enabling the separation of immobilized complexes from the test sample.

The "indicator reagent" comprises a "signal-generating compound" ("label") which is capable of generating and generates a measurable signal detectable by external means, conjugated ("attached") to a specific binding member. "Specific binding member" as used herein means a member of a specific binding pair. That is, two different molecules where one of the molecules through chemical or physical means specifically binds to the second molecule. In addition to being an antibody member of a specific binding pair, the indicator reagent also can be a member of any specific binding pair, including either hapten-anti-hapten systems such as biotin or anti-biotin, avidin or biotin, a carbohydrate or a lectin, a complementary nucleotide sequence, an effector or a receptor molecule, an enzyme cofactor and an enzyme, an enzyme inhibitor or an enzyme, and the like. An immunoreactive specific binding member can be an antibody, an antigen, or an antibody/antigen complex that is capable of binding either to polypeptide of interest as in a sandwich assay, to the capture reagent as in a competitive assay, or to the ancillary specific binding member as in an indirect assay. When describing probes and probe assays, the term "reporter molecule" may be used. A reporter molecule comprises a signal generating compound as described hereinabove conjugated to a specific binding member of a specific binding pair, such as carbazol or adamantane.

4.6 Stem Cell Preparation and Manipulation

Methods for isolating and manipulating bone marrow cells, including hematopoietic stem cells, from a bone marrow graft donor are known in the art. For example, U.S. Patent Nos. 4,965,204, 5,035,994, 5,081,030, 5,130,144, 5,137,809, 6,068,836 and 6,200,606, the contents of which patents are hereby incorporated by reference, describe methods for obtaining and manipulating bone marrow stem cells from a mammalian bone marrow donor. One of the most useful differentiation antigens for isolating human hematopoietic systems is the cell surface antigen known as CD34. CD34 is expressed by about 1% to 5% of normal human adult marrow cells in a developmentally, stage-specific manner (CI Civin et al., "Antigenic analysis of hematopoiesis. A hematopoietic progenitor cell surface antigen defined by a monoclonal antibody raised against KG-1a cells" J.Immunol., 133, 157-165, 1984). CD34+ cells are a mixture of immature blastic cells and a small percentage of mature, lineage-committed cells of the myeloid, erythroid and lymphoid series. Perhaps 1% of CD34+ cells are true hematopoietic stem cells (HSC) with the remaining number being committed to a particular lineage. Results in humans have demonstrated that CD34+ cells isolated from peripheral blood or marrow can reconstitute the entire hematopoietic system for a lifetime. Therefore, CD34 is a marker for HSC and hematopoietic progenitor cells.

For example, selective cytapheresis can be used to produce a cell suspension from human bone marrow or blood containing pluripotent lymphohematopoeitic stem cells. For example, marrow can be harvested from a donor (the patient in the case of an autologous transplant; a donor in the case of an allogenic transplant) by any appropriate means. The marrow can be processed as desired, depending mainly upon the use intended for the recovered cells. The suspension of marrow cells is allowed to physically contact, for example, a solid phase-linked monoclonal antibody that recognizes an antigen on the desired cells. The solid phase-linking can comprise, for instance, adsorbing the antibodies to a plastic, nitrocellulose or other surface. The antibodies can also be adsorbed on to the walls of the large pores (sufficiently large to permit flow-through of cells) of a hollow fiber membrane. Alternatively, the antibodies can be covalently linked to a surface or bead, such as Pharmacia Sepharose 6 MB macrobeads.RTM. The exact conditions and duration of incubation for the solid phase-linked antibodies with the marrow cell suspension will depend upon several factors specific to the system employed. The selection of appropriate conditions, however, is well within the skill of the art.

The unbound cells are then eluted or washed away with physiologic buffer after allowing sufficient time for the stem cells to be bound. The unbound marrow cells can be recovered and used for other purposes or discarded after appropriate testing has been done to ensure that the desired separation had been achieved. The bound cells are then separated from the solid phase by any appropriate method, depending mainly upon the nature of the solid phase and the antibody. For example, bound cells can be eluted from a plastic petrie dish by vigorous agitation. Alternatively, bound cells can be eluted by enzymatically "nicking" or digesting a enzyme-sensitive "spacer" sequence between the solid phase and the antibody. Spacers bound to agarose beads are commercially available from, for example, Pharmacia.

The eluted, enriched fraction of cells may then be washed with a buffer by centrifugation and either cryopreserved in a viable state for later use according to conventional technology or immediately infused intravenously into the transplant recipient.

In a particularly preferred embodiment, stem cells can be recovered directly from blood using essentially the above methodology. For example, blood can be withdrawn directly from the circulatory system of a donor and percolated continuously through a device (e.g., a column) containing the solid phase-linked monoclonal antibody to stem cells and the stem cell-depleted blood can be returned immediately to the donor's circulatory system using, for example, a conventional hemapheresis machine. When a sufficient volume of blood has been processed to allow the desired number of stem cells to bind to the column, the patient is disconnected. Such a method is extremely desirable because it allows rare peripheral blood stem cells to be harvested from a very large volume of blood, sparing the donor the expense and pain of harvesting bone marrow and the associated risks of anesthesia, analgesia, blood transfusion, and infection. The duration of aplasia for the transplant recipient following the marrow transplant can also be shortened since, theoretically, unlimited numbers of blood stem cells could be collected without significant risk to the donor.

The above methods of treating marrow or blood cell suspensions produce a suspension of human cells that contains pluripotent lympho-hematopoietic stem cells, but substantially free of mature lymphoid and myeloid cells. The cell suspension also contains substantially only cells that express the My-10 antigen and can restore the production of lymphoid and hematopoietic cells to a human patient that has lost the ability to produce such cells because of, for example, radiation treatment. By definition, a cell population that can restore the production of hematopoietic and lymphoid cells contains pluripotent lympho-hematopoietic stem cells.

The above cell populations containing human pluripotent lympho-hematopoetic stem cells can be used in therapeutic methods such as stem cell transplantation as well as others that are readily apparent to those of skill in the art. For example, such cell populations can be administered directly by I.V. to a patient requiring a bone marrow transplant in an amount sufficient to reconstitute the patient's hematopoietic and immune system. Precise, effective quantities can be readily determined by those skilled in the art and will depend, of course, upon the exact condition being treated by the therapy. In many applications, however, an amount containing approximately the same number of stem cells found in one-half to one liter of aspirated marrow should be adequate.

4.7. Dendritic Cell Preparation and Manipulation

Methods for isolating and manipulating dendritic cells, including dendritic antigen presenting cells from a bone marrow graft sample or from peripheral blood of a donor animal are known in the art. For example, U.S. Pat. Nos. 6,165,785 and 6,194,204, the contents of which patents are hereby incorporated by reference, describe methods for obtaining and manipulating dendritic (antigen-presenting) cells from a mammalian bone marrow donor.

One exemplary method for the enrichment of dendritic cells from the peripheral blood of a mammal utilizes the following steps. The mononuclear cells are separated from the peripheral blood. The mononuclear cells are separated into a first cell population having substantially lymphocytes and a second cell population having substantially myeloid cells. The myeloid cells are separated into a third cell population having substantially monocytes and a fourth cell population having substantially dendritic cells.

By peripheral blood is meant blood found in the circulation vasculature. The peripheral blood can be obtained from any mammal. By mammal is meant human as well as non-human mammal. Preferred non-human mammals is a mouse or a pig. Preferably, the peripheral blood is obtained from the same source from which the donor stem cell graft, e.g. the hematopoietic stem cell graft, is obtained. The mononuclear cells can be separated from the peripheral blood by any method known to those skilled in the art. Preferably, the method used does not affect cell function or viability. A preferred method is the use of centrifugation, preferably density gradient centrifugation, preferably discontinuous density gradient centrifugation. An alternative is the use of specific monoclonal antibodies.

The mononuclear cells are separated into a first cell population having substantially lymphocytes and a second cell population having substantially myeloid cells. Lymphocytes are meant to include, e.g., T cells, NK cells, B cells and mixtures thereof. By a cell population having substantially lymphocytes is meant that the cell population has greater than about 20% lymphocytes, preferably greater than about 40% lymphocytes, more preferably greater than about 60% lymphocytes, more preferably yet greater than about 80% lymphocytes, more preferably yet greater than about 90% lymphocytes, more preferably yet greater than about 95% lymphocytes, more preferably yet greater than about 98% lymphocytes, and most preferably greater than about 99% lymphocytes. Myeloid cells are meant to include monocytes and dendritic cells. Monocytes are also meant to include macrophages. It is known that monocytes circulate in the peripheral blood, and when they migrate to the tissue, they are called macrophages. This lineage of cells are commonly called monocyte/macrophage lineage. Myeloid cells are generally $CD14^+$, $CD33^+$ and $CD13^+$. By a cell population having substantially myeloid cells is meant that the cell population has greater than about 20% myeloid cells, preferably greater than about 40% myeloid cells, more preferably greater than about 60% myeloid cells, more preferably yet greater than about 80% myeloid cells, more preferably yet greater than about 90% myeloid cells, more preferably yet greater than about 95% myeloid cells, more preferably yet greater than about 98% myeloid cells, and most preferably greater than about 99% myeloid cells.

In certain embodiments, the separation of the mononuclear cells into a first cell population having substantially lymphocytes and a second cell population having substantially myeloid cells comprises contacting the mononuclear cells with antibodies against the lymphocytes so as to form an antibody-lymphocyte complex, and selectively separating the antibody-lymphocyte complex from the myeloid cells. One or more than one type of antibody can be used. In certain embodiments, the contacting and the selectively separating steps are repeated. These steps can be repeated using the same type of antibody or antibodies against the lymphocytes, or they can be repeated using a different type of antibody or antibodies against the lymphocytes.

Both polyclonal and monoclonal antibodies can be used in this invention. Preferably, monoclonal antibodies are used. Antibodies against the lymphocytes include, e.g., T cell antibodies, NK cell antibodies, B cell antibodies, or mixtures thereof. Preferably, mixtures of the antibodies are used. The antibodies used are directed against one or more antigens which are expressed by one or more of the lymphocytes.

Preferably, the T cell antibodies are anti-CD3 antibodies. All T cells express the CD3 surface molecule. CD3 is described in Barclay et al., The Leukocyte Antigen Facts Book, Academic Press Limited (1993), pp. 106-109. Anti-CD3 antibodies can be obtained from Becton Dickinson Immunocytometry Systems, San Jose, Calif. or Coulter Corp., Miami, Fla. Other T cell antibodies that can be used include, e.g., anti-CD8 antibodies. CD8 is described in Barclay et al., The Leukocyte Antigen Facts Book, Academic Press Limited (1993), pp. 118-119. Anti-CD8 antibodies can be obtained from Becton Dickinson Immunocytometry Systems or Coulter Corp. Not all T cells express CD8. CD8 is expressed by roughly 40% of the T-lymphocyte population. Therefore, using, e.g., anti-CD8 antibodies will generally not result in the separation of the entire T cell population from the myeloid cells. There are, however, certain situations in which it might be desirable to use anti-CD8 antibodies. For example, $CD8^+$ T lymphocytes represent a cytotoxic T-lymphocyte population. This population selectively targets and kills cells which were exposed to pathogen-specific antigens used in the production of pathogen-specific cytotoxic T cell lysis (intracellular pathogens).

Preferably, the NK cell antibodies are anti-CD16/56. CD 16/56 refers to CD16 and CD56; they are not the same antigen, but are both expressed by NK cells. ($CD8^+$ T lymphocytes also express CD 16). Anti-CD 16/56 antibodies can be obtained from Becton Dickinson Immunocytometry Systems or Coulter Corp. In certain embodiments, the NK cell antibodies can be anti-CD8. Not all NK cells express CD8, and therefore using anti-CD8 antibodies will not result in the separation of the entire NK cell population from the myeloid cells.

Preferably, the B cell antibodies are anti-CD19 or anti-CD20 antibodies. CD19 and CD20 are expressed by resting and activated B lymphocytes. CD19 and CD20 are described in Barclay et al., The Leukocyte Antigen Facts Book, Academic Press Limited (1993), pp. 142-143 and 144-145, respectively. Anti-CD19 and anti-CD20 antibodies can be obtained from Becton Dickinson Immunocytometry Systems or Coulter Corp.

The antibody-lymphocyte complex that is formed is selectively separated from the myeloid cells. In certain embodiments, this separation comprises contacting the antibody-lymphocyte complex and the myeloid cells with a matrix such that the antibody-lymphocyte complex is substantially retained by the matrix and the myeloid cells are substantially not retained by the matrix. Any matrix which performs such a separation can be used.

A matrix which is particularly useful is a mesh of steel wool which is inserted into a plastic column and placed in a magnetic field. A cell magnetic bead complex passes into the matrix and remains in the matrix as long as the column stays within the magnetic field. Examples of matrices include depletion columns type BS, type CS, type D RS+, and MS+ used for Mini Mags separator. (All these columns can be obtained from Miltenyi Biotec, Auburn, Calif.) Preferably, the matrix is provided in a column, though the matrix can be provided in any other way known to those skilled in the art, e.g., in a gel, on a filter, on a plate, on film or on paper.

By the complex being substantially retained by the matrix is meant that greater than about 20% of the complex is retained, preferably greater than about 40% is retained, more preferably greater than about 60% is retained, more preferably yet greater than about 80% is retained, more preferably yet greater than about 90% is retained, more preferably yet greater than about 95% is retained, and most preferably greater than about 98% is retained. By the myeloid cells being substantially not retained by the matrix is meant that greater than about 20% of the myeloid cells are not retained, preferably greater than about 40% are not retained, more preferably greater than about 60% are not retained, more preferably yet greater than about 80% are not retained, more preferably yet greater than about 90% are not retained, more preferably yet greater than about 95% are not retained, and most preferably greater than about 98% are not retained.

In preferred embodiments, the antibody-lymphocyte complex further comprises magnetic beads. Preferably, the magnetic beads are superparamagnetic microparticles, though any type of magnetic bead can be used. The magnetic beads can be attached, e.g., to the antibody or to the lymphocyte or to both. Preferably, the magnetic beads are attached to the antibody. Such attached antibodies can be obtained, e.g., from Miltenyi Biotec, Auburn, Calif. (as MACS superparamagnetic microbeads conjugated with monoclonal antibodies), or from Dynal Corp., Lake Success, N.Y. (as detachable or non-detachable large magnetic beads). See also Miltenyi et al., Cytometry 11:231-238 (1990). Preferably, the large magnetic beads (obtainable from Dynal Corp.), are used for the removal of lymphocytes. Preferably, the smaller beads (obtainable from Miltenyi Biotec), are used for the enrichment of the dendritic cells described below. The magnetic beads can be attached prior to the formation of the antibody-lymphocyte complex, or subsequent to the formation of the complex. Preferably, the magnetic beads are attached prior to formation of the complex.

In embodiments in which the antibody-lymphocyte complex has magnetic beads, separation of such a complex from the myeloid cells preferably comprises contacting the myeloid cells and the complex with a magnetic matrix such that the antibody-lymphocyte complex having the magnetic beads is substantially retained by the magnetic matrix and the myeloid cells are substantially not retained by the magnetic matrix. An example of a magnetic matrix is magnetized steel wool. Steel wool can be obtained from Miltenyi Biotec. The steel wool can be magnetized by, e.g., introducing it into a magnetic field, e.g., 0.6 Tesla, though other strength magnetic fields can also be used as known to those skilled in the art. The magnetic field can be produced, e.g., with a commercial electromagnet.

In certain embodiments, the antibodies to the T cells, NK cells and B cells are all contacted with the mononuclear cells prior to selectively separating the resulting antibody-lymphocyte complexes from the myeloid cells. In other embodiments, antibodies to only one type of lymphocyte cell are added (e.g., T cells), and the resulting antibody-lymphocyte complex is separated from the remaining cells. Antibodies to one of the remaining types of lymphocytes (e.g., NK cells) are then added to the remaining cells from above, and the resulting antibody-lymphocyte complex is separated from these remaining cells. Finally, antibodies to the remaining type of lymphocyte (e.g., B cells) are then added to this second batch of remaining cells, and the resulting antibody-lymphocyte complex is separated from these remaining cells (predominantly the myeloid cells). Preferably, all of the antibodies are added prior to selective separation.

The invention also includes embodiments in which separation of the mononuclear cells into a first cell population having substantially lymphocytes and a second cell population having substantially myeloid cells, comprises centrifugation. The centrifugation can be, e.g., density gradient centrifugation. For example, metrizamide 14.5% (obtained from Sigma Chemical Co., St. Louis, Mo.) or Monocyte 1 step (which is a pre-made discontinuous gradient which separates lymphocytes from myeloid cells, obtained from Accurate Chemical and Scientific Corp., Westbury, N.Y.), can be used. Centrifugation procedures are most useful if there are initially a large number of PBMCs, e.g., about $10^9$.

In certain embodiments, the separation of the mononuclear cells into a third cell population having substantially monocytes and a fourth cell population having substantially dendritic cells comprises contacting the myeloid cells with antibodies against the dendritic cells so as to form an antibody-dendritic cell complex, and selectively separating the antibody-dendritic cell complex from the monocytes. In certain embodiments, the contacting and the selectively separating steps are repeated. These steps can be repeated using the same type of antibody or antibodies against the dendritic cells, or they can be repeated using a different type of antibody or antibodies against the dendritic cells.

Preferably, monoclonal antibodies are used. The antibodies used are directed against one or more antigens which are expressed by the dendritic cells. Preferably, the antibodies are anti-CD2 antibodies, anti-CD5 antibodies, or mixtures thereof. Most preferably, anti-CD2 antibodies are used because they stain greater than 95% of the dendritic cells and do not modulate down in culture. Mixtures of the antibodies can also be used. CD2 and CD5 are described in Barclay et al., The Leukocyte Antigen Facts Book, Academic Press Limited (1993), pp. 104-105 and 112-113, respectively. Anti-CD2 antibodies can be obtained from Coulter Corp. Anti-CD5 antibodies can be obtained from Becton Dickinson Immunocytometry Systems or Coulter Corp.

The CD2 antigen is a 50 kD molecular weight glycoprotein that was initially identified on T cells and NK cells and has now been shown to be expressed by circulating dendritic cells. Antibodies to this surface antigen react strongly with resting T cells. The CD2 surface antigen is divided into three regions reflecting their functional relationship. The first region, $T11.sub.1$, is responsible for adhesion with the LFA-3 molecule and sheep erythrocyte binding. The first antibody that was produced to this region is called $T11.sub.1$ and its clone designation is 3PTH29. The second region, $T11.sub.2$, is an area on the CD2 antigen which does not interact with the binding domain but has been demonstrated to play a role in T cell activation in conjunction with a second antibody. The first antibody that was produced to this region is called $T11.sub.2$ and its clone designation is 1OLD24C1. Other $T11.sub.2$ clones are UMCD2/1E7E8, 0275, 9.6 and 7E10. The crosslinking of the $T11.sub.2$ region with monoclonal antibodies induces unfolding of the CD2 antigen and exposure of a cryptic epitope. This cryptic epitope represents a third region, T11.sub.3 or CD2R, and is expressed by activated T cells and cell-lines but only after exposure to T11.sub.2 monoclonal antibodies (or others with similar traits), which induces a conformational change in structure of the CD2 antigen. The first antibody to this region was T11.sub.3 and its clone name is 1 mono2A6. Other In certain embodiments, prior to contacting the myeloid cells with antibodies, the myeloid cells are cultured, preferably for about 12 hours to about 36 hours, in about 5% to about 10% pooled mammal specific serum. For example, pooled human serum is used if the isolation is from human peripheral blood, and pooled pig serum is used if the isolation is from pig peripheral blood. After such culturing, antibodies, preferably anti-CD83 antibodies, can be used so as to form an antibody-dendritic cell complex. (CD83 is described in Zhou et al., J. Immunol. 154: 3821-3835 (1995); Crawford et al., Blood 80(10) Suppl. 1:192a (1992)). Anti-CD83 antibodies can be isolated as described in Zhou et al., J. Immunol. 149: 735 (1992). The dendritic cells that are isolated in this embodiment can be phenotypically CD14.sup.-.

The antibody-dendritic cell complex that is formed, e.g., as a result of using any of the antibodies described above, is selectively separated from the monocytes. In certain embodiments, the separation comprises contacting the antibody-dendritic cell complex and the monocytes with a matrix such that the antibody-dendritic cell complex is substantially retained by the matrix and the monocytes are substantially not retained by the matrix. Preferably, the retained antibody-dendritic cell complex is then eluted from the matrix.

In preferred embodiments, the antibody-dendritic cell complex further comprises magnetic beads, as described above. In such embodiments, separation of the antibody-dendritic complex from the monocytes preferably comprises contacting the monocytes and antibody-dendritic cell complex having the magnetic beads with a magnetic matrix such that the antibody-dendritic cell complex having the magnetic beads is substantially retained by the magnetic matrix and the monocytes are substantially not retained by the magnetic matrix. Preferably, the retained antibody-dendritic cell complex is then eluted from the matrix. The complex can be eluted, e.g., by demagnetizing the matrix, e.g., by removing the matrix from the magnetic field.

Preferably, the dendritic cells in the fourth cell population are greater than about 60% pure, more preferably greater than about 70% pure, more preferably yet greater than about 80% pure, more preferably yet greater than about 90% pure, more preferably yet greater than about 95% pure, more preferably yet greater than about 98% pure, and most preferably greater than about 99% pure. In certain embodiments, the dendritic cells in the fourth cell population are substantially unactivated. In certain embodiments, the above method further comprises the step of activating the dendritic cells in the fourth cell population, comprising culturing the dendritic cells with T11.sub.3 antibodies or LFA-3 ligand.

Preferably, the monocytes in the third cell population are greater than about 70% pure, more preferably greater than about 80% pure, more preferably yet greater than about 90% pure, more preferably yet greater than about 95% pure, more preferably yet greater than about 98% pure, and most preferably greater than about 99% pure. Preferably, the monocytes in the third cell population are substantially unactivated. An advantage of the present invention is that it can produce monocytes which are unactivated. Other monocyte isolation procedures which use plastic adherence are known to rapidly induce monocyte activation. See Triglia et al., Blood 65(4): 921-928 (1985).

The invention also includes a method for the enrichment of dendritic cells from the peripheral blood of a mammal comprising selecting cells from the peripheral blood which do not express antigens CD3, CD16/56 and CD19 or CD20, and which do express antigen CD2, CD5, CD83, or mixtures thereof. Preferably, cells are selected which also express antigen CD14. In certain embodiments, cells are selected which do not express antigen CD14.

The invention also includes a method for the enrichment of dendritic cells from tissue of a mammal. Tissue having mononuclear cells from a mammal is provided. The mononuclear cells are separated from the tissue. The mononuclear cells are separated into a first cell population having substantially lymphocytes and a second cell population having substantially myeloid cells. The myeloid cells are separated into a third cell population having substantially monocytes and a fourth cell population having substantially dendritic cells. The tissue can be from any part of the body of the mammal that has dendritic cells, e.g., skin or lymph nodes.

5. EXAMPLES

The examples below provide guidance to the skilled artisan in applying the methods and compositions of the invention for modulation of systemic immune responses in a host organism by transplantation of hematopoietic stem cells transduced with genes encoding antigens and antigen presenting cell regulatory molecules. The approach takes advantage of bone marrow transplantation and hematopoietic stem cell transplantation which is currently routinely utilized clinically. The invention applies the capacity of modern vectors to transduce hematopoietic stem cells or bone marrow cells ex vivo prior to their transplant. This procedures utilized are in keeping with standard bone marrow manipulations that are currently utilized routinely. An additional element to this approach involves the infusion of either autologous or allogeneic mature lymphocytes subsequent to the bone marrow transplant. Again, this approach is routinely performed clinically. The following examples provide guidance in establishing a population of antigen expressing cells in a host organism using appropriate vectors such as those described as well as those which may be adapted from these exemplary vectors. Accordingly, these examples provide guidance in developing various applications of the invention including DNA vaccines directed against pathogens and tumor antigens as well as in the development of treatments for autoimmune disease and for the establishment of antigen tolerance.

Example 1

Approach to Efficient Recombinant Antigen Expression

Effective induction of systemic anti-tumor immunity requires optimal tumor antigen presentation by major histocompatibility complex (MHC) molecules simultaneously with appropriate costimulatory signals. Pardoll, D. M. (1998), *Nat. Med* 4:525; Herlyn, D. and Birebent, B. (1999), *Ann. Med.* 31:66; Banchereau, J. and Steinman, R. M. (1998), *Nature* 392:245; and Hart, D. N. J. (1997), *Blood* 90:3245. Many therapeutic and preventive tumor vaccination approaches have focused on engineering APCs, particularly DCs. While DC-based vaccines are now popular, recent studies using ex vivo antigen-loaded DC as cancer vaccines have shown limited success. This appears to be due, in part, to inefficient numbers of ex vivo differentiated DCs that home to relevant lymphoid compartments, thereby limiting their access to T cells. DNA vaccines are relatively inefficient in transducing DCs in vivo, as demonstrated by the paucity of transduced DCs found in lymph nodes draining vaccine sites. These factors ultimately limit the stimulation of antigen-specific T cells by DC.

To overcome these hurdles, we will employ a different approach to allow efficient tumor antigen presentation by functional DCs matured in vivo. Because ex vivo cultured and transduced HSC can home to bone marrow (BM) and reconstitute the lymphohematopoietic system, we propose that HSC transduced ex vivo with a specific tumor Ag gene can generate large numbers of DC that differentiate in vivo and then express the tumor Ag. This approach provides the potential to express relevant antigens in great numbers of DCs within the body rather than the relatively tiny number accessed by standard vaccines. We will present preliminary data that this approach indeed results in enhanced activation of antigen-specific T cells transferred into the transplanted animals. For this HSC-based approach, transgene expression is further controlled by an improved lentiviral vector (LV) allowing selective expression of the transgene in DCs derived from the transduced HSC. Together with the application of various specific promoters driving the transgene, this HSC-based transduction approach also allows us to examine the in vivo immunoregulatory functions of different DC subsets. Herlyn, D. and Birebent, B. (1999), *Ann. Med.* 31:66; Banchereau, J. and Steinman, R. M. (1998), *Nature* 392:245; and Hart, D. N. J. (1997), *Blood* 90:3245. Importantly, the success of our approach does not rely on high efficiency transduction of the most primitive HSC. Generation of Ag-expressing DCs from transduced multipotent progenitors may be sufficient to immunize the organism. Indeed, the high transduction efficiencies of engrafting human and mouse HSC that we demonstrate below indicate that HSC transduction efficiency is unlikely to be the rate-limiting step. We will compare these in vivo and ex vivo differentiated, Ag-expressing DCs in their functional capacity to prime anticancer immune responses and ultimately to reverse immune tolerance to these tumor antigens, which represents the major barrier to effective cancer immunotherapy.

Example 2

HSC Gene transduction by LV and Oncoretroviral Vectors (RV)

With improved methods for HSC culture and virus production, we can now transduce human HSC, assayed as SCID-repopulating cells (SRC) in NOD/SCID mice, using RV or LV. These methods are described in: Cheng, L. et al. (1997), *Gene Therapy* 4:1013; Cheng, L. et al. (1998), *Blood* 92:83; Novelli, E. et al. (1999), *Human Gene Therapy* 10:2927; Gao, Z. et al. (2000), *Molecular Therapy* 1:35S; Gao, Z. et al. (2001), Stem Cells, in press; and Cui, Y. et al. (2000), *Exp. Hematology* 27:62a, the contents of which are incorporated by reference. Recently we have made a direct comparison of MSCV-based RV with HIV-based LV for SRC gene transduction. These (see Gao, Z. et al. (2000), *Molecular Therapy* 1:35S; and Gao, Z. et al. (2001), Stem Cells, in press) and other data demonstrate that LV require less ex vivo manipulations and are more efficient to transduce human HSC than RV.

EXAMPLE 3

Stable and Targeted Transgene Expression Mediated by LV

It has generally been difficult to construct high-titer RV whose transgenes are solely under the control of a non-viral (internal) promoter. Recently it was demonstrated that specific transgene expression controlled by an internally-built specific promoter is more readily achieved using LV with self-inactivating modification; Cui, Y. et al. (1999), *J Virology* 73:6171; and Zufferey, R. et al. (1998), *J. Virol.* 72:9873; which disables the basal promoter function of the LV LTR post integration (FIG. 1). Since this project depends in part on generating DC-specific gene expression, the superiority of LV to RV in this regard further validates LV as the vector of choice. We began by using a SIN vector (EF.GFP) in which transgene expression (GFP) is controlled by the promoter of a human housekeeping gene, EF1a (FIG. 2A). To further examine the feasibility of selective transgene expression in APCs, we made the DR.GFP vector. In this LV, the human EF1a promoter was replaced by the human HLA-DR☐ (MHC class II) promoter, whose gene is expressed selectively in APCs and highly in mature, activated DCs. In subsequent experiments, we evaluated the performance of SIN vectors driving the GFP reporter in DCs differentiated in vitro and in vivo from transduce human CD34(+) cells and mouse BM cells.

EXAMPLE 4

Preferential Transgene Expression of the DR. GFP Vector in Human MHC II$^+$ Cells Differentiated from LV-transduced Human CD34$^+$ cells After 1-2 rounds of transduction with DR.GFP or EF.GFP LV, transduced human cord or adult blood CD34$^+$ cells were cultured for 7 days with GM-CSF/IL-4/TNFa under conditions favoring DC differentiation (FIG. 3A). Alternatively, transduced cells were cultured for 14 days in Epo/G-CSF/GM-CSF/SCF/IL-3/IL-6 to induce erythroid/myeloid differentiation (FIG. 3B). Cells were harvested and analyzed for GFP transgene expression and cell-surface HLA-DR expression. FIG. 3 demonstrates the strong promoter specificity of transgene expression under both differentiation conditions. While GFP expression is observed in roughly equal proportions in DR$^+$ and DR$^-$ progeny of CD34$^+$ cells transduced with the EF.GFP vector, GFP expression in the progeny of CD34$^+$ cells transduced with the DR promoter-driven lentiviral vector (DR.GFP) is limited to the DR$^+$ cell subset (FIG. 3B). Both vectors expressed highly in DR$^+$ cells after DC differentiation (FIG. 3A).

EXAMPLE 5

Transduced Human CD34$^+$ Cells can Engraft In Vivo and Generate Multiple-Lineages of GFP+Cells Including DC that are Functional in Stimulating T Cell Proliferation We next examined the DR-mediated transgene expression in human cells derived from transduced CD34$^+$ cells post BMT in NOD/SCID mice. 10 weeks post transplantation with transduced CD34+ cells, human progeny residing in the BM and spleen of transplanted mice were analyzed for the presence of human (CD45+) cells (FIG. 4A). Gated human cells were further analyzed for GFP, CD34 and MHC II expression (FIG. 4B). We observed that ~30% of human cells in BM retained the CD34+ phenotype and the majority of human cells displayed MHC II. In this experiment, ≧50% of the CD34+ or DR+ human cells expressed GFP in each engrafted mouse with DR.GFP-transduced cells (FIG. 4B). For EF.GFP-transduced cells, GFP expression was observed in all the distinct human cell populations including human CD34+, DR+, CD19+ (B lymphoid) and CD13+/CD33+ (myeloid) cells (data not shown). These results demonstrated that multipotent, engrafting HSC have been transduced. We further examined transgene expression in progeny derived from engrafted human cells that were capable of differentiating into mature DCs (FIG. 4C). The DCs derived from progenies of DR.GFP-transduced CD34+ cells indeed expressed high levels of GFP, indicating their capacity for mediating gene expression selectively in DCs. These differentiated DCs from engrafted human progenitors can potently stimulate the proliferation of allogeneic blood lymphocytes.

Example 6

DR. GFP Vector Selectively Expresses a Transgene in MHC II+ Mouse DC Differentiated from Lentiviral Transduced Mouse BM Cells The human DR alpha promoter in the DR.GFP vector was also found selectively-expressed in mouse MHC II+ cells (data not shown). The confirmed selective transgene expression of the DR.GFP vector allowed us to use the same vector for both human and mouse cells. We used these LV to transduce BM cells freshly isolated from normal BALB/c mice. After 1-2 rounds of transduction, cells were cultured with GM-CSF to allow DC differentiation. At day 8 post DC differentiation, DC-enriched cell populations were analyzed by FACS for the expression of GFP transgene and the I-$E^d$ (MHC II) marker on the cell surface (FIG. 5). Over 17% of cells were transduced (GFP+) by either vector. In cells transduced by DR.GFP, GFP expression was selectively observed in MHC II+ cells. Thus, we confirmed the specificity of the DRalpha promoter-mediated transgene expression in MHC II+ cells.

EXAMPLE 7

Transduced Mouse BM HSC can Engraft Post BMT, and Generate GFP+ DC

In order to set up a murine system to study the in vivo immunologic effects of transduced HSC, we performed syngeneic transplantation in lethally irradiated BALB/c mice using DR.GFP- or EF.GFP-transduced mouse BM cells. At 10 weeks, BM and spleen cells were harvested, analyzed and further cultured in GM-CSF to allow DC differentiation and maturation. Cells displayed a DC phenotype (FIG. 6A), and were further analyzed for GFP expression vs the MHC II marker (FIGS. 6B and C). GFP expression by the DR.GFP vector was almost exclusively seen in the cells expressing the highest level of surface MHC II.

EXAMPLE 8

HA-Transduced HSC Post BMT Stimulate Massive Expansion of HA-Specific CD4+ T Cells Following Adoptive Transfer into Recipient Mice Having demonstrated the efficient transduction of both human and murine HSC as well as significant expression of a marker transgene in the HSC progeny subsequent to transplantation, we proceeded to evaluate the capacity of this strategy to activate antigen-specific T cells. For these studies, we utilized HA as a model antigen because it is well characterized and because we can follow HA-specific T cell responses through the use of marked anti-HA TCR transgenic CD4 and CD8 cells (see above for more details). For these experiments, HA-expressing LV were constructed by replacing the GFP gene with the HA gene (DR.HA and EF.HA, FIG. 2). Prior to performing in vivo studies, we confirmed the ability of these vectors to express functional HA in DCs cultured in vitro from BM in GM-CSF cultures. FIG. 7 demonstrates that BM-derived DCs transduced with HA-expressing LV can greatly stimulate the proliferation of HA-specific T cells in vitro. Similar stimulation was obtained when either EF.HA or DR.HA were used (data not shown).

We then proceeded to test the capacity of DC derived from transplanted HA transduced HSC to stimulate HA specific T cells in vivo. BALB/c mouse BM cells were transduced with GFP- or HA-expressing LV. Three weeks after reconstituting irradiated BALB/c recipients with the transduced HSC, animals were treated systemically with Flt3 ligand (FL) for 10 days in order to initiate in vivo DC expansion and differentiation. Eight days after initiation of in vivo FL treatment, 2 million 6.5 T cells (anti-HA CD4 TCR-Tg line) were transferred iv. Activation of HA-specific T cells in vivo was monitored both physically and functionally. In a typical transfer experiment (no BMT or FL treatment), 6.5 T cells represent a tiny proportion of the total peripheral T cells (~0.1%). Expansion of 6.5 T cells in vivo after transfer into mice that had received HA-LV transduced HSC was analyzed by double staining for CD4 and 6.5 clonotype at 5 and 8 days post T cell transfer (FIGS. 8A and 8B). At day 5 after transfer, a substantial expansion of 6.5 cells was observed in animals transplanted with LV-HA transduced HSC. 6.5 T cells expanded to 30% of total splenic CD4 cells in animals transplanted with HSC transduced with EF.HA and DR.HA respectively. These numbers were significantly greater than in animals receiving control GFP-transduced HSC (4%). The expansion of 6.5 T cells in animals receiving HA-transduced HSC was also significantly greater than animals vaccinated with recombinant vaccinia-HA (11%, data not shown), which in our hands is an extremely potent HA vaccine (Sotomayor, E. M. et al. (1999), *PNAS* 96:11476; and Sotomayor, E. M. et al. (1999), *Nat. Med* 5:780). The frequencies of HA-specific CD4+ T cells remained high (7-10% vs 2% in the GFP control) when animals were examined 8 days after transfer (FIG. 8B). To determine whether this expansion in vivo represented induction of effector function, we examined IFN-gamma release by these T cells after in vitro culture with HA antigen. We and others have previously shown that IFN-γ production correlates with T cell activation to effector function and is significantly suppressed when antigen-specific tolerance is induced (Staveley-O'Carroll, K. et al. (1998), *PNAS* 95:1178; Sotomayor, E. M. et al. (1999), *PNAS* 96:11476; and Sotomayor, E. M. et al. (1999), *Nat. Med* 5:780). Indeed, we found robust IFN-γ production by 6.5 T cells from animals transplanted with HA-transduced HSC that was significantly higher than from the animals transplanted with GFP-transduced control HSC (FIG. 8C). These results indicate that potent T cell activation is achieved with immunization with HA-transduced HSC engraftment and FL treatment.

As a parallel comparison group, BALB/c mice were immunized with ex vivo differentiated (mature) DCs that were transduced with HA-expressing LV during ex vivo culture (the classic ex vivo DC-transduction/vaccinatio- n paradigm). Differentiated DCs were transduced with EF.HA-expressing actively stimulated HA-specific T cells in vitro (FIG. 7). However, multiple sc immunizations with these mature HA-transduced DCs induced a relatively modest expansion of HA-specific 6.5 cells in vivo—far less than the level observed in animals transplanted with HA-transduced HSC (FIG. 8). These preliminary results indeed suggest that transduction of HSC followed by transplantation and in vivo DC differentiation may be much more efficient to activate antigen-specific T cells. Thus, even without in vivo DC activation by agents such as CD40, the strategy of transduction of HSC, followed by transplantation and induction of in vivo DC differentiation, appears to be an extremely promising approach to activate antigen-specific T cells.

Based on the data that DR promoter driven expression of HA may somewhat enhance in vivo T cell expansion relative to a constitutive promoter (EF1a), one could utilize other DC-specific promoters. These include the CIITA promoter 1, which was reported functional solely in DC; Mach, B. (1999), *Science* 285:1367; and/or the promoters of two novel DC specific genes (B7-DC and MINOR) that were recently discovered (see e.g. Tseng, S. Y. et al. (2001), *J. Exp. Medicine*, in press).

After HSC engraftment, patients may be treated systemically with various agents to promote DC differentiation in vivo. These include specific cytokines, such as GM-CSF, FL, and/or an agonist anti-CD40 antibody. Subsequent to these manipulations, mature T cells may be transferred into patients—the analogue of DLI that is now routinely used in clinical BMT settings.

While systemic administrations of FL and CD40 agonists are potent in promoting DC expansion, differentiation and activation, they may also be potentially toxic to hosts. To overcome this problem and take advantage of the selective transgene expression in transduced cells by our novel LV system, bi-cistronic vectors in which a DC-specific promoter expresses the tumor antigen and drug-inducible DC activator genes are created using standard methods of cloning known in the art (FIG. 2B) (see e.g. Molecular Cloning: A Laboratory Manual, second edition (1989) by Sambrook, Fritsch and Maniatis; Cold Spring Harbor Laboratory Press). The inducible DC activator is based on the intracellular (signal transducing) domain of CD40 linked to the FK506 binding domain of FKBP12. Since 1993, several bivalent analogs of FK506 such as FK1012 and AP1903 have been synthesized (see e.g. Spencer et al. (1993) Science 262: 1019; Amara et al. (1997) PNAS USA 94: 10618; and Clackson et al. (1998) PNAS USA 95: 10437). These compounds are cell permeable, immunologically inert and able to induce crosslinking and signal transduction of chimeric molecules containing the FK506 binding domain and the signaling domain of various molecules including c-kit/SCFR, Epo and Tpo. Accordingly, the invention may be adapted for use with functional intracellular CD40-FKBP chimeric molecule, because this has already been validated with another member of the TNFR/CD40 family, Fas. Amara, J. F. et al. (1997), *PNAS* 94:10618; Clackson, T. et al. (1998), *PNAS* 95:10437; and Thomis, D. C. et al. (2001), *Blood* 97:1249. Specifically a chimeric gene is constructed with the membrane-anchoring domain of NGFR (p75) linked to tandem FKBP domains followed by the cytoplasmic (signaling) domain of CD40. (see Clackson, T. et al. (1998), *PNAS* 95:10437; and Thomis, D. C. et al. (2001), *Blood* 97:1249). The bi-cistronic vectors are then used to co-express the antigen gene and the NGFR-FKBPm2-iCD40 chimera gene controlled by a DC-specific promoter (FIG. 2B). The antigen and NGFR-FKBPm2-iCD40 are co-expressed specifically in differentiated DCs, and only these transduced donor DCs are activated intracellularly and quantitatively through the CD40 pathway after AP1903 administration at a given dose. A second functional intracellular-FKBP chimeric APC-stimulatory gene would be the NGFR-FKBPm2-iFlt3 fusion protein which may obviate the need for systemic FL administration for in vivo DC induction.

DETAILED DESCRIPTION OF THE FIGURES

FIG. 1 depicts lentiviral SIN vectors which allow high levels of stable gene transfer and regulated transgene expression from a selective promoter in transduced cells. The U3 region in the prime LTR is replaced by a non-HIV promoter P1 to allow synthesis of viral genomic RNA in packaging cells. The U3 region in the 3 prime LTR is largely deleted so that it no longer functions as a promoter in target cells post integration. In transduced target cells, the transgene expression mediated by these self-activating (SIN) vectors is solely controlled by the internal promoter (P2) such as from the HLA-DRα (DR) gene. The titers of VSV-G pseudotyped viruses made by transfection in 293 T cells are ~1-6×10$^6$ CFU/ml."

FIG. 2 shows a number of lentiviral vectors expressing the selected antigen and the APC-stimulatory gene. FIG. 2 includes a list of mono-cistronic lentiviral vectors we have made. The promoter from the human housekeeping gene, EF1a, is used as control. Lentiviral vectors under the control of a more DC-specific promoter (such as the CIITA promoter 1) are also included, (β), Bi-cistronic vectors are constructed under the control of DR or a DC-specific promoter. DC activators are constructed by fusing the intracellular signaling domain of CD40 or Flt3 receptor with the FKBP domain. The engineered activator gene linked to e.g. the HA gene by an IRES are selectively expressed inside transduced DCs in a non-active form, which can be activated by a cell permeable, immunologically inert compound such as FK1012. Alternatively, construct vectors selectively expressing CD40 ligand or FLT3 ligand in transduced DC are constructed to generate an autocrine loop. A similar autocrine or paracrine loop can be achieved for the production of GM-CSF and IL-12 by transduced DCs.

FIG. 3 shows that a GFP transgene driven by the DRα promoter is selectively expressed in human HLA-DR+cells differentiated from CD34$^+$cells transduced by the DR.GF-PSIN lentiviral vector. Human CD34$^+$cells from G-CSF mobilized peripheral blood are cultured overnight and transduced once (as described in 3a) with lentiviral vectors. Transgene expression is controlled by the promoter of either human DRα gene (DR.GFP vector) or a housekeeping gene such as EF1α promoter (EF.GFP vector). Transduced cells are cultured either in suspension with GM-CSF, IL-4 and TNFα to allow DC differentiation (A), or in methylcellulose with Epo, G-CSF, GM-CSF SCF, IL-3, and IL-6 to allow erythroid and myelold colony formation (B). Cells differentiated under condition A were harvested at day 7 post induction of differentiation. Cells differentiated under condition B were harvested after 14 days of CFC assays. Cells were then analyzed by FACS for GFP and cell-surface HLA-DR expression. The HLA-Dr+ cells in (B) were likely to be monocytes/macrophages derived from CFU-GM. In addition, we used both lentiviral vectors to transduce non-dividing DC differentiated in vitro from human monocytes. We found that >20% of cells displayed DC phenotypes were readily transduced and conferred persistent GFP expression at moderate levels.

FIG. 4 shows that transduced human CD34+ cells engraft in vivo and generate multiple lineages of GFP+hematopoietic cells including DCs that can stimulate allogeneic human T cell proliferation. Human cord blood CD34+ were transduced either by DR.GFP as in FIG. 3. Transduced cells were i.v. injected into conditioned NOD/SCID mice. Six to ten weeks post BMT, BM cells were harvested from engrafted and the presence of human (CD45+) donor cells (A). Human GFP+ cells that co-expressing CD34 or HLA-DR (MHC II) markers were further analyzed (B). The DRα promoter directed transgene expression exclusively in MHC II+ cells and in both CD34+ and CD34+ cells. Similar results were obtained from human cells engrafted in mouse spleen, except percentages of CD45+ and CD34+ were lower (data not shown). Engrafted human cells from mouse BM were purified (by depleting mouse cells) and cultured subsequently under DC differentiation conditioned as in FIG. 3A. These differentiated DCs after subsequent culture were analyzed by FACS(C and D). The DR.GFP-transduced cells showed highly selective expression in MHC II$^{high}$ cells after DC differentiation and maturation (C). Their morphology and phenotypes (D) and their functional activities in stimulating allogenic human T cells (E) were also determined. The potency of these BM or splenic (SP) DCs post BMT following gene transduction (by either DR.GFP or EF.GFP LV) was high in this in intro assay, and similar to those (CB CD34–DC) derived directly from CD 34+ cells without BMT (E).

FIG. 5 shows that a GFP transgene driven by the DRα promoter is selectively expressed in mouse MHC II+ cells differentiated from bone marrow cells transduced by the DR.GFP SIN lentiviral vector. After one round of lentiviral transduction, mouse BM cells were cultured with GM-CSF and 10% FBS. Cells in suspension were discarded and adherent cells were fed at day 2 and 4. At day 6 adherent cells were transferred to new culture plates. Suspension cells were further selected at day 7 and harvested at day 8 post differentiation. The DC-enriched cell populations were analyzed by FACS for GFP and cell-surface I-E (MHCII) expression. The sub-populations with the highest level of cell-surface I-E expression were known to be DC whereas the sub-populations with medium to low levels of the cell-surface IE expression were immature DC and/or monocytes/macrophages. Intracellular MHC II molecules were detected in the latter population. Note that the DR.GFP vector did not express in cells lacking cell-surface I-E (MHC II) expression.

FIG. 6 shows selective transgene expression mediated by the DRα promoter in mouse donor-derived DCs post transduction and BMT. Mouse HSCs harvested from BM of BALB/c mice (without 5-FU pretreatment) were enriched by depleting mature cells expressing various hematopoietic lineage markers. After overnight culture, stimulated cells were transduced by VSV-G pseudotyped DR.GFP LV. After 1-2 rounds of transduction, cells were either infected into lethally irradiated BALB/c mice or culture in vitro (with GM-CSF) for DC differentiation (as shown in FIGS. 5 and 7). Six to ten weeks after transplant, BM or splenic cells harvested from engrafted mice were further analyzed for their DC compartment. Splenic DCs were enriched and activated by overnight culture. The phenotypes and transgene expression are shown in (A) and (B), respectively. (C): BM cells from engrafted BALF/c mice were further differentiated into DCs as in FIG. 5. Note that either donor engraftment or gene transduction rate, judged by percentages of GFP+ cells, is underestimated, since it is unlikely that we transduced all the donor cells.

FIG. 7 shows mouse DCs differentiated from transduced BM cells by the DR.HA lentiviral vector can specifically and potently stimulate the proliferation of HA-specific T cells (from the 6.5 HA-TCR Tg mice).

FIG. 8 shows transduced HSCs post BMT greatly stimulate the proliferation of HA-specific CD4+ T cells and IFN-γ production following adoptive T cell transfer. This illustrates the ability of DR.HA-transduced HSCs post BMT to initiate HA-specific immune responses after T cell transfer from the 6.5 HA-TCR Tg mice, 3 weeks post BMT with GFP- or HA-transduced HSC. Recipient mice were treated with FL daily for 10 days to expand and stimulate DC. At day 8, 6.5 T cells (2.5 g$^8$) were iv transferred. Frequencies of the 6.5 clongenic CD+ T cells in spleen were measured by FACS with anti-6.5 TCR ad anti-CD4 antibodies at day 5(A) or (B) after T cell transfer. CD4- cells are shown and percentage of 6.5 clonotypic cells among total CD4+ T cells are indicated (A and B). IFN-γ production of harvested T cells at day 8 were also measured (C). Harvested splenocytes from animals engrafted with GFP- transduced or HA-transduced HSC were incubated with naive BM-derived DC (as APCs) pulsed with the HA (Class II-restricted) peptide. The released IFN-γ in the first 24 hours measured by ELISA. Average of duplicated samples were plotted.

Equivalents

Those skilled in the art will recognize, or be able to ascertain using no more than routine experimentation, numerous equivalents to the specific polypeptides, nucleic acids, methods, assays and reagents described herein. Such equivalents are considered to be within the scope of this invention and are covered by the following claims.

The invention claimed is:

1. A method of upregulating a T cell-dependent immune response to an antigen in a mammalian host comprising:
   providing a population of CD34+ hematopoietic stem cells;
   introducing into said population of CD34+ hematopoietic stem cells a first gene, encoding the antigen, and a second gene, encoding a factor that regulates antigen presenting cell differentiation, maturation, expansion or activation to create a population of transgenic cells;
   transplanting said transgenic cells into the mammalian host via intravenous injection before allowing the transgenic cells to develop into antigen presenting cells that express the antigen; and
   allowing said transgenic cells to develop into antigen presenting cells that express said antigen, thereby upregulating a T cell-dependent immune response to the antigen in the mammalian host.

2. The method of claim 1, wherein the population of CD34+ hematopoietic stem cells are provided from an autologous bone marrow graft.

3. The method of claim 1, wherein the population of CD34+ hematopoietic stem cells are provided from an allogeneic bone marrow graft.

4. The method of claim 1, wherein the antigen is a tumor antigen.

5. The method of claim 4, wherein the tumor antigen is selected from the group consisting of: a prostate-specific membrane antigen (PSMA), a HER2/neu gene antigen, an idiotypic immunoglobulin antigen, an idiotypic T cell receptor antigen, an SV40 antigen, and a carcinoembryonic antigen (CEA).

6. The method of claim 1, wherein the factor that regulates antigen presenting cell differentiation, maturation, expansion or activation is selected from the group consisting of: iCD40-FKBP; iFlt3-FKBP; CD40 ligand; Flt3 ligand; GM-CSF; and IL-12.

7. The method of claim 1, wherein said first gene encoding the antigen is operably linked to a dendritic cell-specific promoter.

8. The method of claim 7, wherein the dendritic cell-specific promoter is selected from the group consisting of: an EF 1 a promoter; an HLA-DR promoter; a CIITA P 1 promoter; a B7-DC promoter; and a minor gene promoter.

9. The method of claim 1, wherein upregulation of the T cell-dependent immune response effects an immune response against a tumor antigen.

10. A method of upregulating a T cell-dependent immune response to an antigen in a mammalian host comprising:
   providing a population of CD34+ hematopoietic stem cells;
   introducing into said population of CD34+ hematopoietic stem cells a first gene, encoding the antigen to create a population of transgenic cells;
   contacting said transgenic cells with a factor that regulates antigen presenting cell differentiation, maturation, expansion or activation;
   transplanting said transgenic cells into the mammalian host via intravenous injection before allowing the transgenic cells to develop into antigen presenting cells that express the antigen; and
   allowing said transgenic cells to develop into antigen presenting cells that express said antigen, thereby upregulating a T cell-dependent immune response to the antigen in the mammalian host.

11. The method of claim 10, wherein the population of CD34+ hematopoietic stem cells are provided from an autologous bone marrow graft.

12. The method of claim 10, wherein the population of CD34+ hematopoietic stem cells are provided from an allogeneic bone marrow graft.

13. The method of claim 10, wherein the antigen is a tumor antigen.

14. The method of claim 13, wherein the tumor antigen is selected from the group consisting of: a prostate-specific membrane antigen (PSMA), a HER2/neu gene antigen, an idiotypic immunoglobulin antigen, an idiotypic T cell receptor antigen, an SV40 antigen, and a carcinoembryonic antigen (CEA).

15. The method of claim 10, wherein the factor that regulates antigen presenting cell differentiation, maturation, expansion or activation is selected from the group consisting of: iCD40-FKBP; iFlt3-FKBP; CD40 ligand; FIG ligand; GM-CSF; and IL-12.

16. The method of claim 10, wherein said first gene encoding the antigen is operably linked to a dendritic cell-specific promoter.

17. The method of claim 16, wherein the dendritic cell-specific promoter is selected from the group consisting of: an EF1 a promoter; an HLA-DR promoter; a CIITA PI promoter; a B7-DC promoter; and a Minor gene promoter.

18. The method of claim 10, wherein upregulation of the T cell-dependent immune response effects an immune response against a tumor antigen.

\* \* \* \* \*